United States Patent
Hatta et al.

(10) Patent No.: US 9,559,312 B1
(45) Date of Patent: Jan. 31, 2017

(54) IMIDAZOLE COMPOUND, MATERIAL FOR ELECTRONIC DEVICE, ELECTROLUMINESCENT DEVICE, AND ELECTRONIC DEVICE THEREOF

(71) Applicant: E-RAY OPTOELECTRONICS TECHNOLOGY CO., LTD., Taipei (TW)

(72) Inventors: Taizo Hatta, Kumamoto (JP); Rempei Kuwahara, Kumamoto (JP); Yoshiyuki Hirao, Osaka (JP); Banumathy Balaganesan, Taoyuan (TW); Heh-Lung Huang, New Taipei (TW)

(73) Assignee: E-RAY OPTOELECTRONICS TECHNOLOGY CO., LTD., Taipei (TW)

( * ) Notice: Subject to any disclaimer, the term of this patent is extended or adjusted under 35 U.S.C. 154(b) by 0 days.

(21) Appl. No.: 14/990,288

(22) Filed: Jan. 7, 2016

(51) Int. Cl.
| | |
|---|---|
| *C07D 403/10* | (2006.01) |
| *C07D 401/14* | (2006.01) |
| *C07D 409/10* | (2006.01) |
| *C07D 471/04* | (2006.01) |
| *C09K 11/06* | (2006.01) |
| *H01L 51/50* | (2006.01) |
| *H01L 51/54* | (2006.01) |
| *H05B 33/14* | (2006.01) |
| *H01L 51/00* | (2006.01) |
| *C09K 11/02* | (2006.01) |

(52) U.S. Cl.
CPC ......... *H01L 51/0072* (2013.01); *C07D 401/14* (2013.01); *C07D 403/10* (2013.01); *C07D 409/10* (2013.01); *C07D 471/04* (2013.01); *C09K 11/025* (2013.01); *H01L 51/0052* (2013.01); *H01L 51/0067* (2013.01); *H01L 51/0074* (2013.01); *H01L 51/5012* (2013.01); *H01L 51/5072* (2013.01); *H01L 51/5096* (2013.01)

(58) Field of Classification Search
CPC .. C09K 11/06; H01L 51/5032; H01L 51/5064; H01L 51/0032; H01L 51/5296; H05B 33/14

USPC .......... 544/180; 548/301.7; 252/301.16, 500
See application file for complete search history.

(56) References Cited

FOREIGN PATENT DOCUMENTS

| JP | 2003-282270 | 10/2003 |
| JP | 2014-105209 | 6/2014 |
| WO | 2008085208 | 9/2005 |

OTHER PUBLICATIONS

Huang et al. J. Phys. Chem. C 116, 19458-19466, 2012.*
Ko et al. KR 2016050891, CA 164: 614597, 2016. CAPLUS Abstract provided.*
R. J. Holmes et al., "Blue Organic Electrophosphorence Using Exothermic Host-Guest Energy Transfer", Applied Physics Letters 82, 2422 (2003), doi: 10.1063/1.1568146.
Hayato Tsuji et al., "Bis(carbazolyl)benzodifuran: A High-Mobility Ambipolar Material for Homojunction Organic Light-Emitting Diode Devices", Advance Materials, 2009, 21, 3776-3779.

* cited by examiner

*Primary Examiner* — Venkataraman Balasubramanian
(74) *Attorney, Agent, or Firm* — Jackson IPG PLLC; Demian K. Jackson

(57) ABSTRACT

The present invention mainly provides a new imidazole compound, which can be used to produce electronic devices that are able to operate at low driving voltage and at high current efficiency. The new imidazole compound of the present invention is represented by the following formula (1):

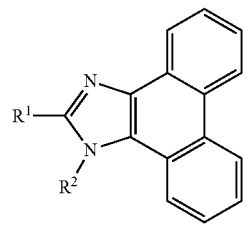

(In the formula (1), $R^1$ and $R^2$ are respectively the same as described in the specification).

10 Claims, 6 Drawing Sheets

IMIDAZOLE COMPOUND, MATERIAL FOR ELECTRONIC DEVICE, ELECTROLUMINESCENT DEVICE, AND ELECTRONIC DEVICE THEREOF

BACKGROUND OF THE INVENTION (a) Field of the Invention

The present invention relates to a new imidazole compound, material for electronic device use, electroluminescent device, and electronic device; and more particularly, the new imidazole compound may be used as host material of a luminous layer of an electroluminescent device that makes up an organic electroluminescent device and material for electronic device use, electroluminescent devices containing the new imidazole compound, and electronic devices containing the material for electronic device use, including electroluminescent devices.

(b) Description of the Prior Art

Up to the present time, there are still many and varied discussions regarding the materials for electronic device use, especially luminescent materials and host materials of a luminous layer making up an organic electroluminescent device.

For example, Japan Patent Document 1 discloses using 2,4,5-triaryl to replace an imidazole compound and 1,2,4,5-tetra-aryl to replace an imidazole compound, the resulting compounds being used in blue fluorescence luminescent materials.

In addition, Japan Patent Document 2 discloses using benzylpyridine derivatives in luminescent materials, and using 2,4,5-tri(6-pyridyl biphenyl) imidazole derivatives to use as a phosphorescent host material.

Moreover, Japan Patent Document 3, in one aspect, discloses using imidazole having at least 1 or 2 electron withdrawing groups, and in another aspect, uses imidazole with electron donating groups, namely, producing a compound to use as a host material use.

Furthermore. Japan non-Patent Document 1 discloses using CBP (4,4,-N,N,-biz(carbazoly-9-yl) biphenyl) or mCP (1,3-di(carbazoly-9-yl) benzene) to use as a host material.

In addition, Japan non-Patent Document 2 discloses using benzodifuran derivative to use as a bipolar host material.

In luminescent devices using phosphorescence luminescent material to use as a luminescent material (dopant), the host material must have the full capacity to transport electrons and electron holes, as well as having good film-forming properties.

However, the stability of a thin film using the well known host compound CBP is inadequate. Moreover, mCP still has the problem of low thermal stability of the devices formed therefrom, In addition, with a view to achieving high luminescence efficiency, in recent years, component structures are constructed from multilayer structures assembled from a great many layers. Hence, there is a need to reduce the number of layers of the component structure to enable simplifying the manufacturing process and reducing the costs. If an electroluminescent device uses benzodifuran derivatives as disclosed in Japan non-Patent Document 2, then an organic single layer or a reduction in the number of layers may be achieved. However, such a distinctive feature of the component structure makes manufacture difficult. Moreover, the film forming manufacturing process is restricted to using a vacuum evaporation method. And the manufacturing process still has the problem of being complicated. As for the present situation, simplification of the materials used in electronic devices is needed both in the component structure and the manufacturing process, nevertheless, up to the present time, no such materials have come to light.

In addition, with a view to achieving high luminescence efficiency, emphasis is first placed on the host material used, however, under the situation where the luminous layer of the host material has low stability, and with the trend moving toward the practicality of the driving stability of the electroluminescent device, problems still remain.

PRIOR ART DOCUMENTS

Patent Documents

Patent Document 1: International Publication No. 2005/085208
Patent Document 2: Japanese Patent Publication No. 2003-282270 bulletin
Patent Document 3: Japanese Patent Publication No. 2014-105209 bulletin
Non-Patent Document 1: Appl. Phys. Lett. 2003, 82, 2422
Non-Patent Document 2: Adv. Mater. 2009, 21, 3776

SUMMARY OF THE INVENTION

The Issues the Present Invention Intends to Resolve

Based on the aforementioned existing circumstances, the present invention expects to develop an organic electroluminescent device provided with adequate performance with respect to driving voltage, current efficiency, and luminescence efficiency. Moreover, the present invention expects to develop a new compound to realize an organic electroluminescent device.

In light of the aforementioned problems and proposals, an object of the present invention lies in providing a new imidazole compound for use in electroluminescent devices, which is able to achieve a low driving voltage and a high current efficiency when the new imidazole compound is used in an electronic device.

In addition, the present invention provides material for electroluminescent device use containing the new imidazole compound, an electroluminescent devices containing the material for electronic device, and an electronic device containing the electroluminescent device.

Means Used to Resolve the Aforementioned Issues

In order to resolve the aforementioned issues, the inventor of the present invention has carried out continuous research and exploration to achieve results that show that the phenanthro-(9,10-d) imidazole compound resolves the aforementioned issues.

Accordingly, the key points of the present invention include the following (1) to (7) points:
(1) Imidazole compound represented by the undermentioned formula (1), (Compound 1)

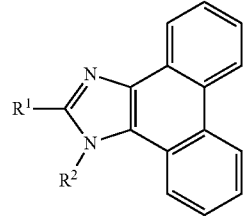

(1)

In the formula (1), $R^1$ is an alkyl having a carbon number of 1~24, an aryl having a carbon number of 6~24, or an aromatic heterocyclic group having a carbon number of 1~24; $R^2$ is a functional group represented by the undermentioned formula (2)

(Compound 2)

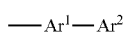

(2)

In the formula (2), $Ar^1$ is an aryl chain, or an aromatic heterocyclic chain; $Ar^2$ is a functional group represented by the undermentioned formulas (3), (4), (5), (6), or (7), (Compound 3)

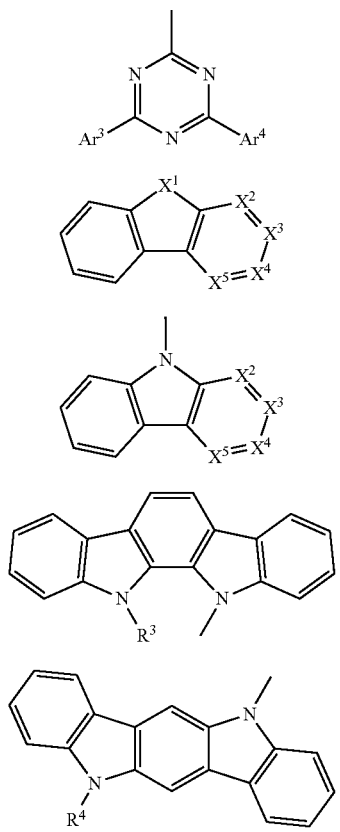

(3)

(4)

(5)

(6)

(7)

In the formula (3), $Ar^3$ and $Ar^4$ are respectively independent, an aromatic group having a carbon number of 6~20, or an aromatic heterocyclic group having a carbon number of 5~18. In the formula (4), $X^1$ is an oxygen atom, a sulfur atom, or a nitrogen atom with a substituent including an alkyl, an aryl, or an aromatic heterocyclic group. In the formulas (4) and (5), $X^2$~$X^5$ are respectively independent, nitrogen atoms or carbon atoms. $R^3$ in formula (6) and $R^4$ in formula (7) are separately an alkyl having a carbon number of 1~24, an aryl having a carbon number of 6~24, or an aromatic heterocyclic group having a carbon number of 1~24.

(2) The aforementioned $R^1$ is an aryl having a carbon number of 6~24, that is, the imidazole compound shown in the aforementioned formula (1), (3) The aforementioned $Ar^2$ is the aforementioned formula (3) or (4), that is, the imidazole compound shown in the aforementioned formula (1) or (2), (4) Material for electronic device use containing any of the imidazole compounds shown in the aforementioned formulas (1)~(3), (5) An electroluminescent device containing the material for electronic device use described in the aforementioned subparagraph (4), (6) An electroluminescent device containing the material for electronic device use described in the aforementioned subparagraph (4) as a host material.

(7) An electroluminescent device containing the material for electronic device use described in the aforementioned subparagraph (4) as an electron hole blocking material.

(8) An electroluminescent device containing the material for electronic device use described in the aforementioned subparagraph (4) as an electron transport material.

(9) An electronic device containing any of the electroluminescent devices described in the aforementioned subparagraphs (5)~(8).

Effectiveness of the Invention

Because the stability of the new imidazole compound and material of the present invention and stability of its film forming function are high, thus, using material for electronic device use containing the new imidazole compound of the present invention, such as application in electroluminescent devices, enables increasing the luminescence efficiency, as well as extending the service life of the electroluminescent device. The driving voltage and current efficiency of electronic devices containing such an electroluminescent device, such as display devices, are good, thus achieving the effect of extending the service life of the electronic device.

In addition, using the imidazole compound of the present invention for use as a host material enables achieving a quantum efficient electroluminescent device having the excellent characteristics of low voltage drive and high stability.

DETAILED DESCRIPTION OF THE PREFERRED EMBODIMENTS

Figure 1:
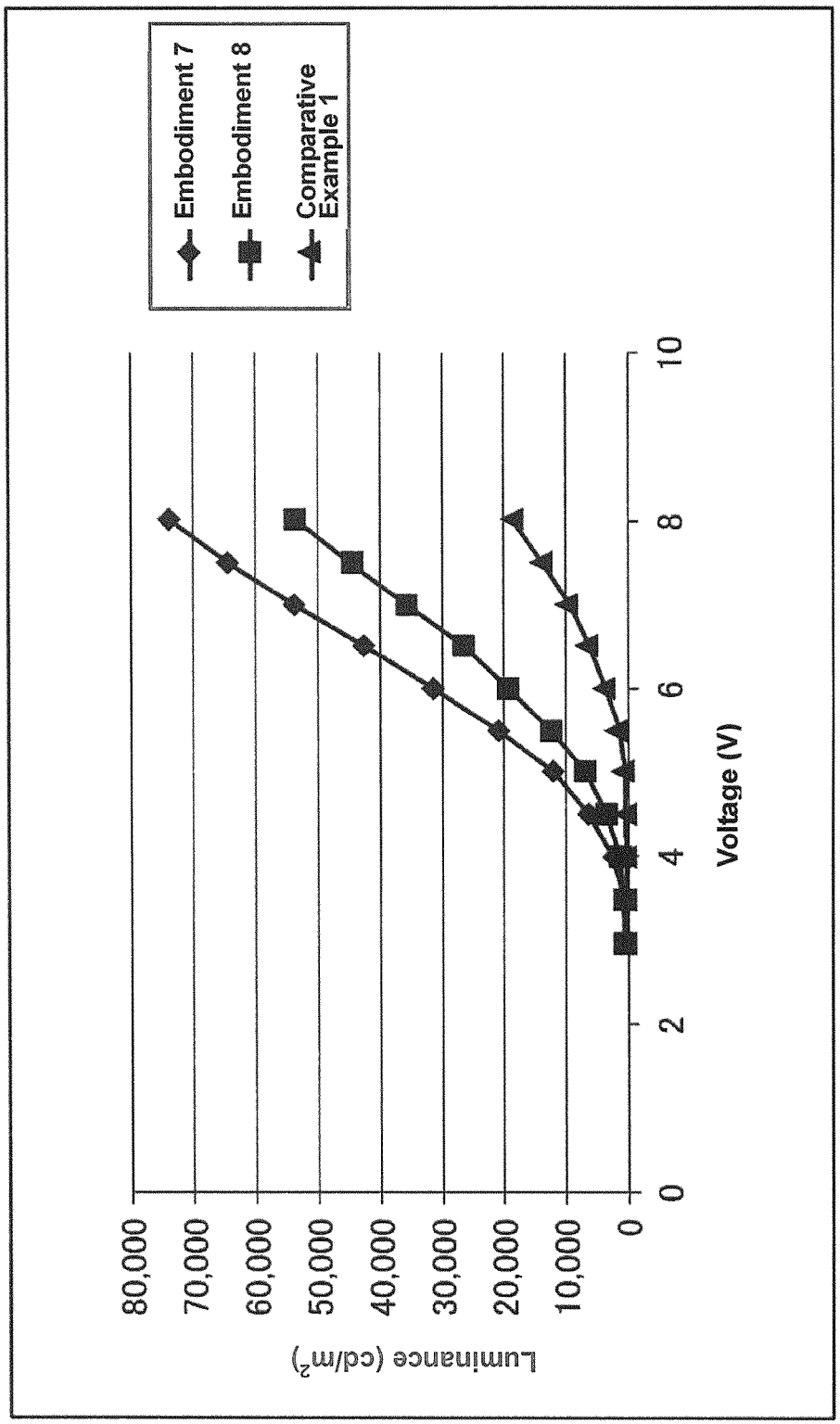
FIG. 1 shows a voltage-light characteristic graph of an electroluminescent device structured according to embodiments 7, 8 and comparative example 1.

The following provides a detailed description of the present invention, wherein an imidazole compound of the present invention is represented by the undermentioned formula (1)

(Compound 4)

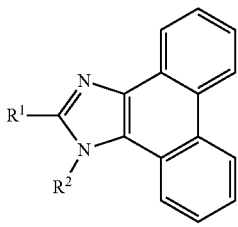

(1)

In the formula (1), $R^1$ is an alkyl having a carbon number of 1~24, an aryl having a carbon number of 6~24, or an aromatic heterocyclic group having a carbon number of 1~24; and $R^2$ is a functional group represented by the undermentioned formula (2), (Compound 5)

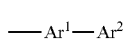

(2)

In the formula (2), $Ar^1$ is an aryl chain, or an aromatic heterocyclic chain, and $Ar^2$ is a functional group represented by the undermentioned formulas (3), (4), (5), (6) or (7), (Compound 6)

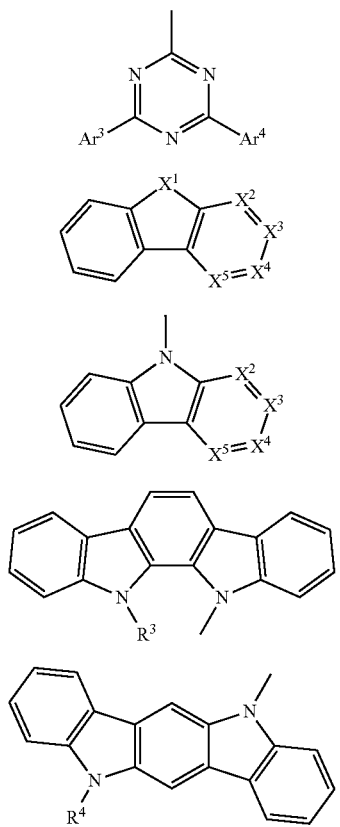

(3)

(4)

(5)

(6)

(7)

In the formula (3), $Ar^3$ and $Ar^4$ are respectively independent, aromatic groups having a carbon number of 6~20, or aromatic heterocyclic groups having a carbon number of 5~18. In the formula (4), $X^1$ is an oxygen atom, a sulfur atom, or a nitrogen atom with a substituent including an alkyl, an aryl, or an aromatic heterocyclic group. In the formulas (4) and (5), $X^2$~$X^5$ are respectively independent, nitrogen atoms, or carbon atoms. $R^3$ in the formulas (6) and $R^4$ in formula (7) are separately an alkyl having a carbon number of 1~24, an aryl having a carbon number of 6~24, or an aromatic heterocyclic group having a carbon number of 1~24.

In the formula (1), examples of the alkyl having a carbon number of 1~24 represented by $R^1$ include methyl, ethyl, propyl, isopropyl, n-butyl, isobutyl, sec-butyl, tert-butyl, n-amyl, amyl, isoamyl, tert-amyl, neopentyl, and n-hexyl. Wherein, an alkyl having a carbon number of 1~12 is preferable, and an alkyl having a carbon number of 1~6 is the optimal preference.

In the formula (1), examples of an aryl having a carbon number of 6~24 represented by $R^1$ include a single-ring aryl of phenyl or tolyl; a condensed multi-ring aryl of phenanthryl, naphthyl, anthryl, fluorenyl, pyrenyl, perylenyl. Wherein an aryl having a carbon number of 6~20 is preferable, and an aryl having a carbon number of 6~14 is the optimal preference.

In the formula (1), examples of the aryl having a carbon number of 6~24 represented by $R^1$ include pyridyl, thienyl, furanyl, oxazolyl, thiazolyl, oxadiazoyl, benzoyl, dibenzofuranyl, dibenzothiophene, pyrazinyl, pyrimidinyl, pyrazolyl, imidazolyl, and phenylcarbazolyl. Wherein, an aromatic heterocyclic group having a carbon number of 2~20 is preferable, and an aromatic heterocyclic group having a carbon number of 3~15 is the optimal preference.

The present invention is based on electric charge acceptance, and an aryl, or an aromatic heterocyclic group is preferable for $R^1$, but the better preference is an aryl having a carbon number of 6~14 or an aromatic heterocyclic group having a carbon number of 3~15.

In the formula (1), $R^2$ is a functional group represented by the aforementioned formula (2). In the formula (2), examples of an aryl chain represented by $Ar^1$ include a bivalent chain (phenyl chain) derived from benzene, a bivalent chain (a multi-ring aryl chain) derived from a multi-ring aryl, a bivalent chain (biphenyl chain) derived from an extended 4,4-diphenyl group biphenyl. An aryl having a carbon number of 6~20 is preferable, a carbon number of 6~18 is a better preference is, and a carbon number of 6~14 is the optimal preference.

Examples of an aromatic heterocyclic chain of $Ar^1$ include a bivalent chain derived from imidazole, furan, thiophene, pyrrole, pyridine. Wherein, a phenyl chain, or a multi-ring aryl chain is preferable for $Ar^1$, with the optimal preference being a phenyl chain.

In the formula (2), $Ar^2$ is a functional group represented by the aforementioned formulas (3)~(7), In the formula (3), examples of an aromatic group having a carbon number of 6~20 of $Ar^3$ and $Ar^4$ include a single ring aryl of phenyl, tolyl; a condensed multi-ring aryl of phenanthryl, naphthyl, anthryl, fluorenyl, pyrenyl, perylenyl; a single ring aryl chain of biphenyl, terphenyl. Wherein, an aryl having a carbon number of 6~20 is preferable, a better preference being an aromatic heterocyclic group having a carbon number of 3~15.

Examples of an aromatic heterocyclic group of the $Ar^3$ and $Ar^4$ having a carbon number of 5~18 Include pyridyl, thienyl, furyl, oxazolyl, thiazolyl, oxadiazoyl, benzothienyl, dibenzofuryl, dibenzothiophene, pyrazinyl, pyrimidinyl, pyrazolyl, imidazolyl, phenylcarbazolyl. Wherein, an aromatic heterocyclic group having a carbon number of 2~20 is preferable, a better preference being an aromatic heterocyclic group having a carbon number of 3~15.
In the formula (3), $Ar^3$ and $Ar^4$ may either be identical or different.
Concrete examples of the functional group represented by the formula (3) are represented by the following formulas of functional groups.
(Compound 7)
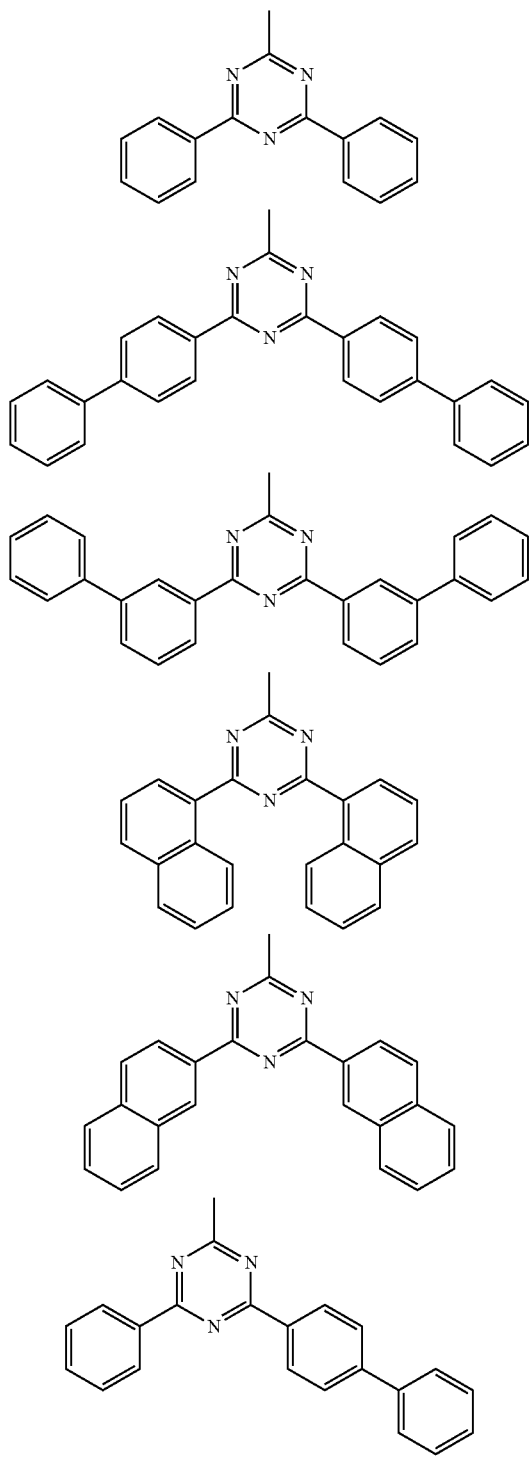
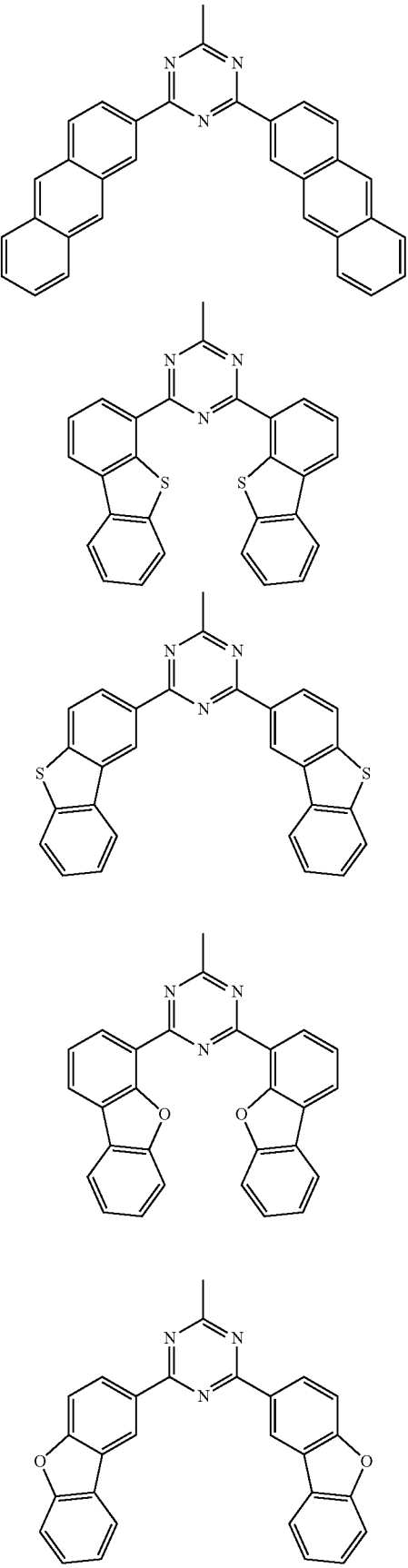
-continued

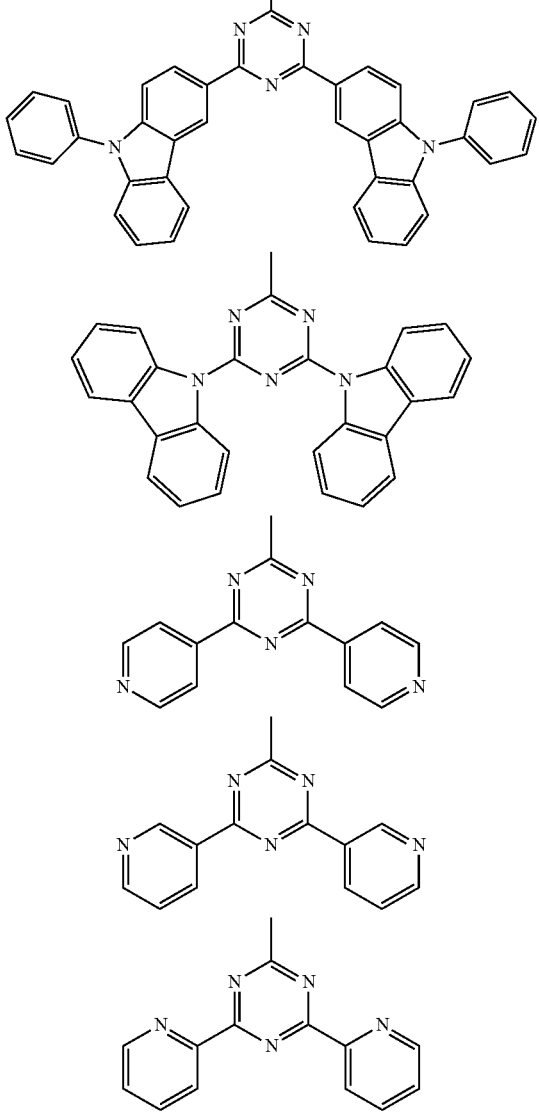

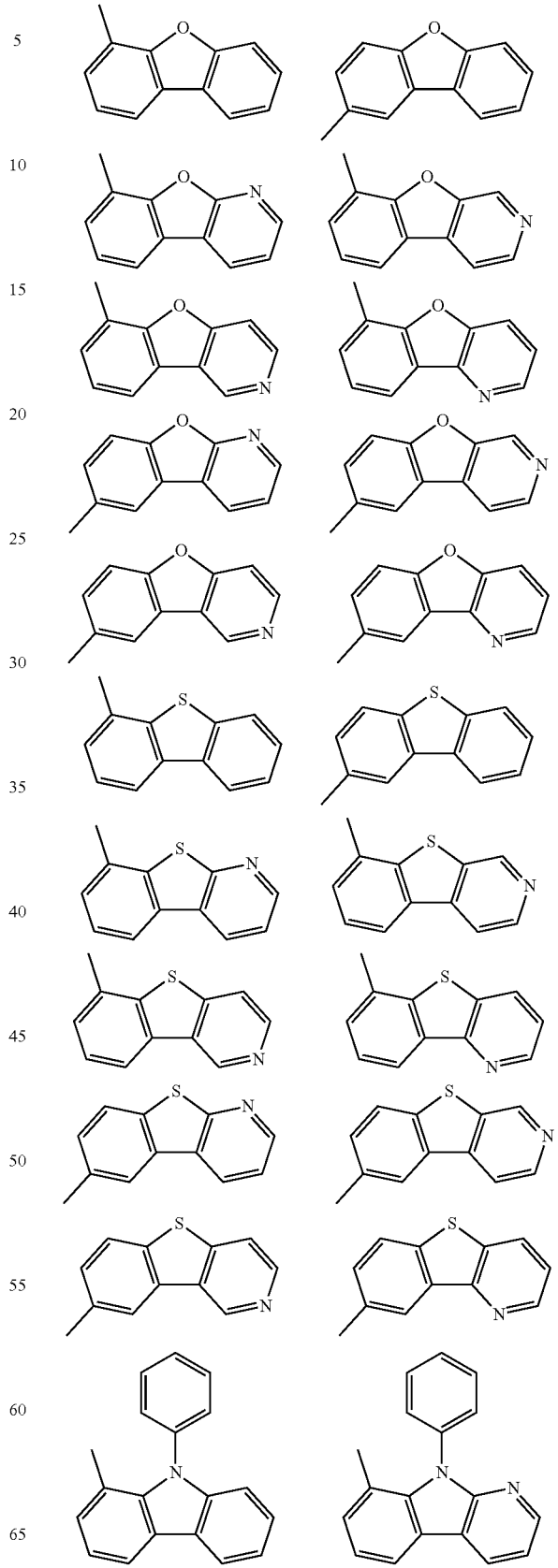

(Compound 8)

In the formula (4), $X^1$ is an oxygen atom, a sulfur atom, or a nitrogen atom with a substituent including an alkyl, an aryl, or an aromatic heterocyclic group.

Examples of the aforesaid alkyl include the aforementioned alkyl having a carbon number of 1~24. Examples of the aforesaid aryl include the aforementioned aryl having a carbon number of 1~24. Examples of the aforesaid aromatic heterocyclic group include the aforementioned aromatic heterocyclic group having a carbon number of 1~24. The preferable functional group is the same.

An oxygen atom, a sulfur atom, or a nitrogen atom with the aryl is preferable for $X^1$.

In the formula (4), $X^2$~$X^5$ are nitrogen atoms or carbon atoms. In the formula (4), $X^2$~$X^5$ may be either identical or different. Wherein, $X^2$~$X^5$ are all carbon atoms is preferable or 1 of them is a carbon atom, Concrete examples of the functional group represented by the formula (4) is represented by the following formulas of functional groups.

-continued

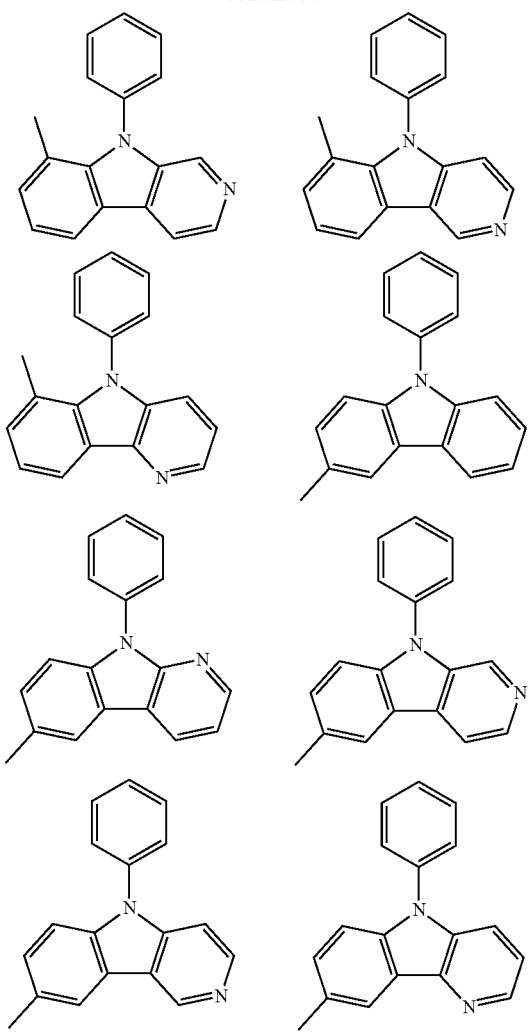

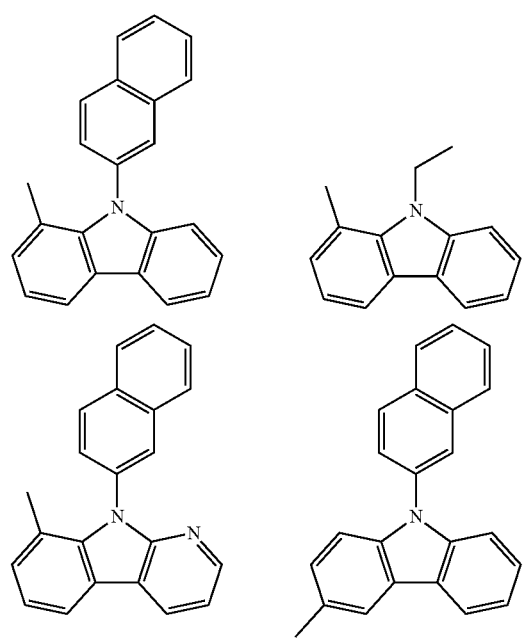

-continued

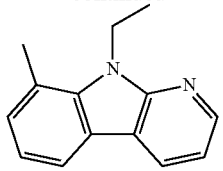

In the formula (5), $X^2 \sim X^5$ are the same as the aforementioned formula (4), Concrete examples of the functional group represented by the formula (5) are represented by the following formulas of functional groups.

(Compound 9)

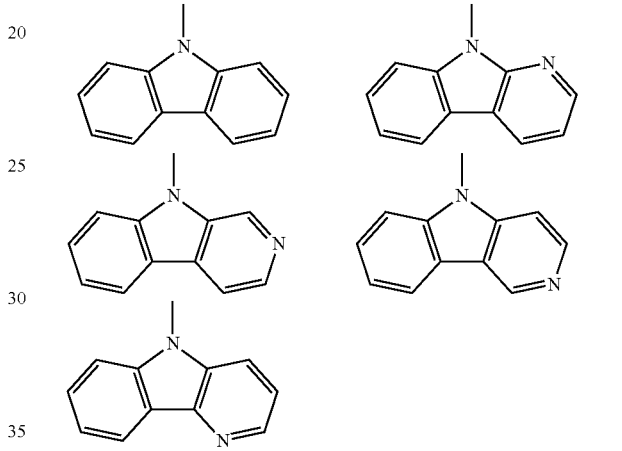

In the formula (6), examples of the alkyl having a carbon number of 1~24, the aryl having a carbon number of 1~24, and the aromatic heterocyclic group having a carbon number 1~24 of $R^3$ include the same functional group represented by the aforementioned formula (1), and the preferable functional group is also the same.

Concrete examples of the functional group represented by the formula (6) are represented by the following formulas of functional groups.

(Compound 10)

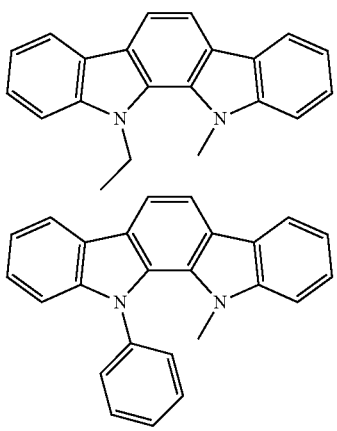

-continued
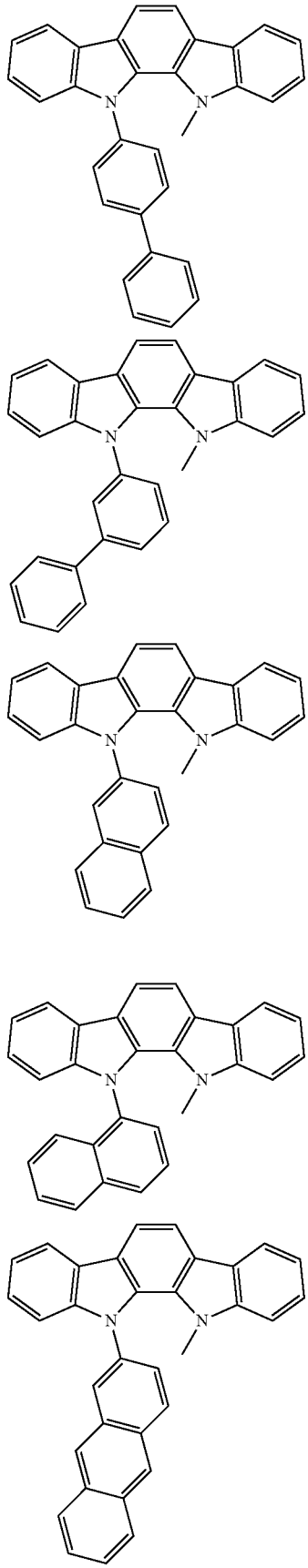
-continued
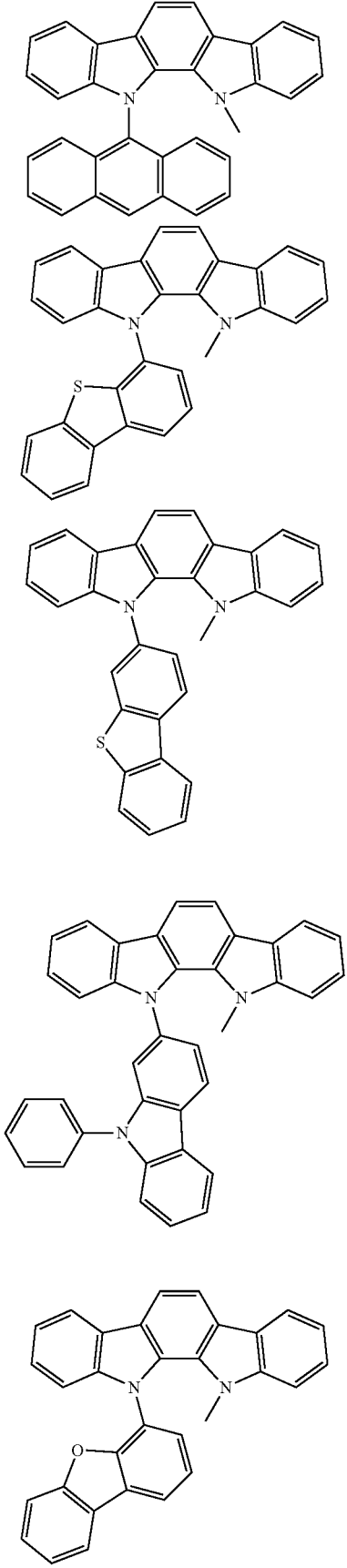

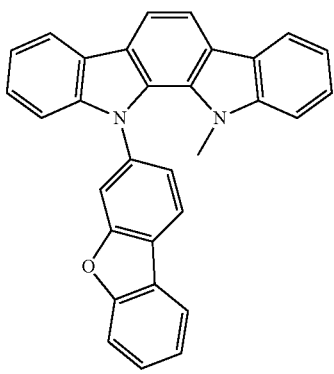

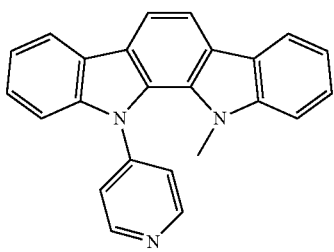

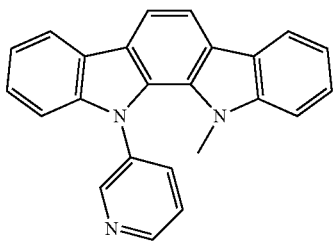

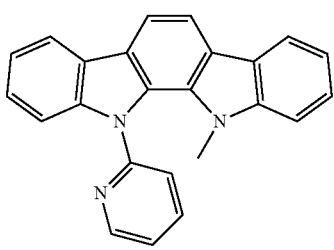 [SMILES: Cn1c2ccccc2c2ccc3c4ccccc4n(-c4ccccn4)c3c21]

In the formula (7), the alkyl having a carbon number of 1~24, the aryl having a carbon number of 6~24, and the aromatic heterocyclic group having a carbon number 1~24 of $R^4$ is the same as the functional group represented by the aforementioned formula (1), and the preferable functional group is also the same.

Concrete examples of the functional group represented by the formula (7) are represented by the following formulas of functional groups.

(Compound 11)

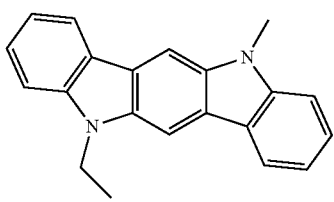

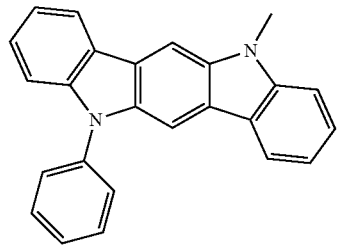

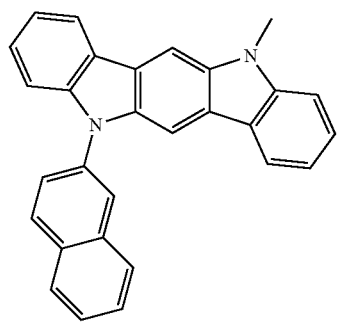

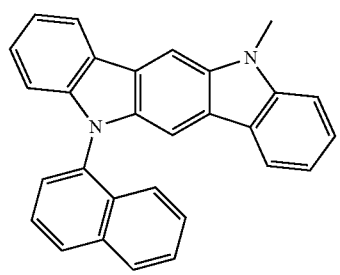

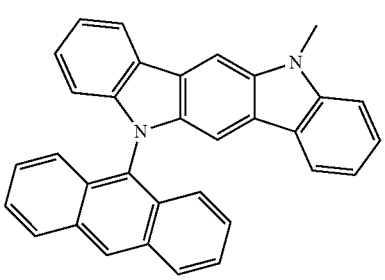

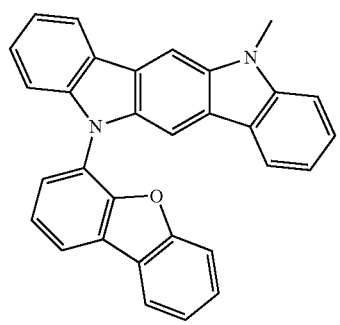

-continued
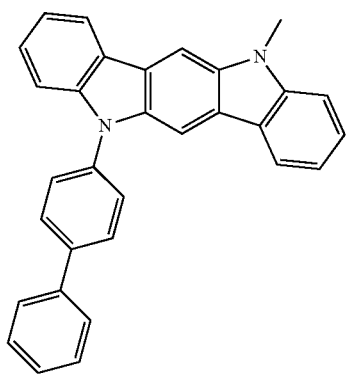
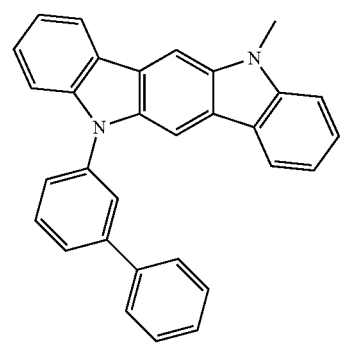
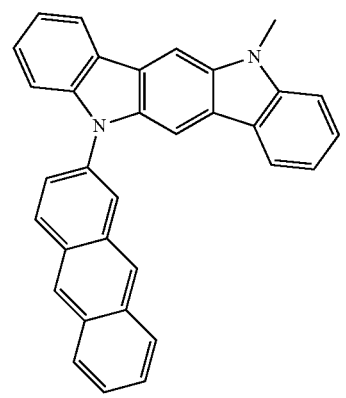
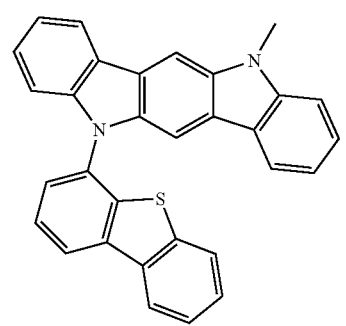
-continued
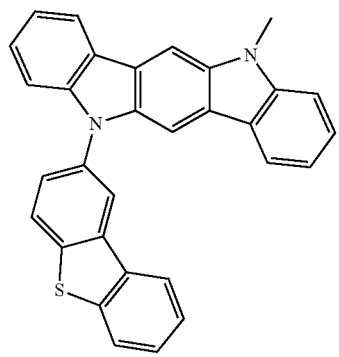
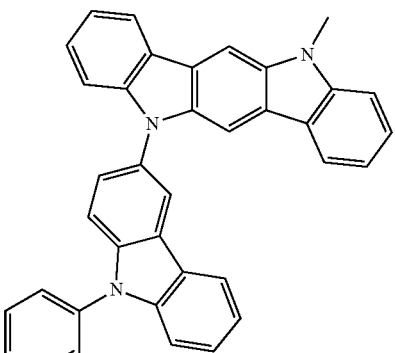
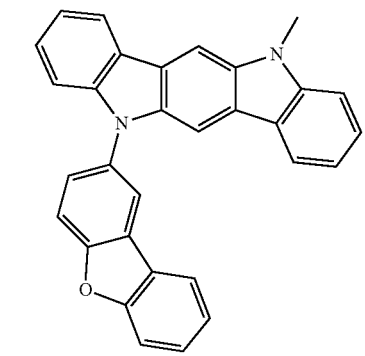
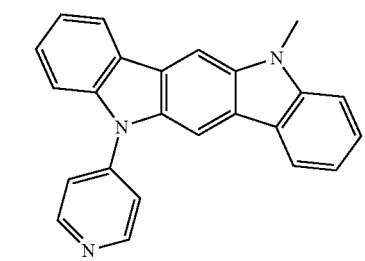
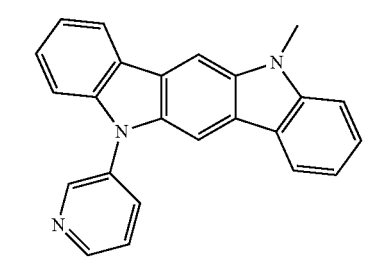

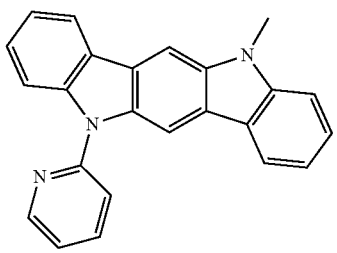
Concrete examples of the imidazole compound represented by the aforementioned formula (1) includes the following formulas of compounds.
(Compound 12)
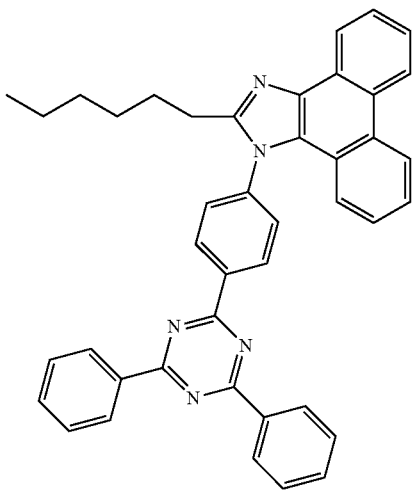
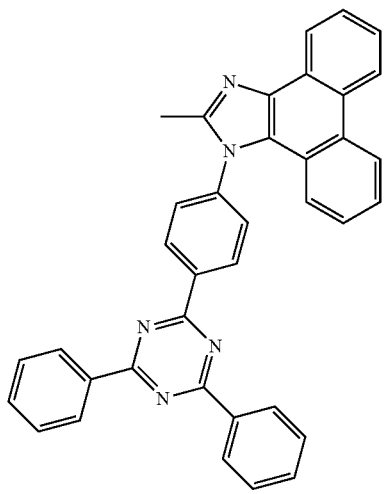
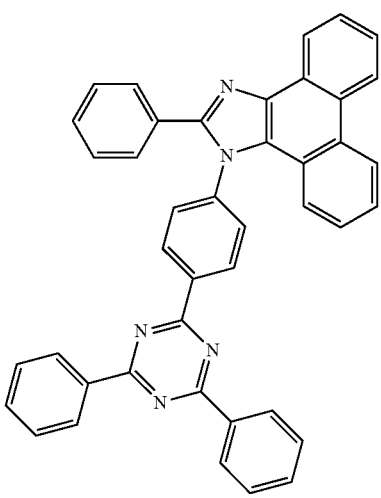
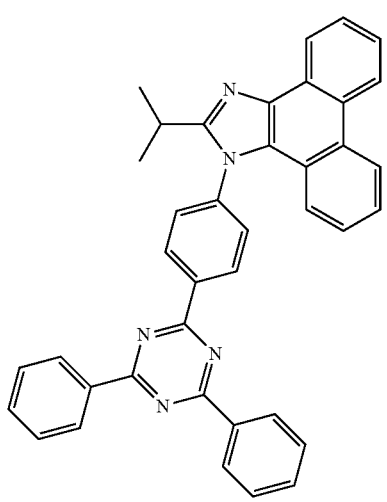
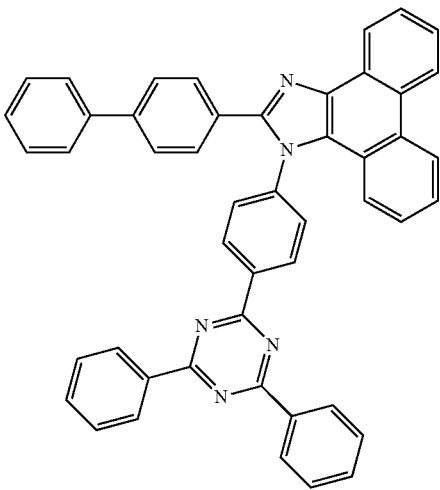

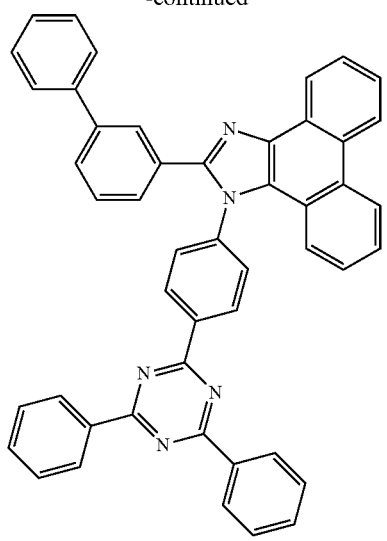
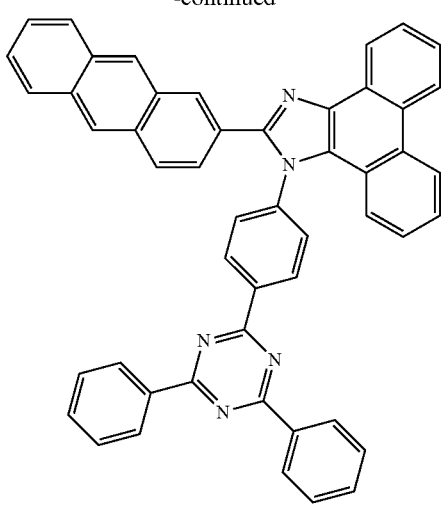
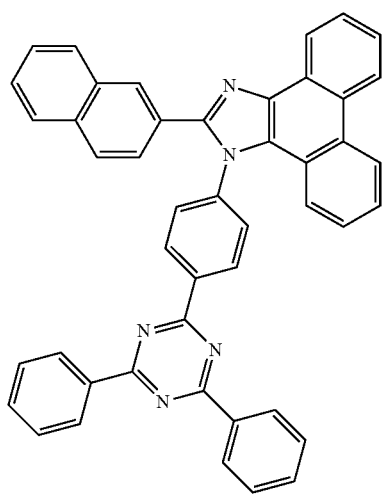
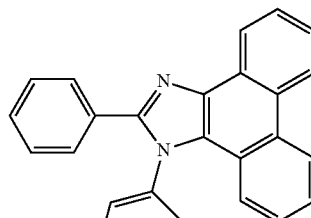
(Compound 13)
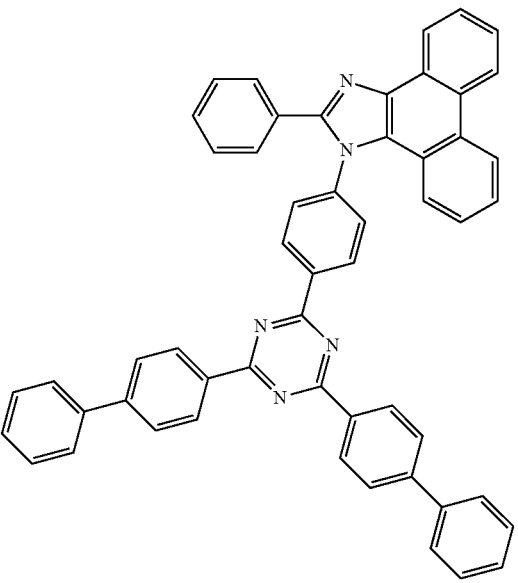
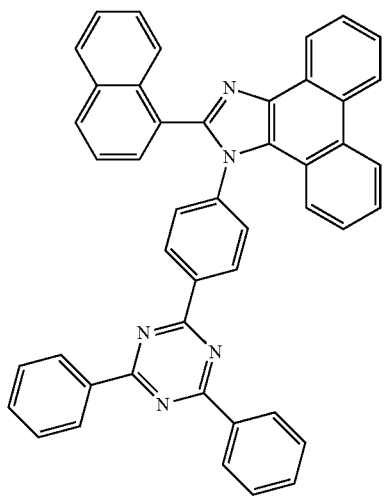
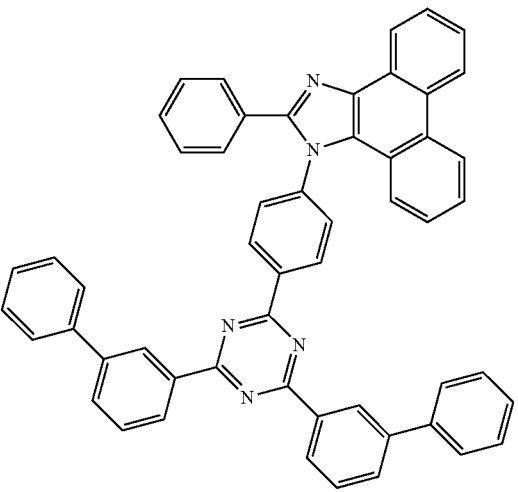

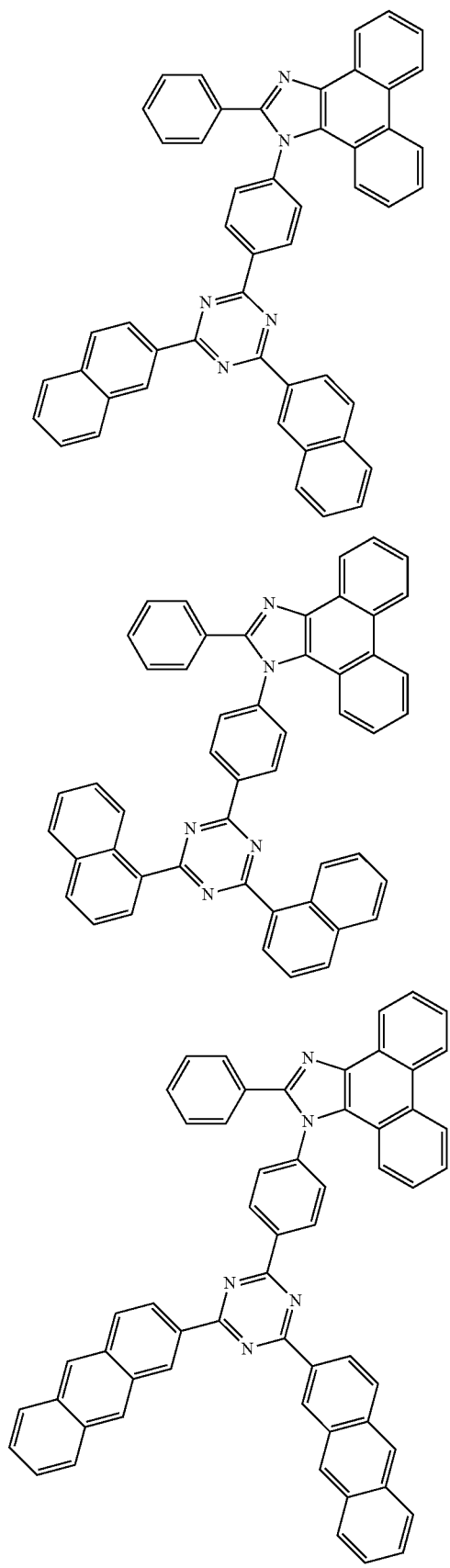
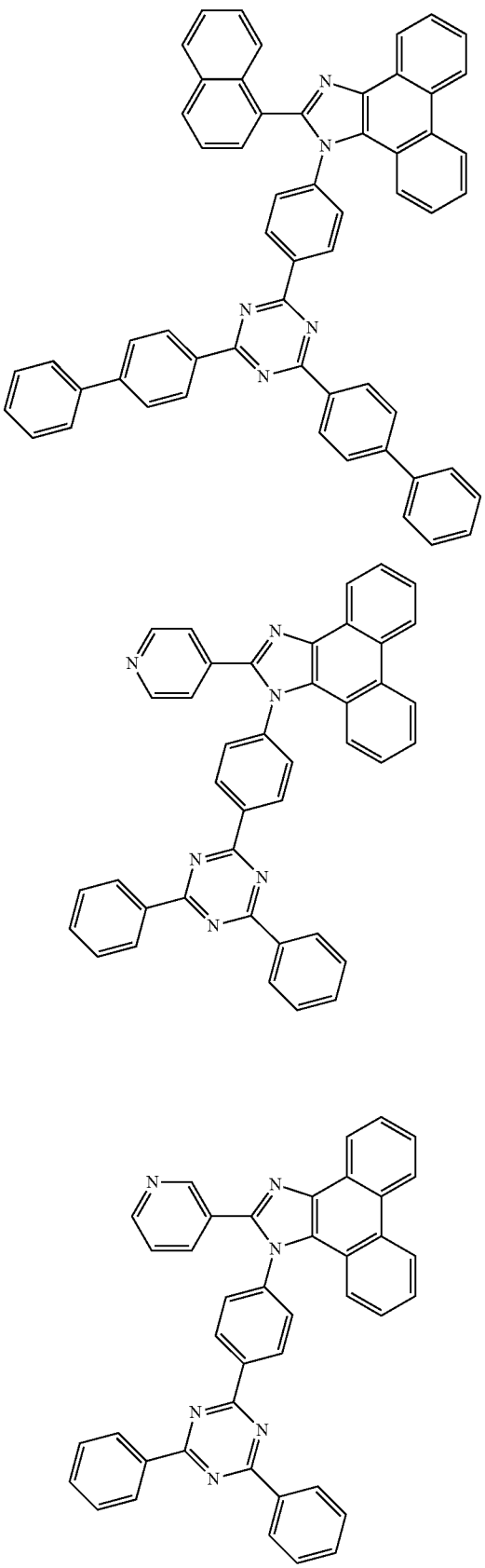

-continued
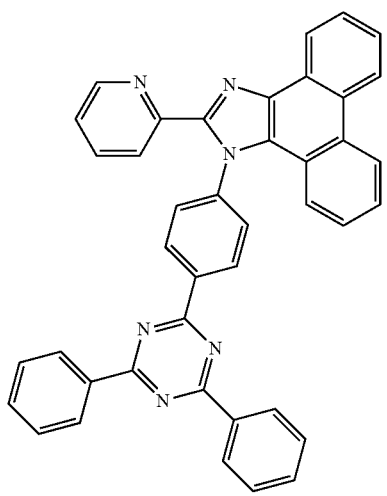
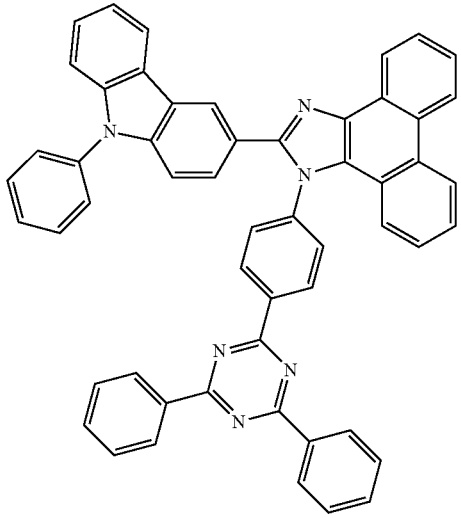
(Compound 14)
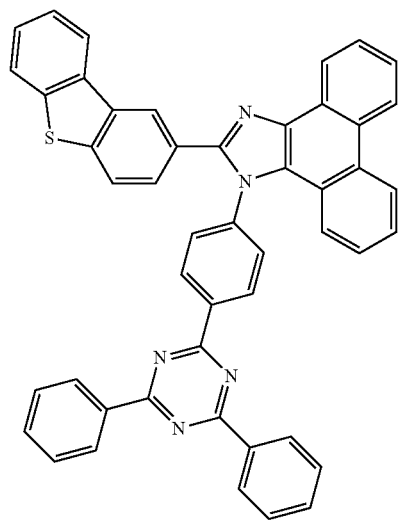
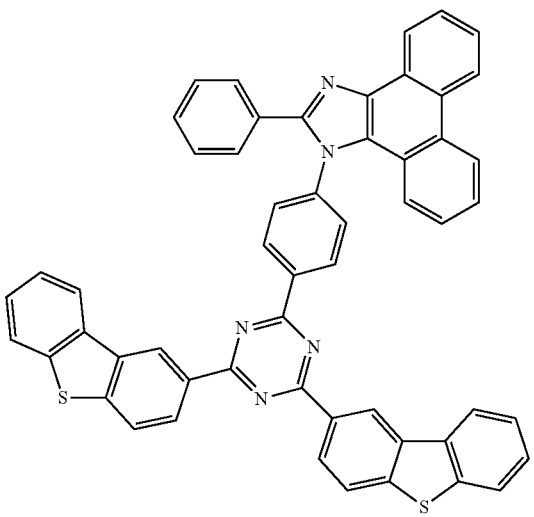
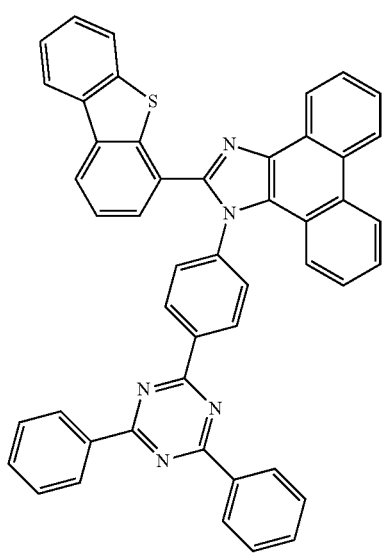
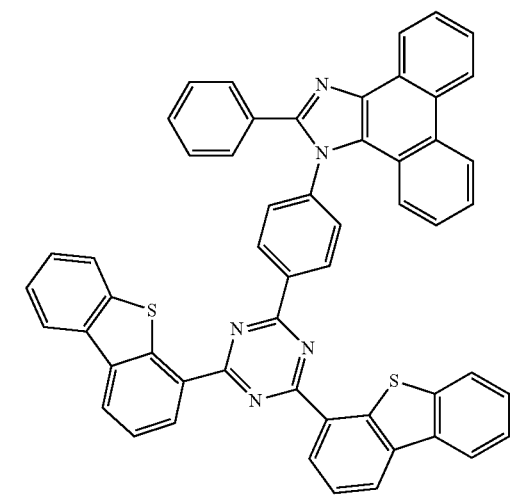

-continued
(Compound 15)
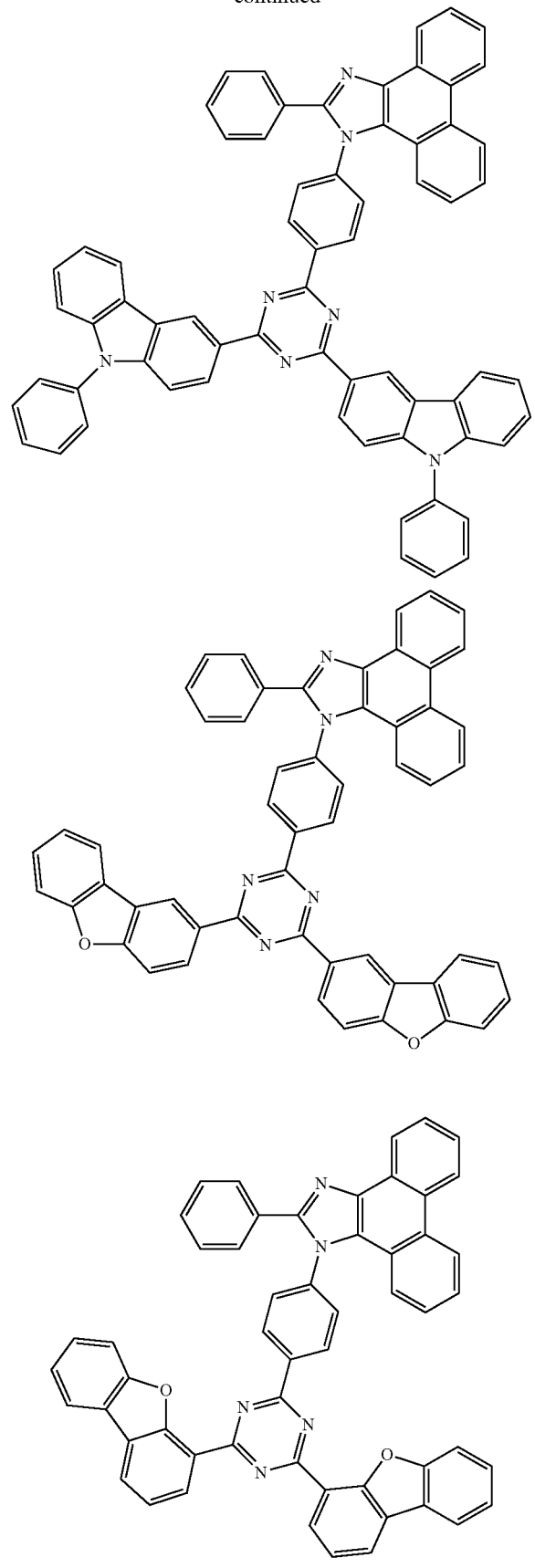

-continued
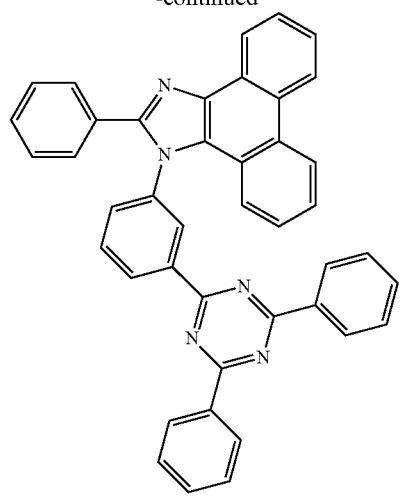
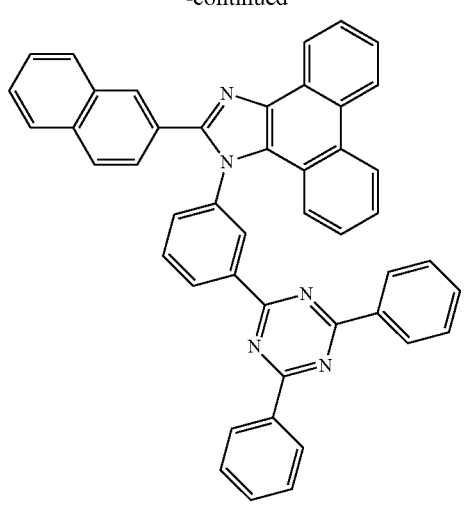
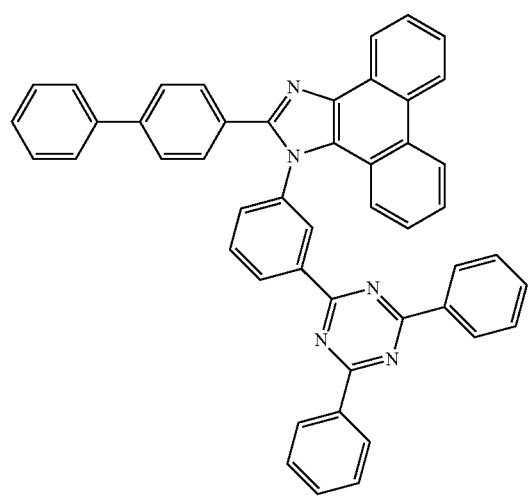
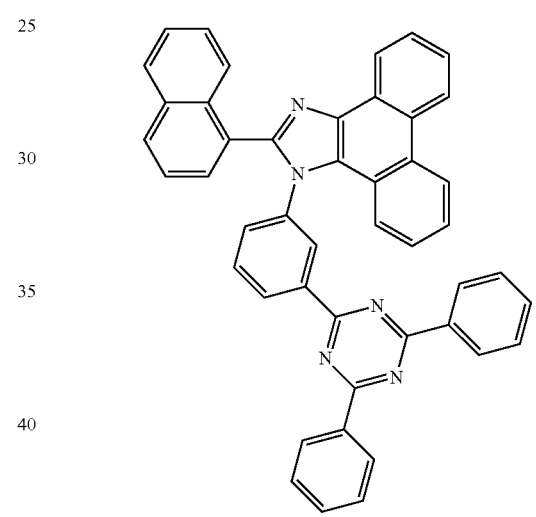
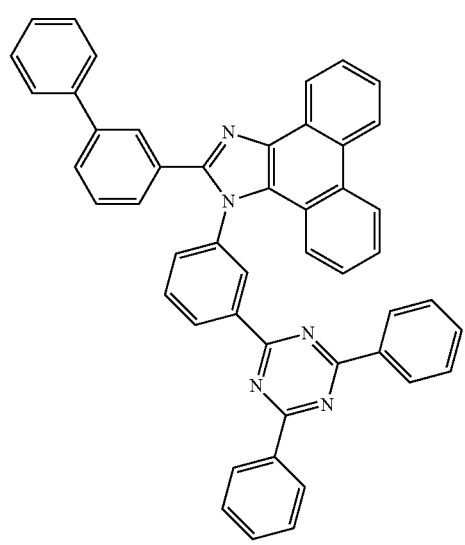
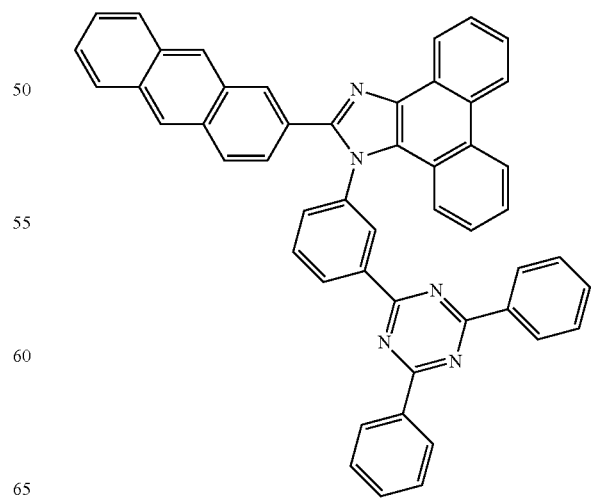

(Compound 16)
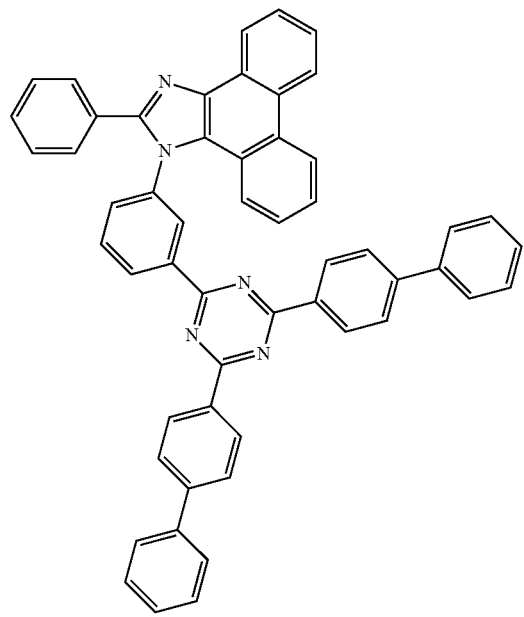
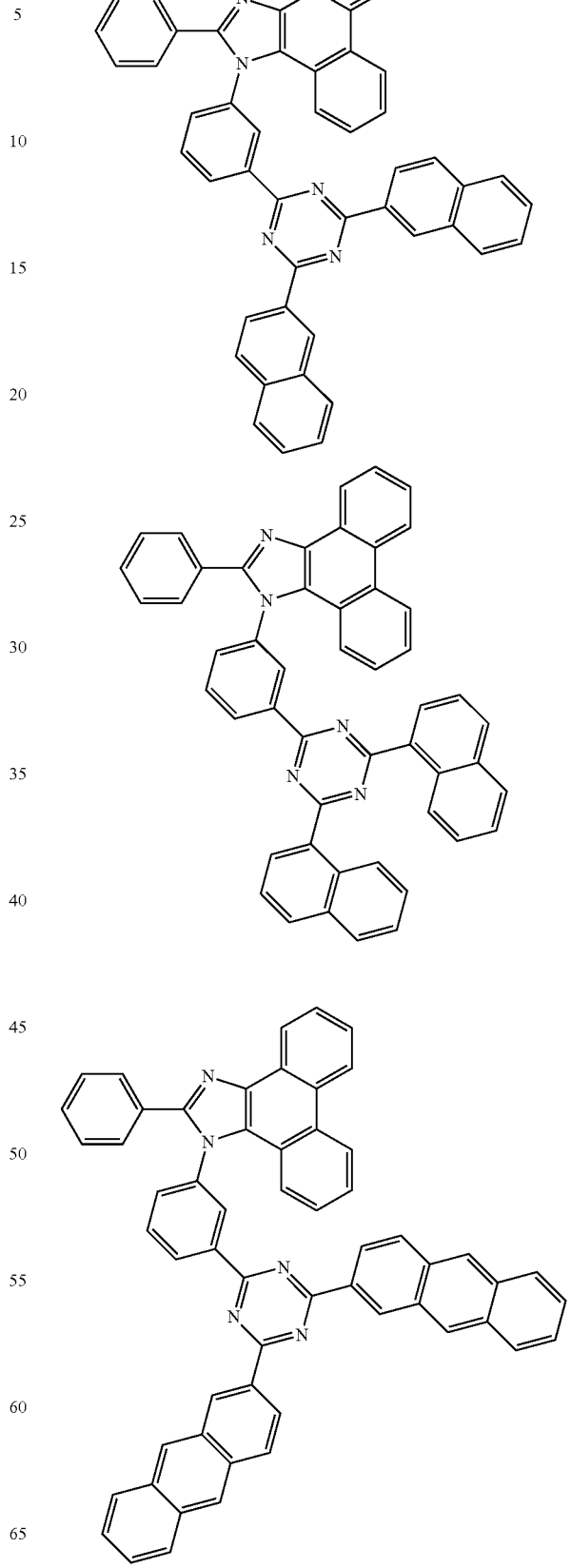

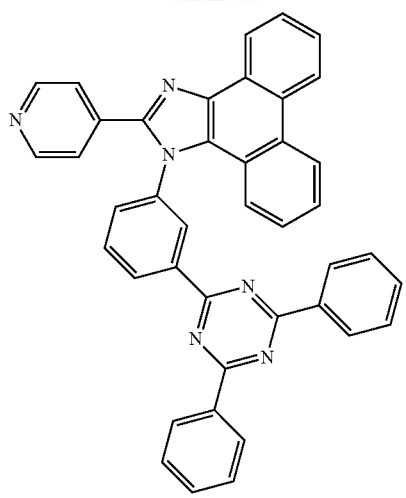
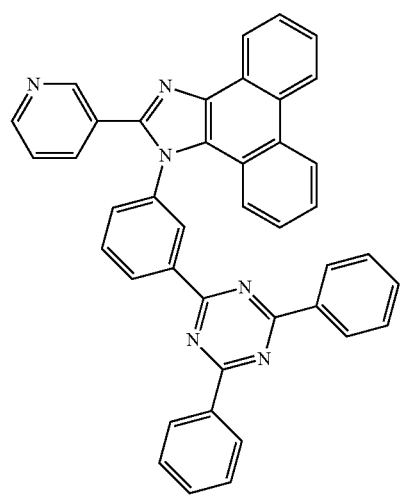
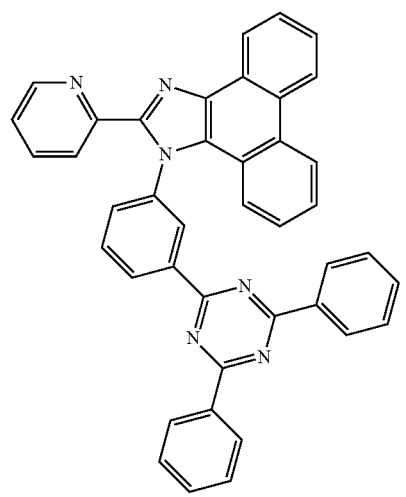
(Compound 17)
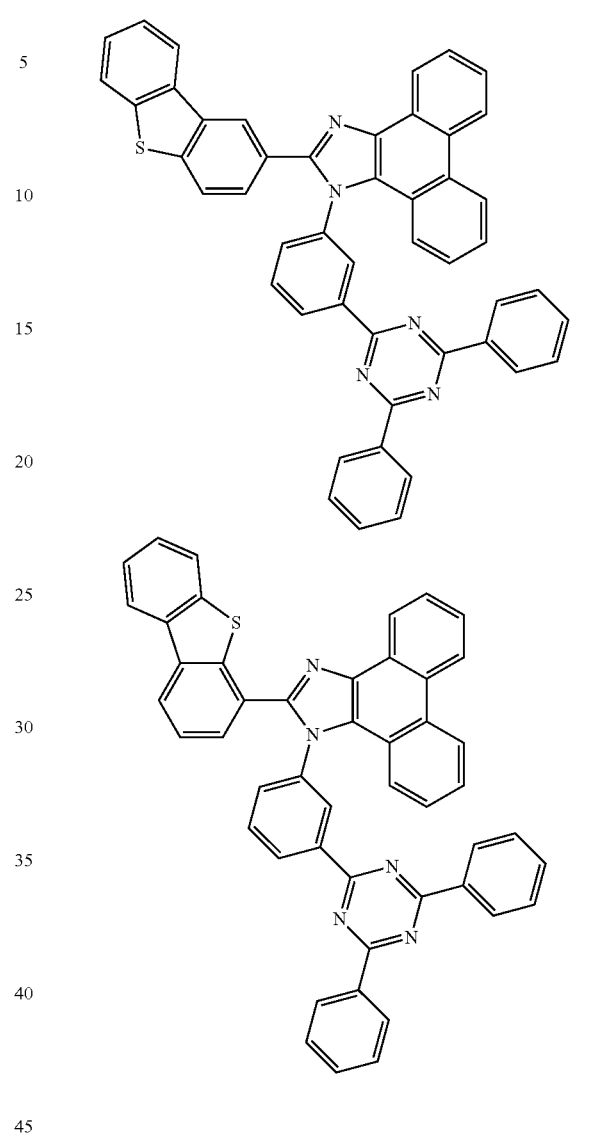
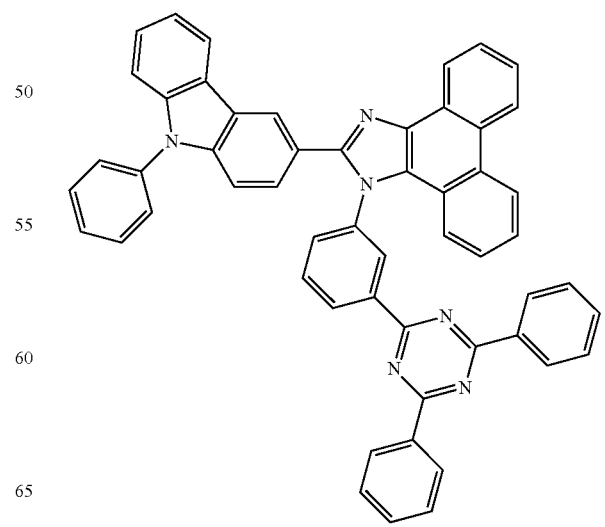

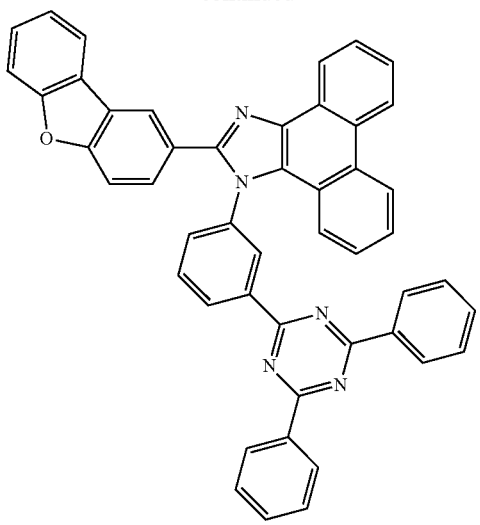
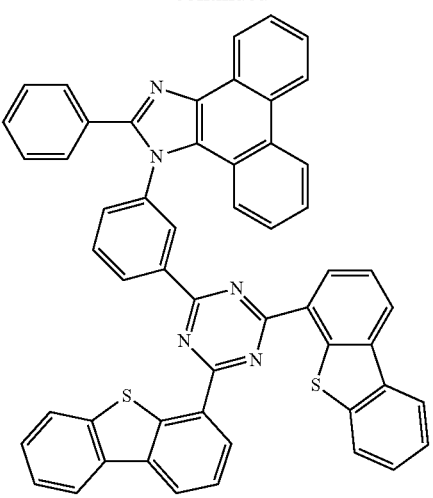
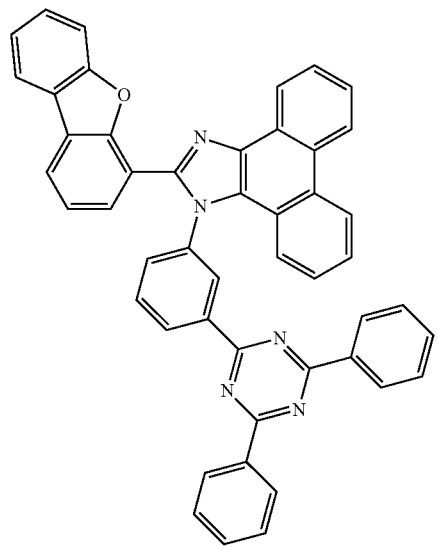
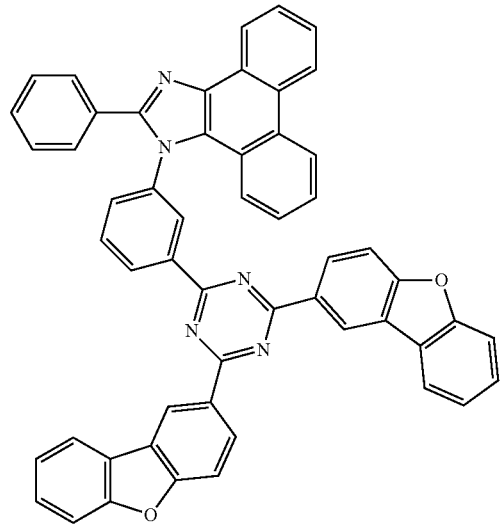
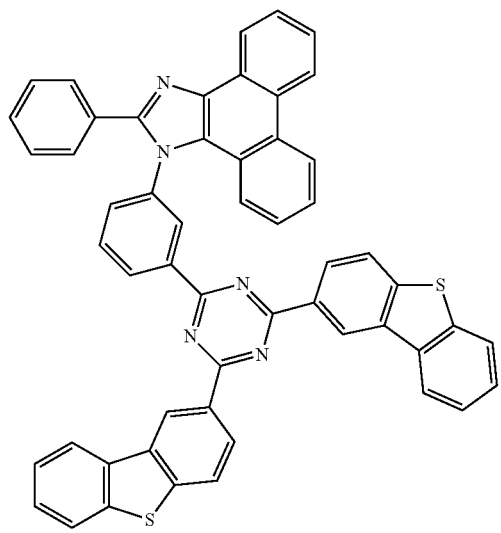
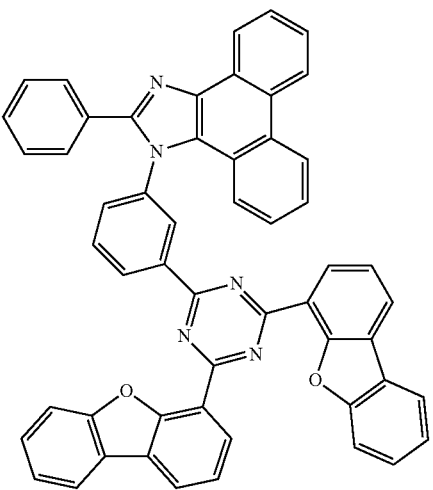

(Compound 18)
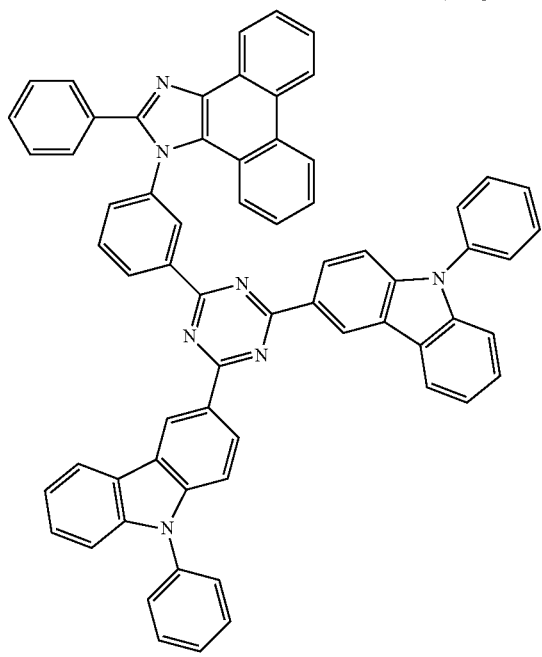
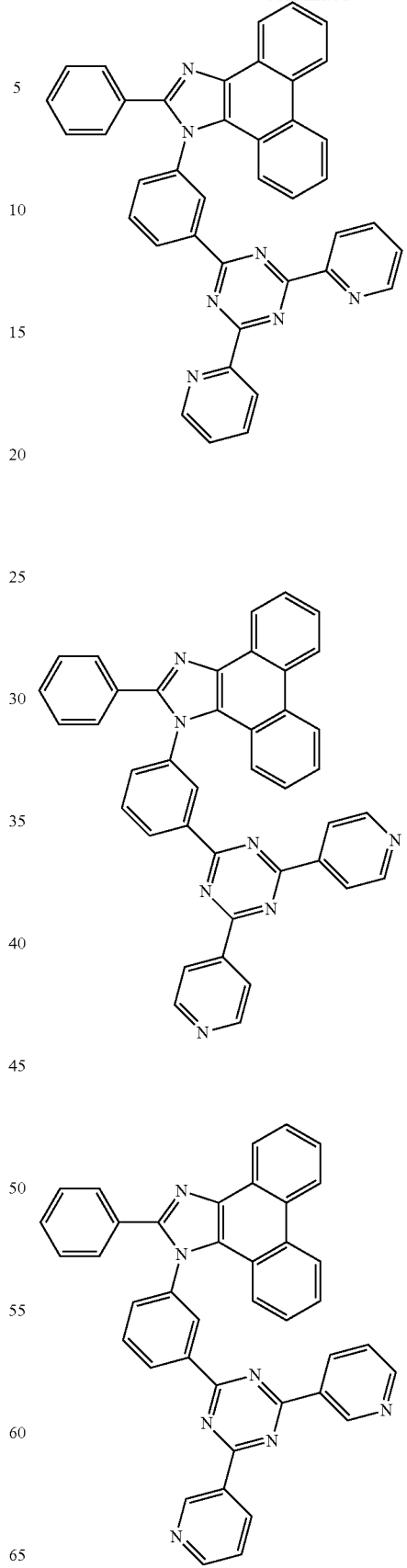

(Compound 19)
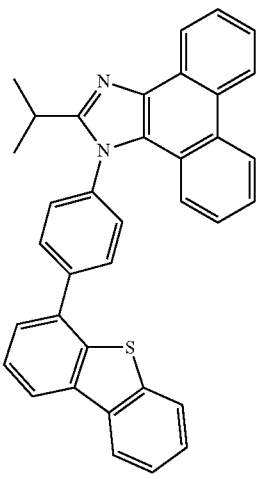
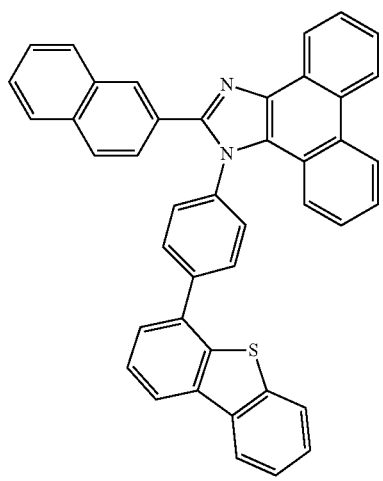
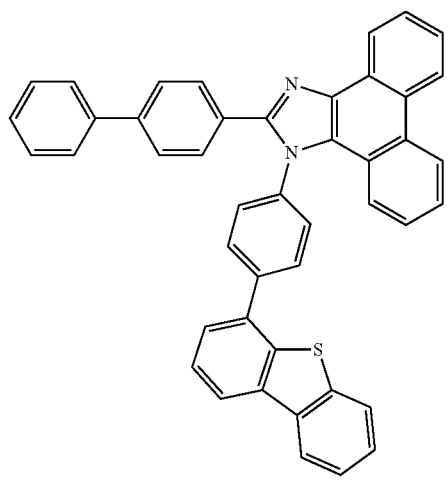
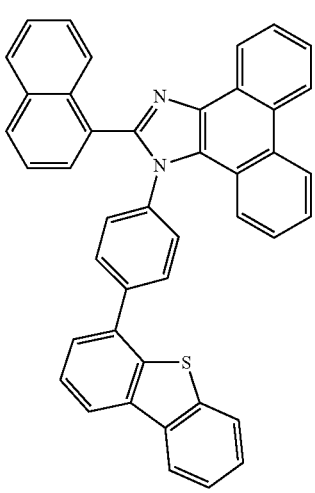

-continued
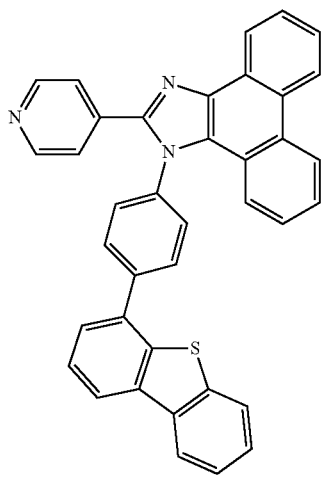
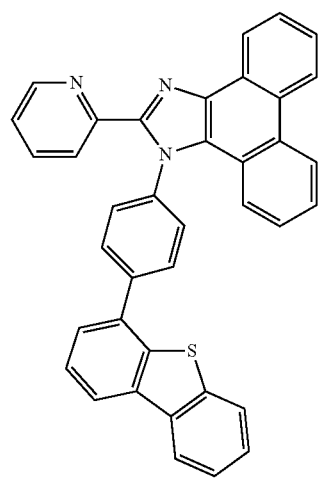
-continued
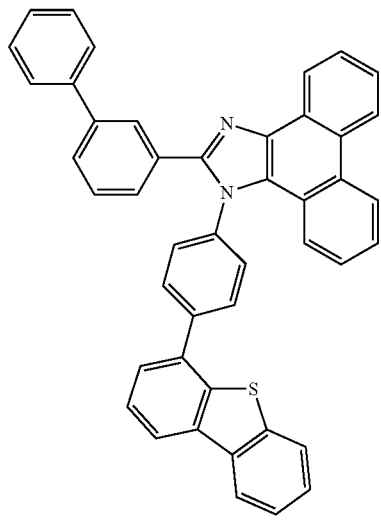
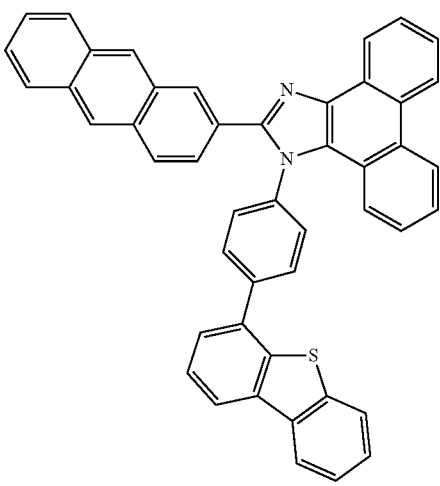
(Compound 20)
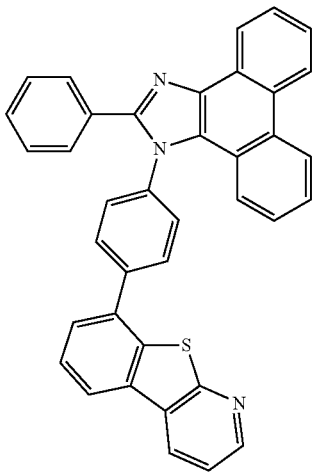

-continued
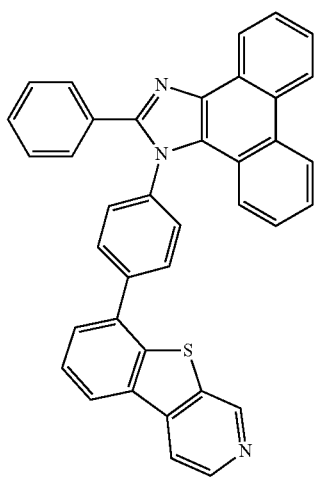
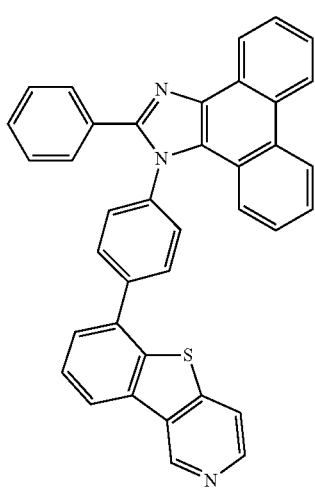
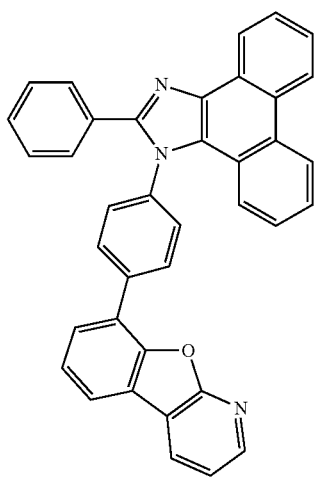
-continued
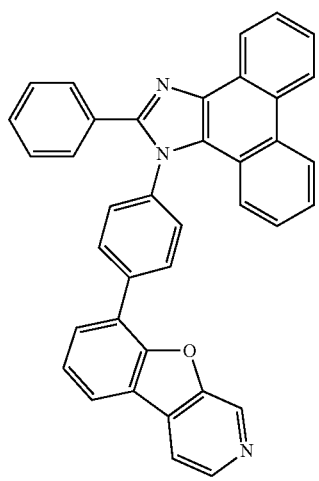
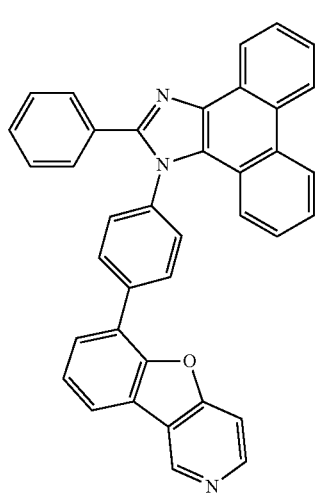
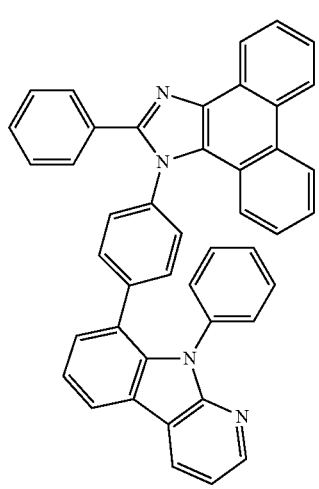

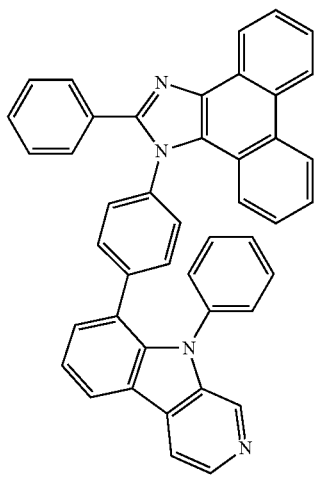
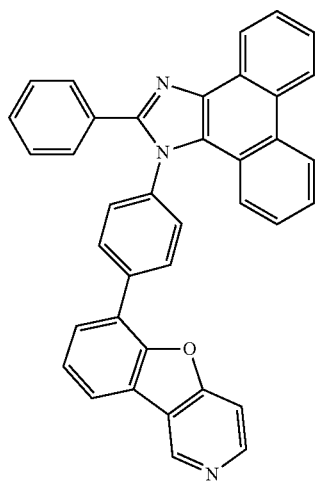
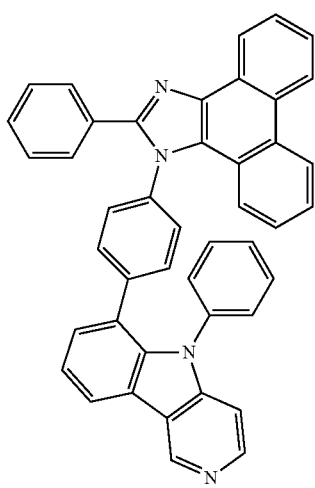
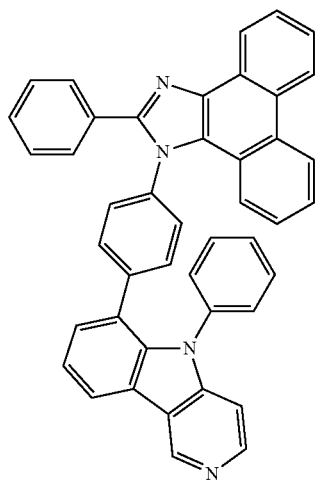
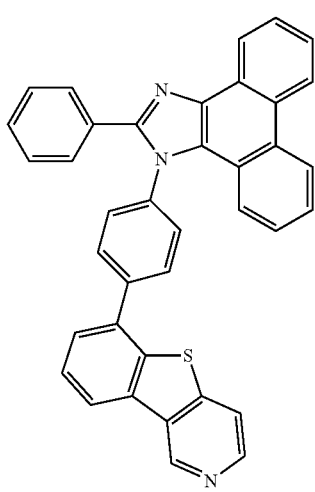
(Compound 21)
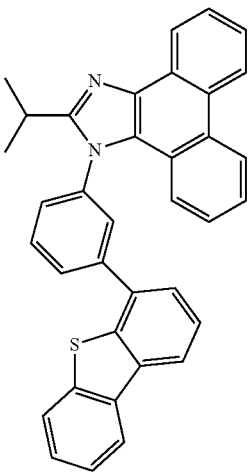

47
-continued
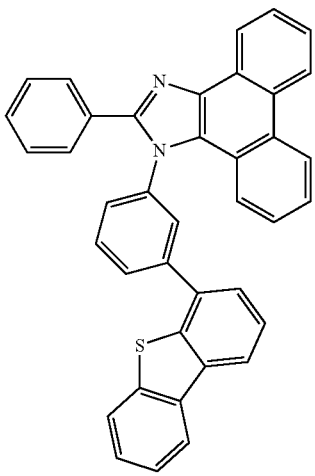
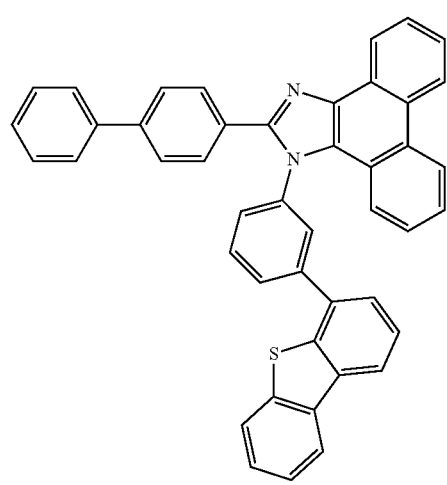
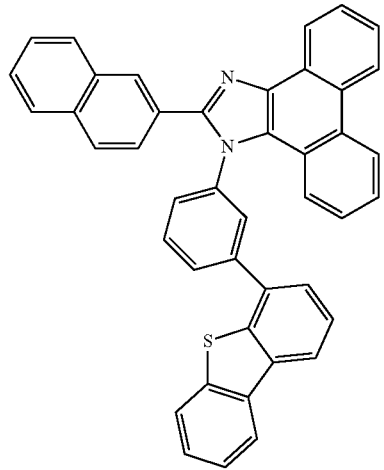
48
-continued
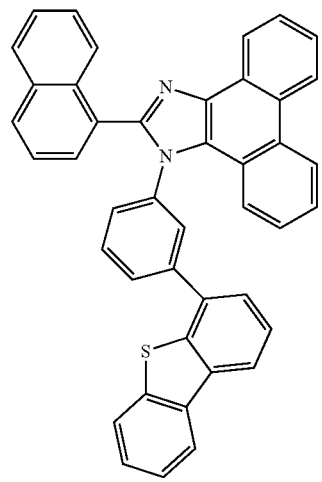
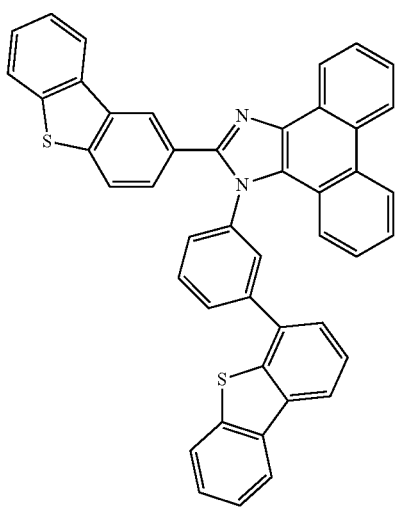
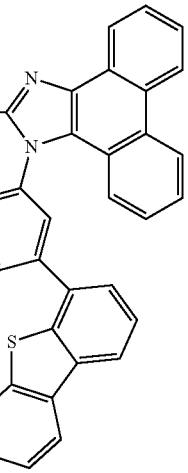

-continued
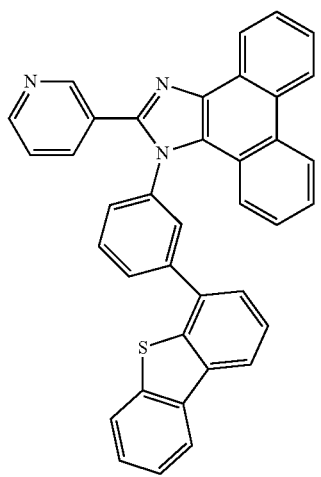
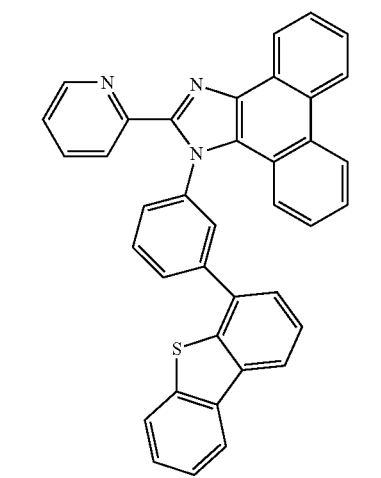
-continued
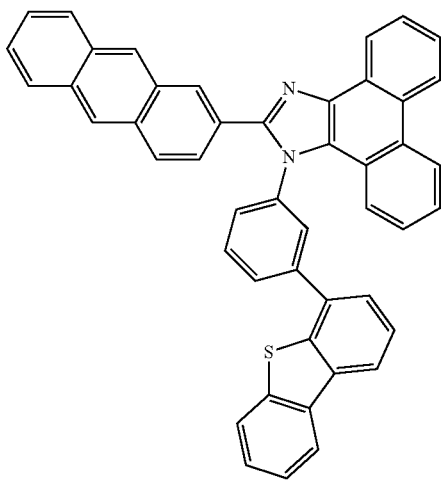
(Compound 22)
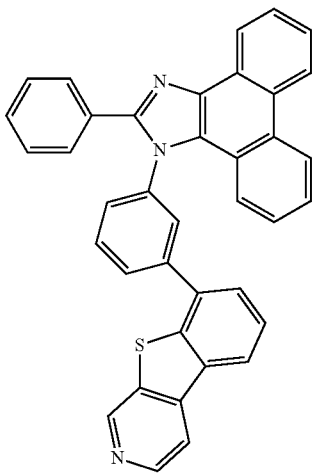

51
-continued
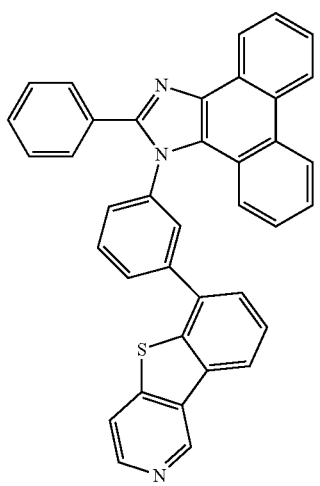
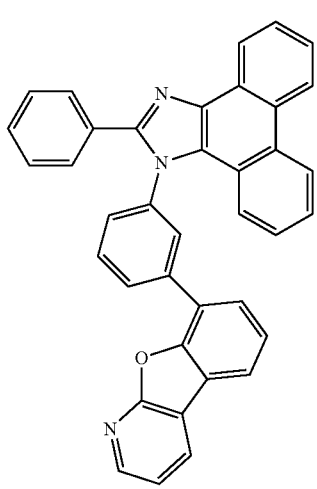
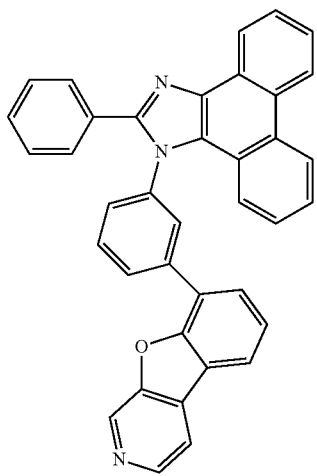
52
-continued
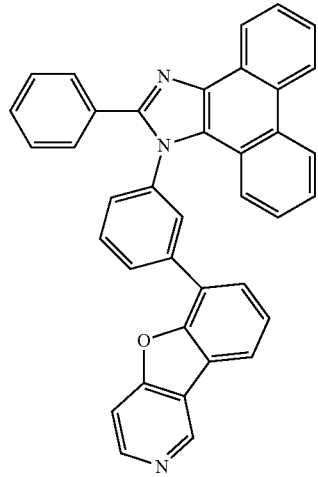
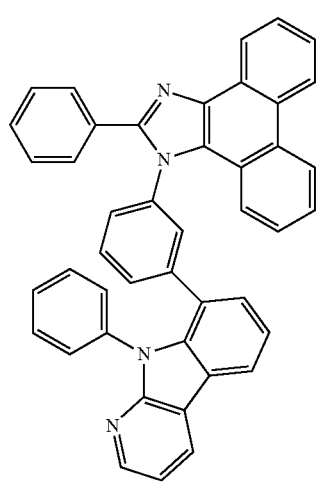
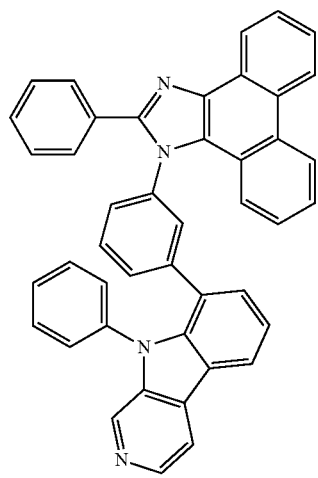

53
-continued
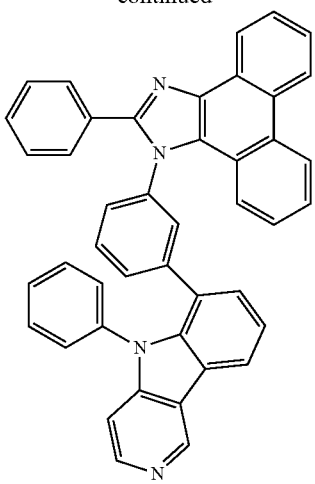
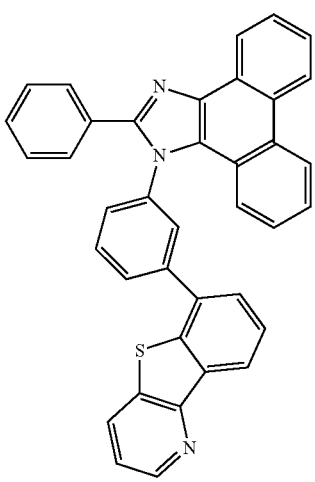
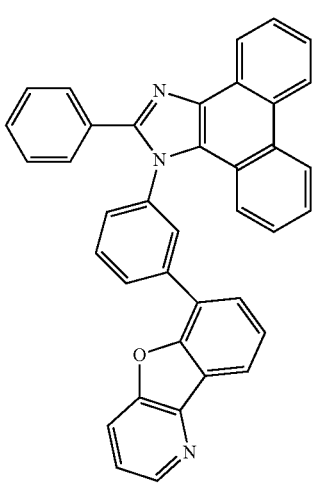
54
-continued
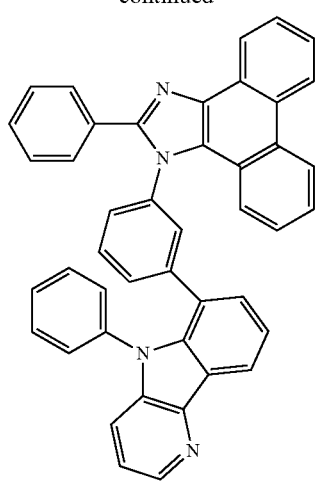
(Compound 23)
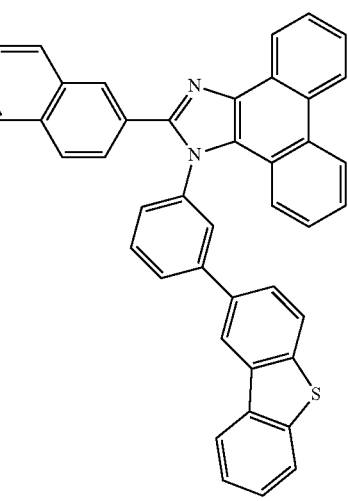

-continued
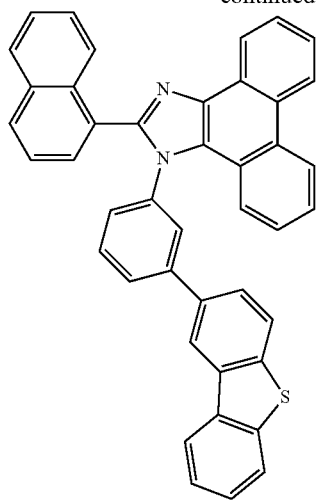
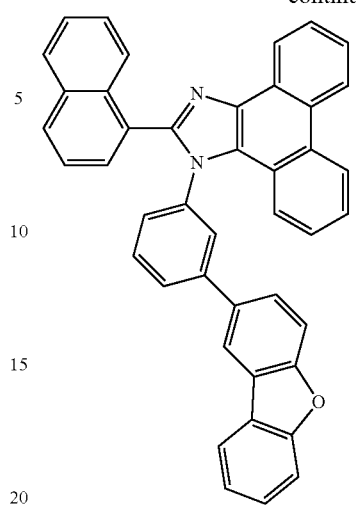
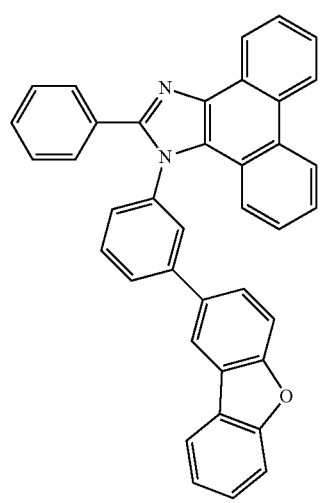
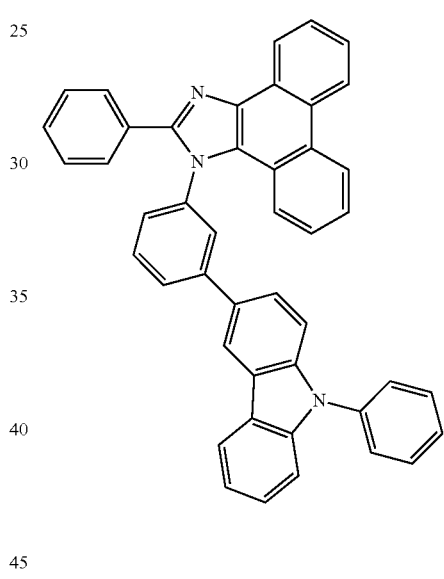
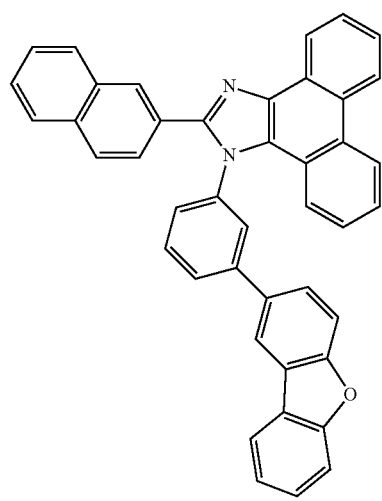
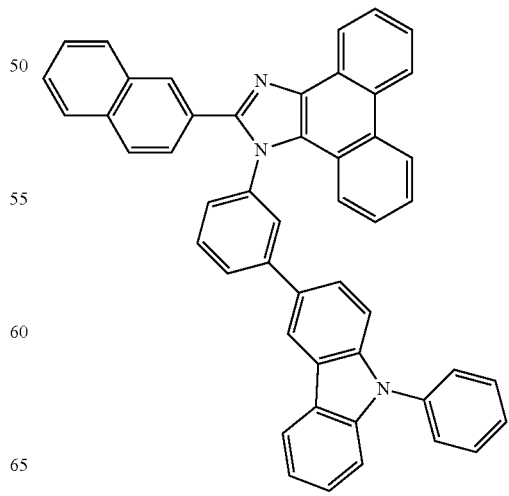

57
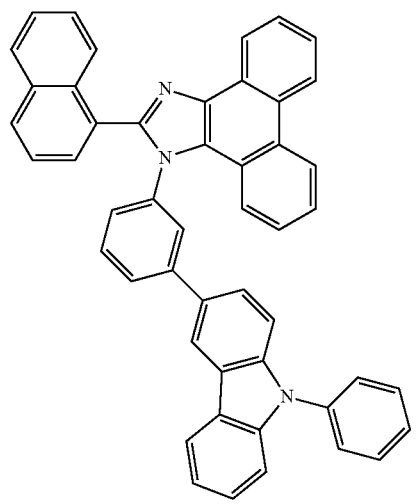
58
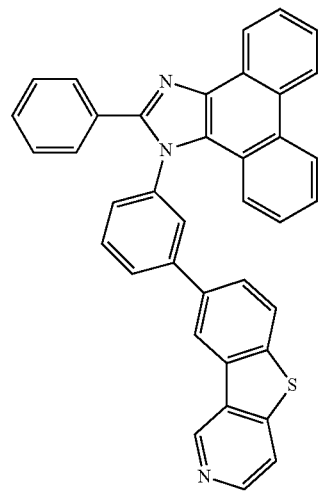
(Compound 24)
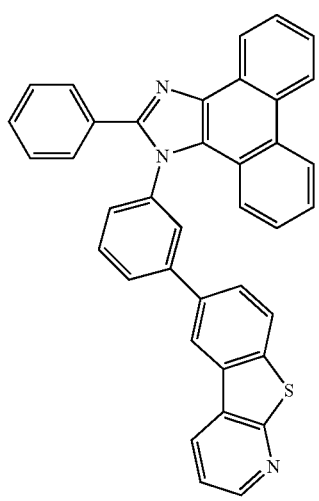
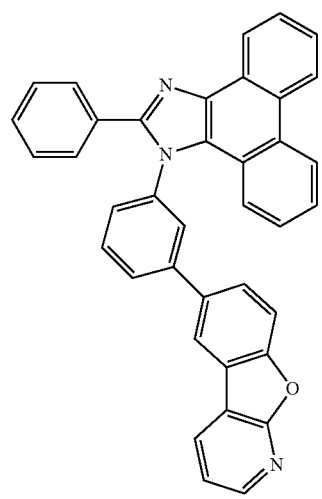
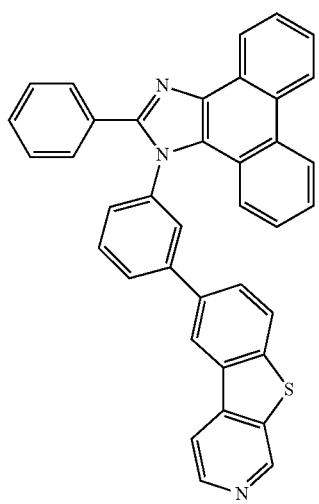
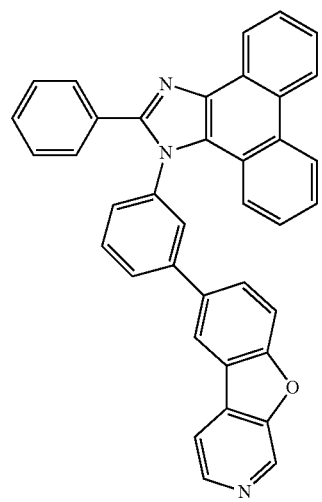

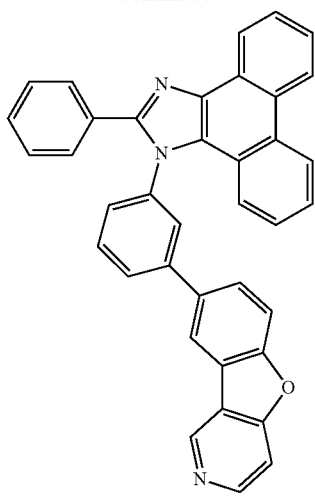
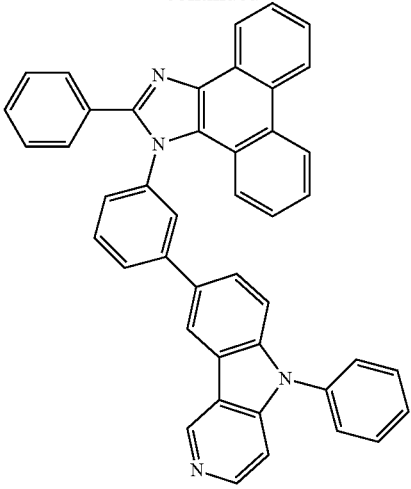
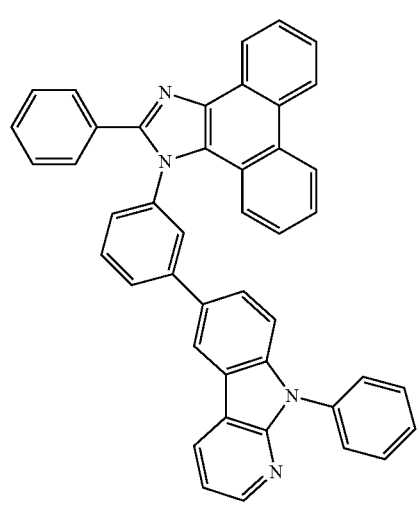
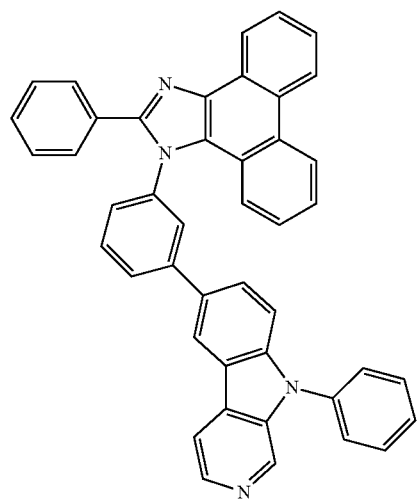
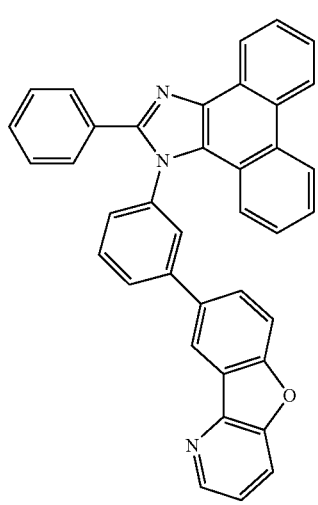

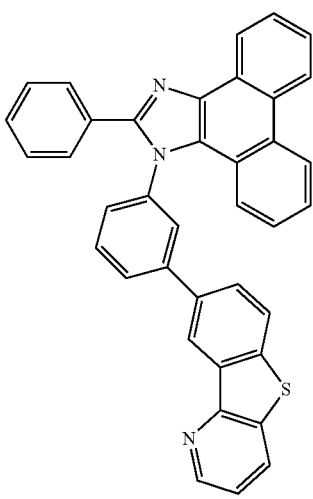
(Compound 25)
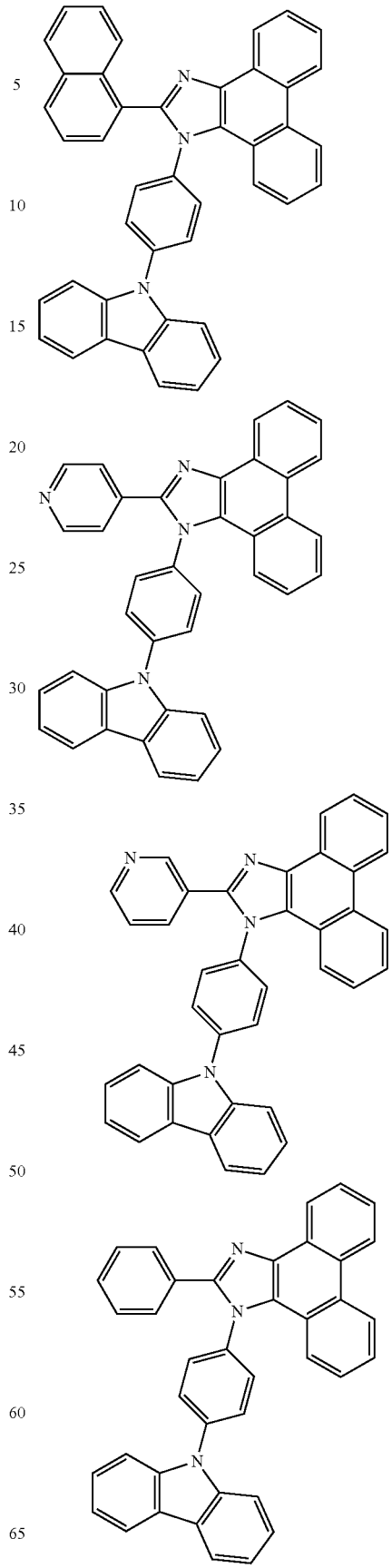

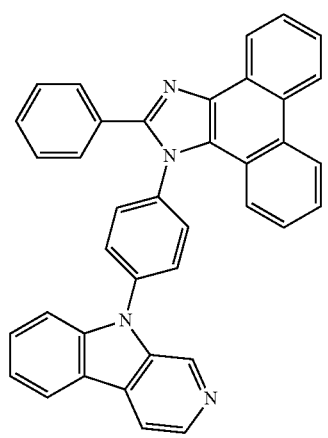
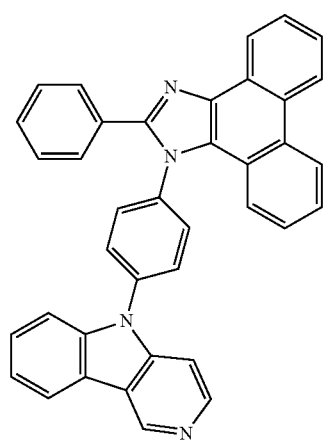
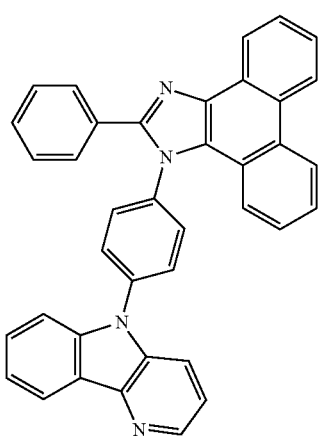 [SMILES: c1ccc(-c2nc3c4ccccc4c4ccccc4c3n2-c2ccc(-n3c4ccccc4c4ncccc43)cc2)cc1]
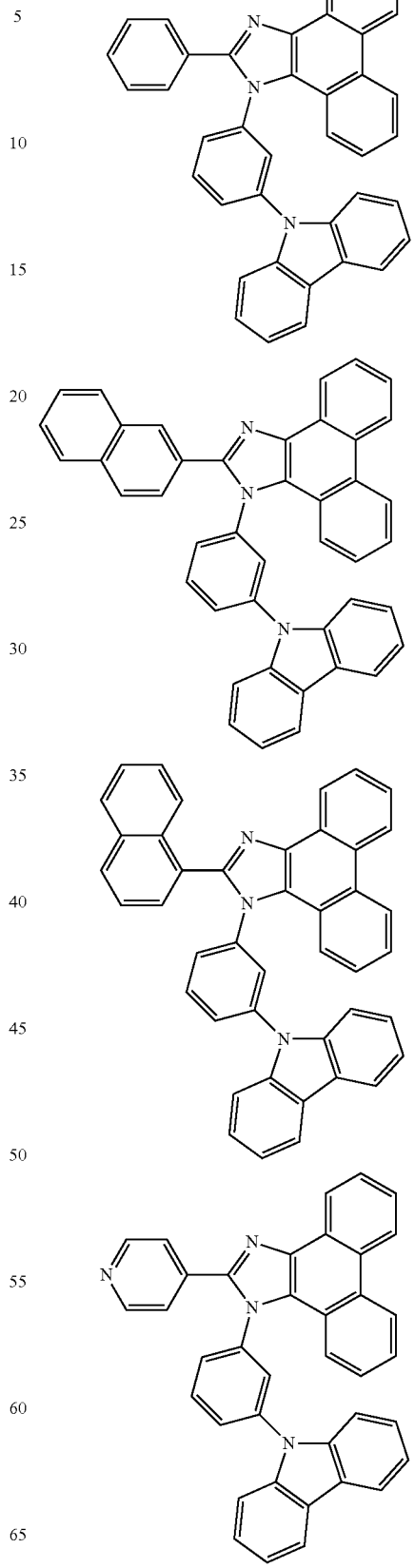
(Compound 26)

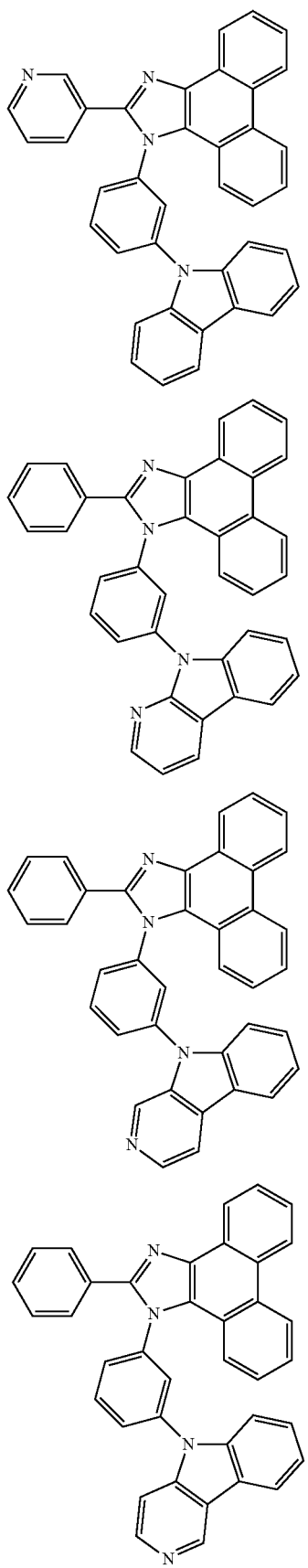
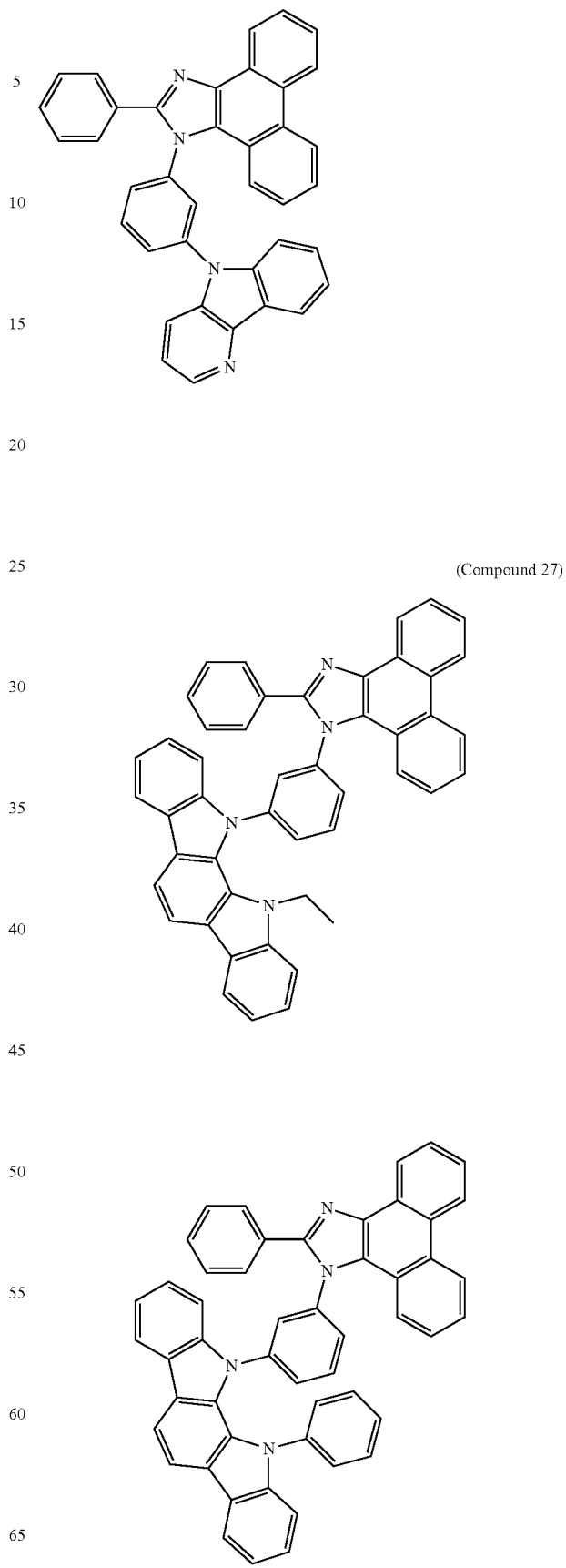
(Compound 27)

67
-continued
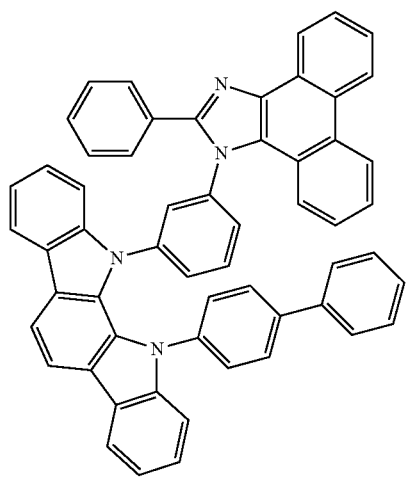
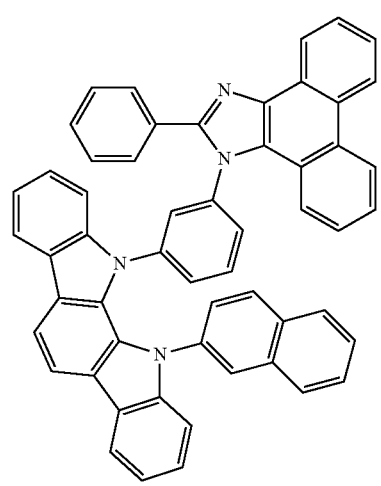
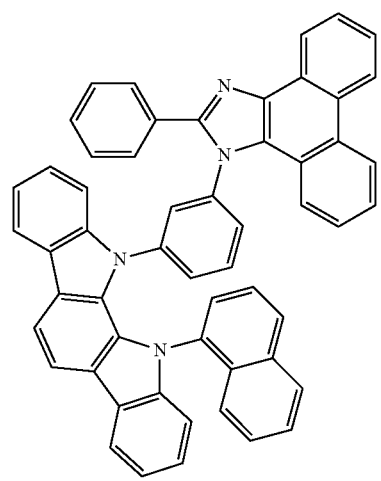
68
-continued
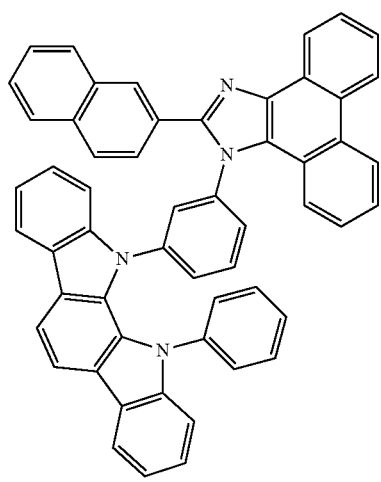
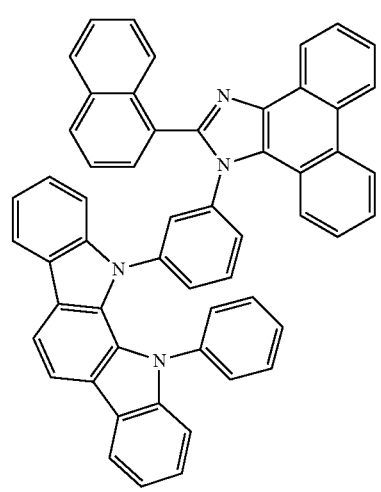
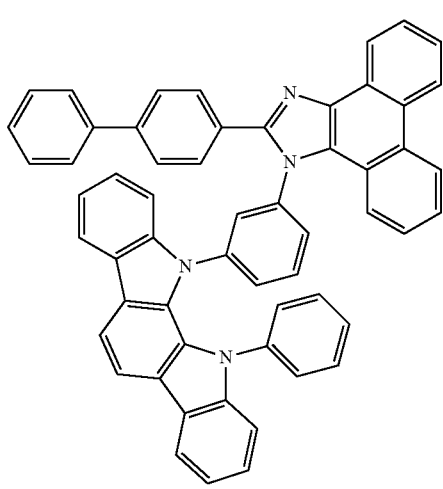

69
-continued
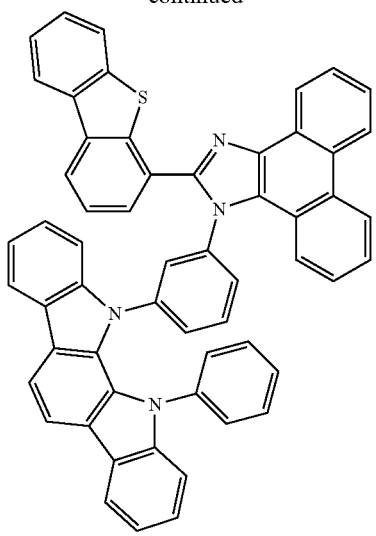
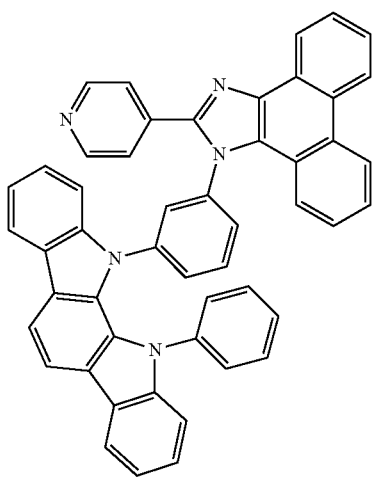
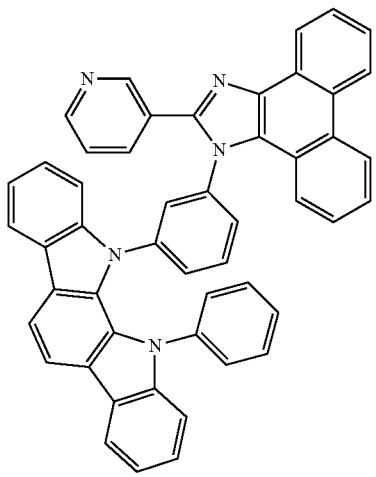
70
-continued
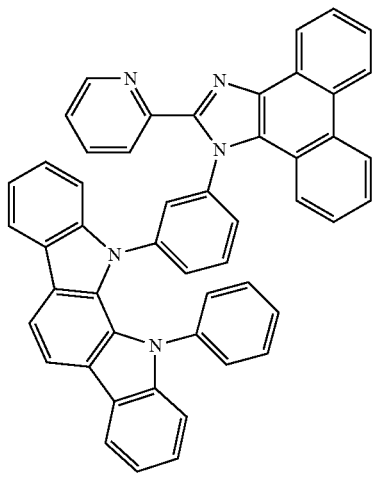
(Compound 28)
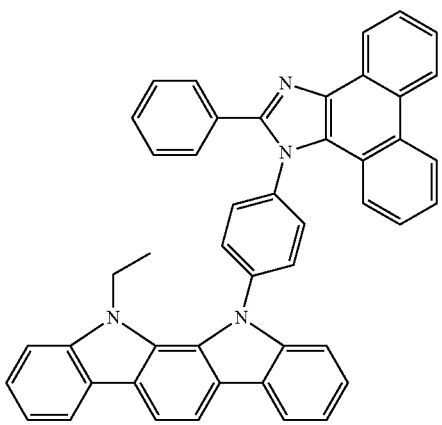
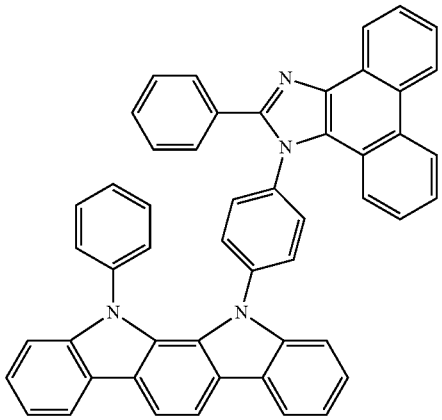

71
-continued
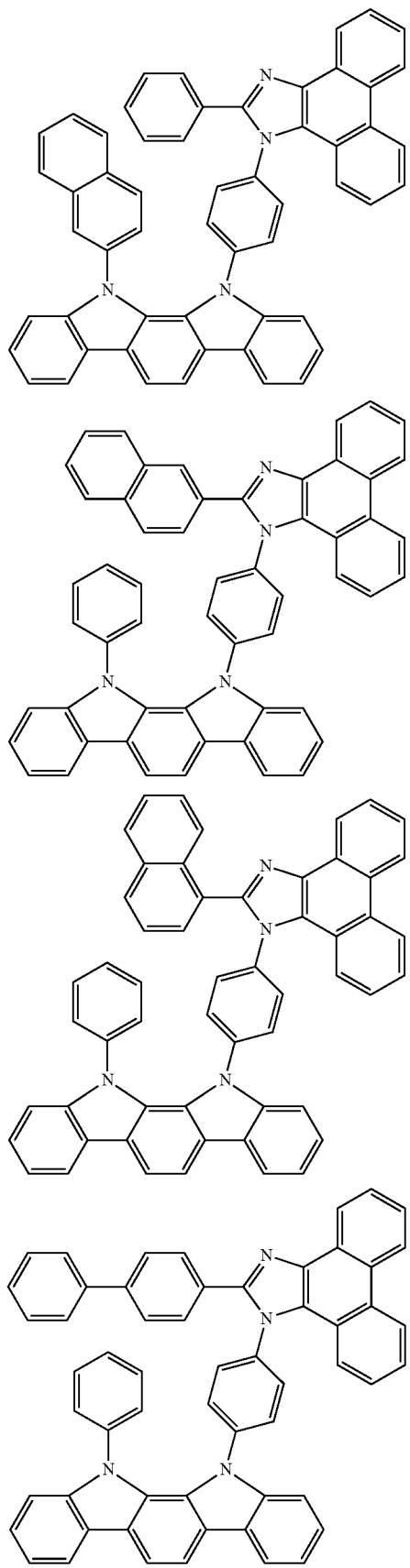
72
-continued
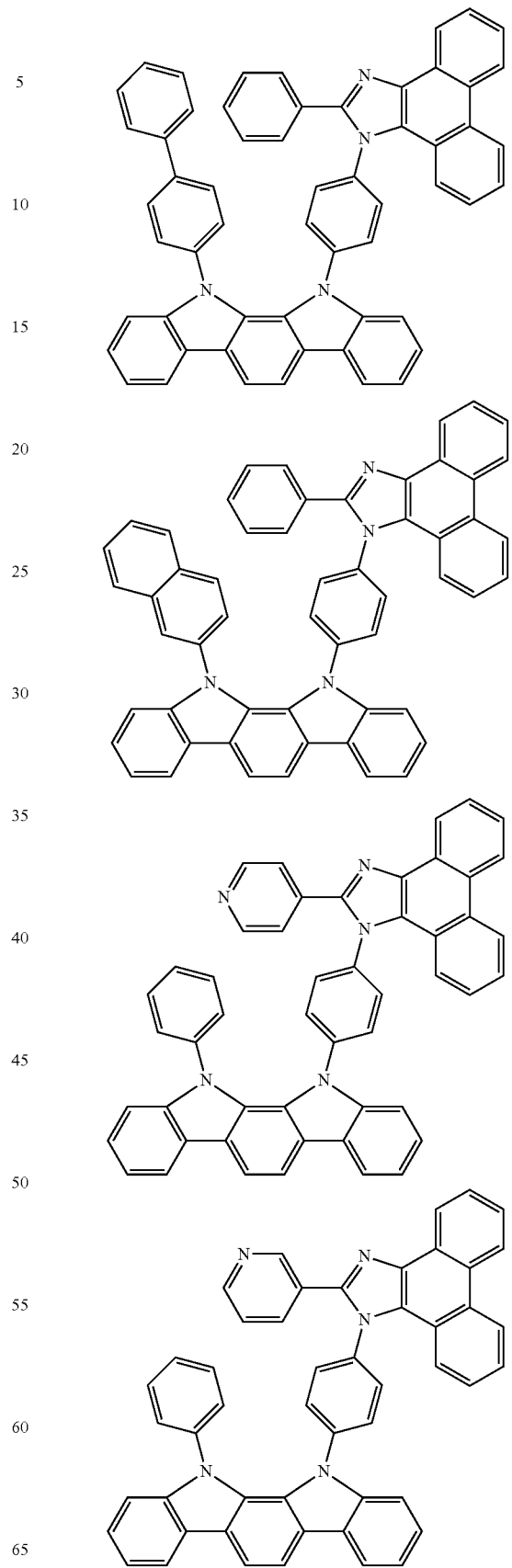

73
-continued
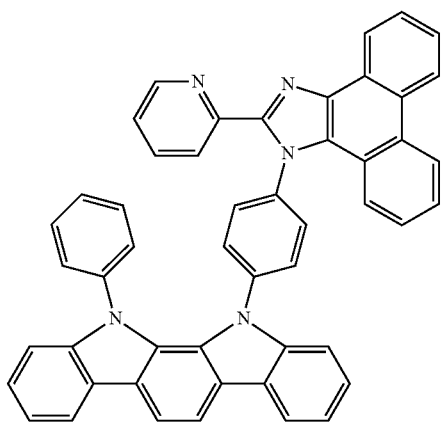
(Compound 29)
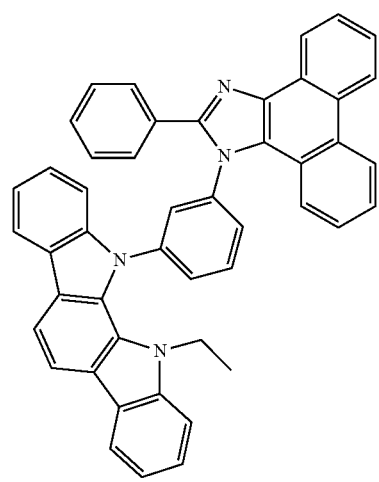
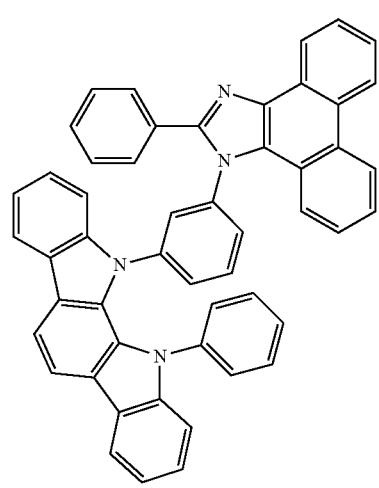
74
-continued
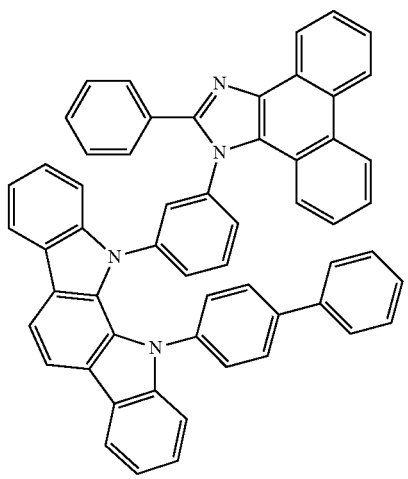
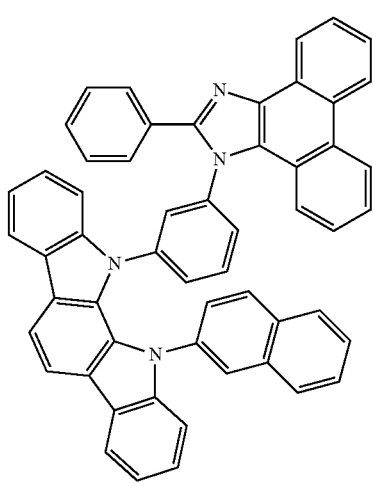
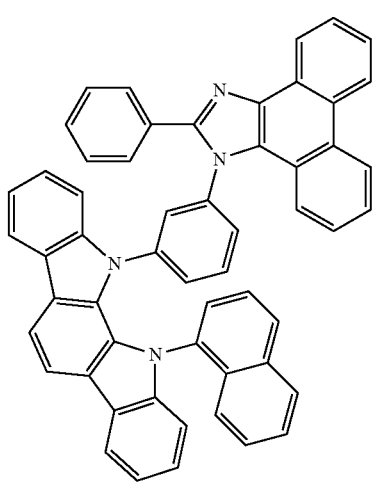

75
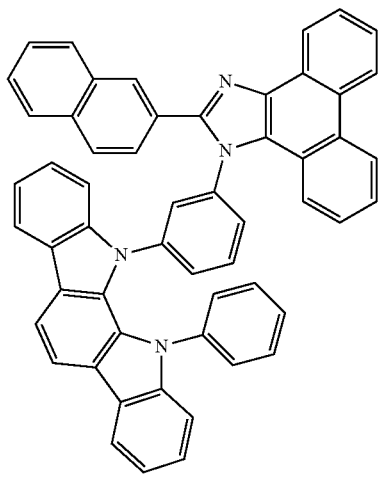
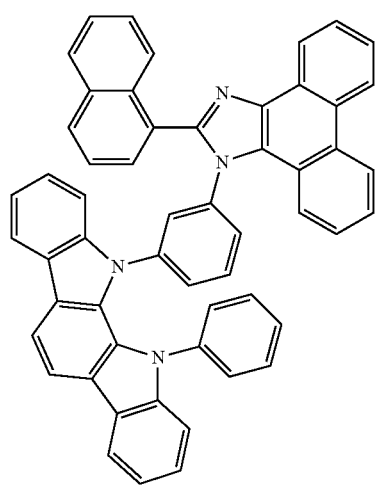
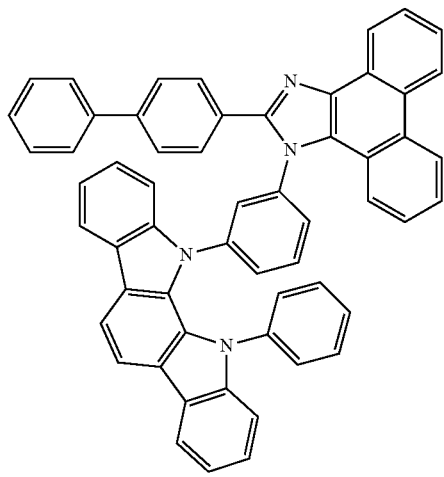
76
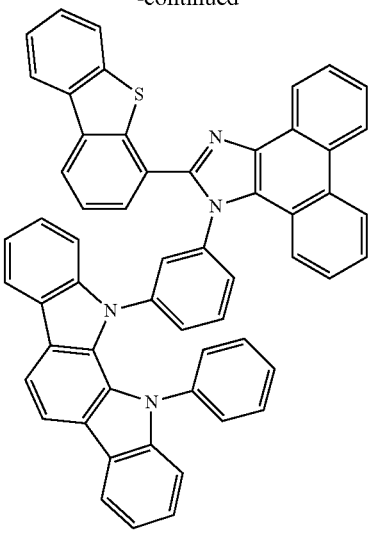
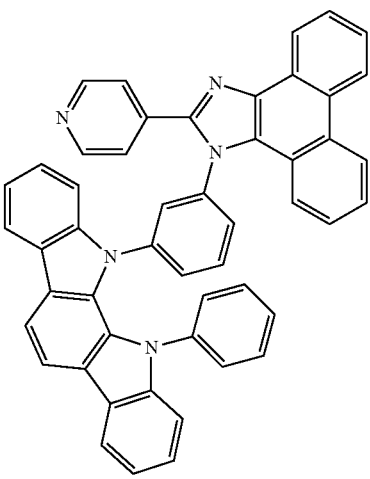
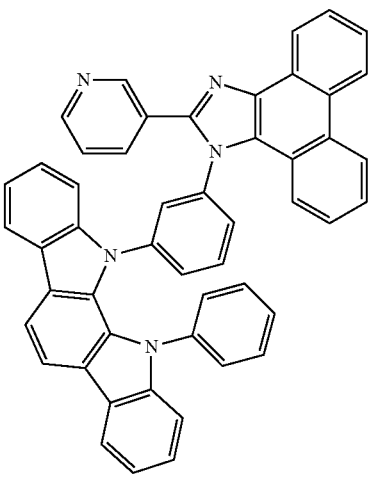

77
-continued
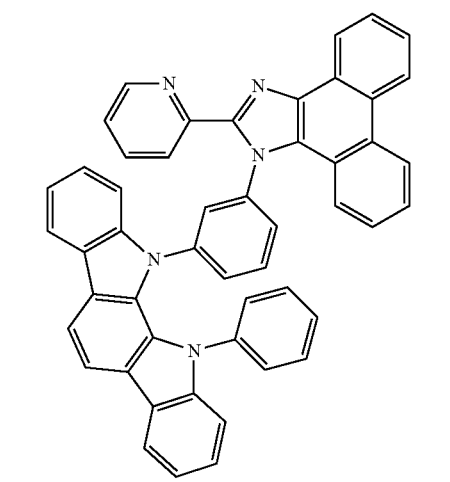
(Compound 30)
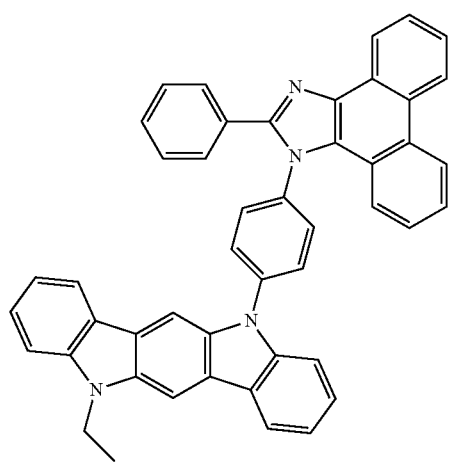
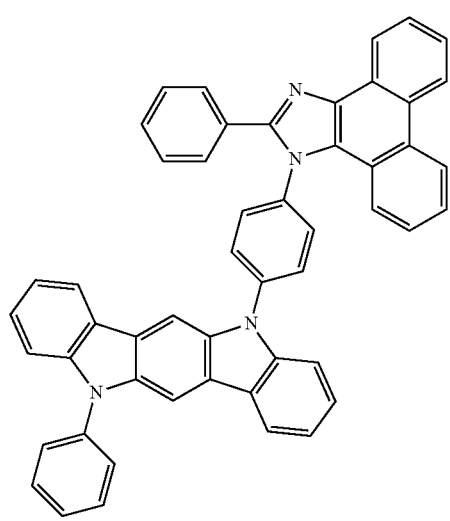
78
-continued
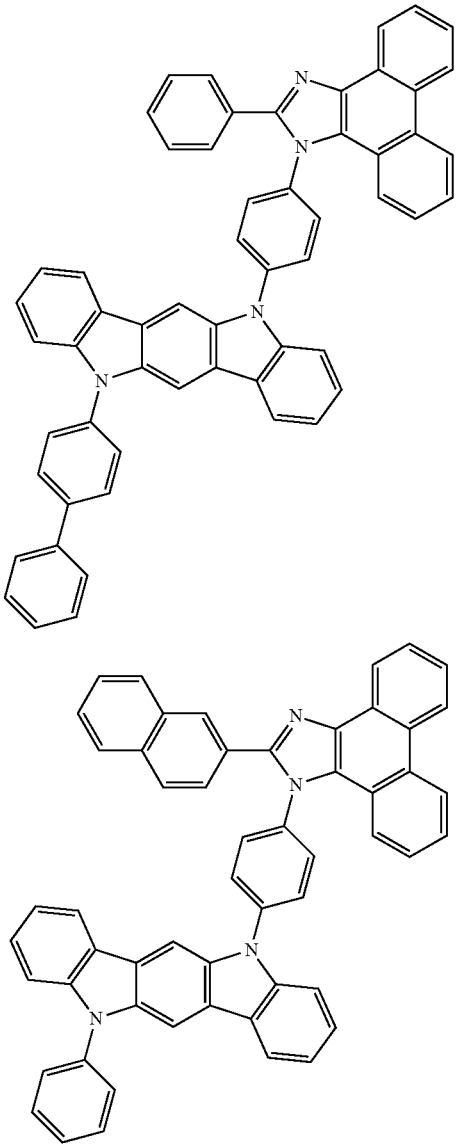
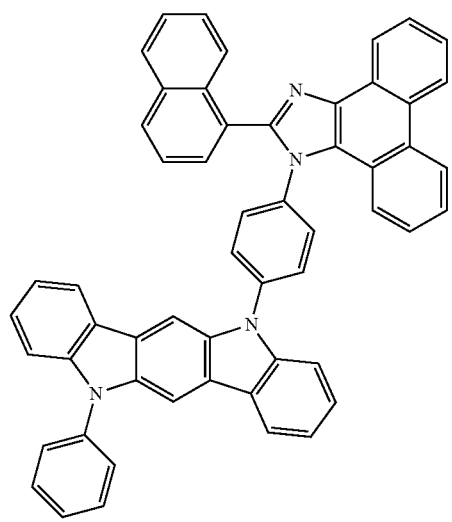

79
-continued
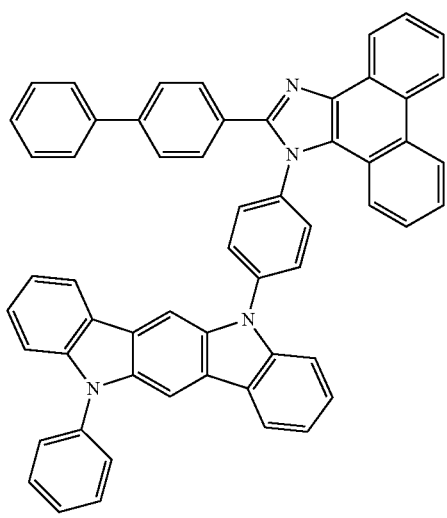
80
-continued
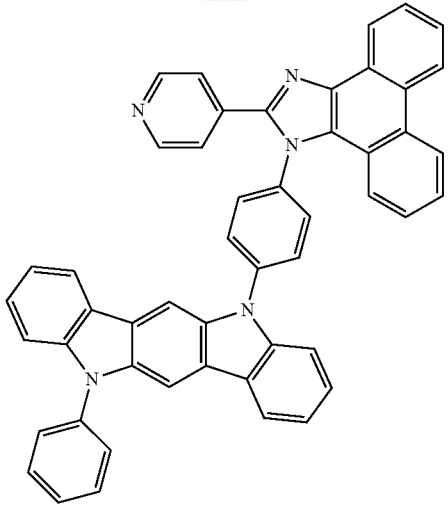
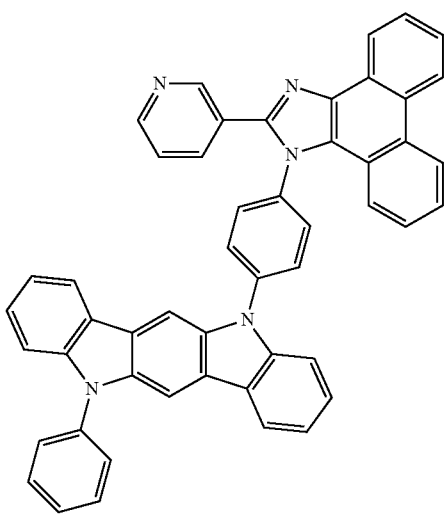
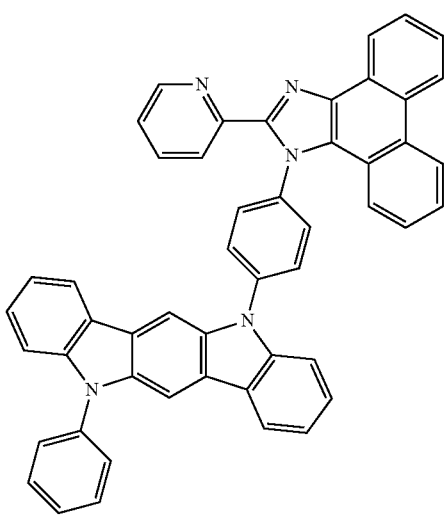

(Compound 31)
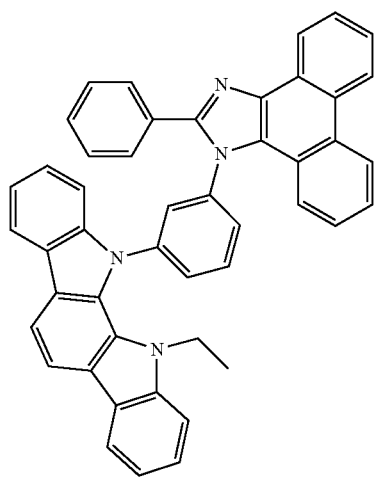
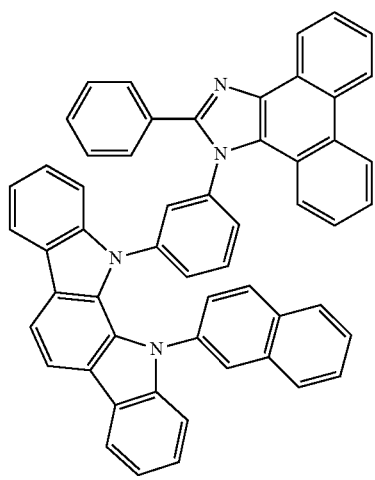
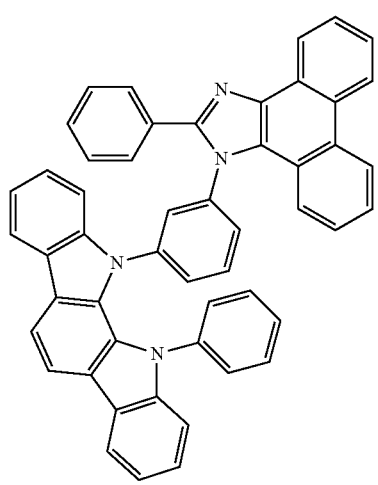
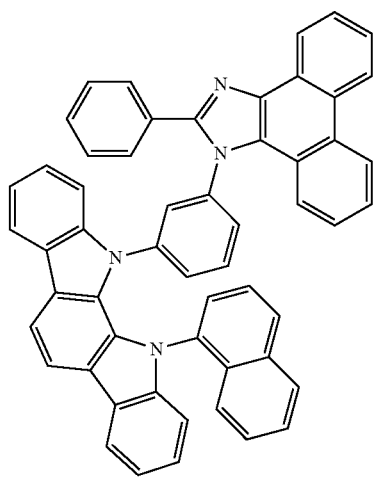
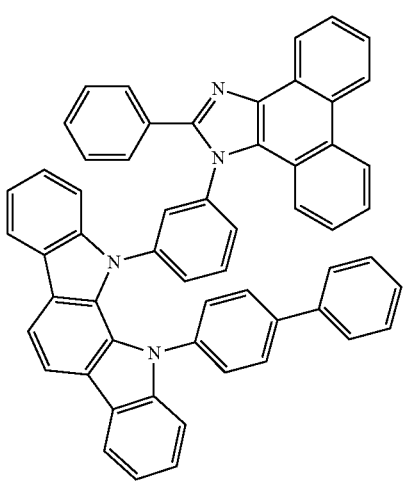
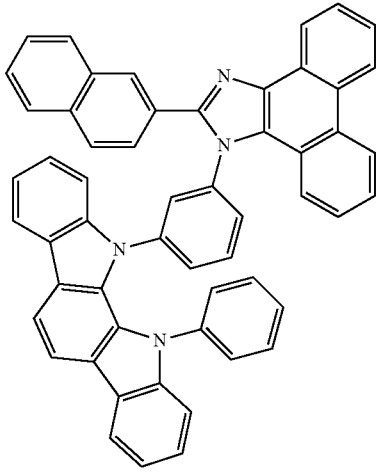

-continued

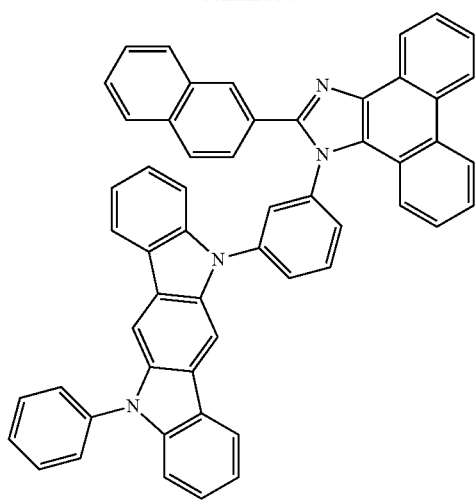

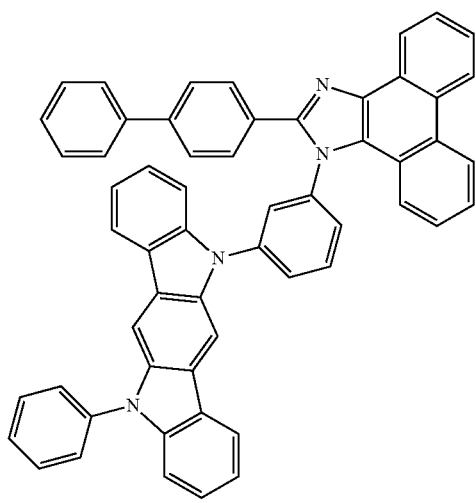

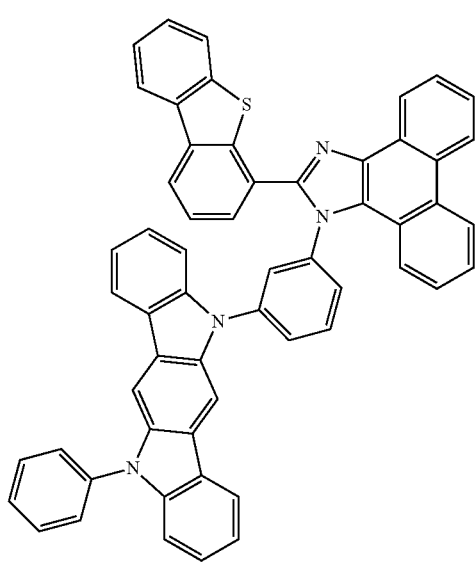

-continued

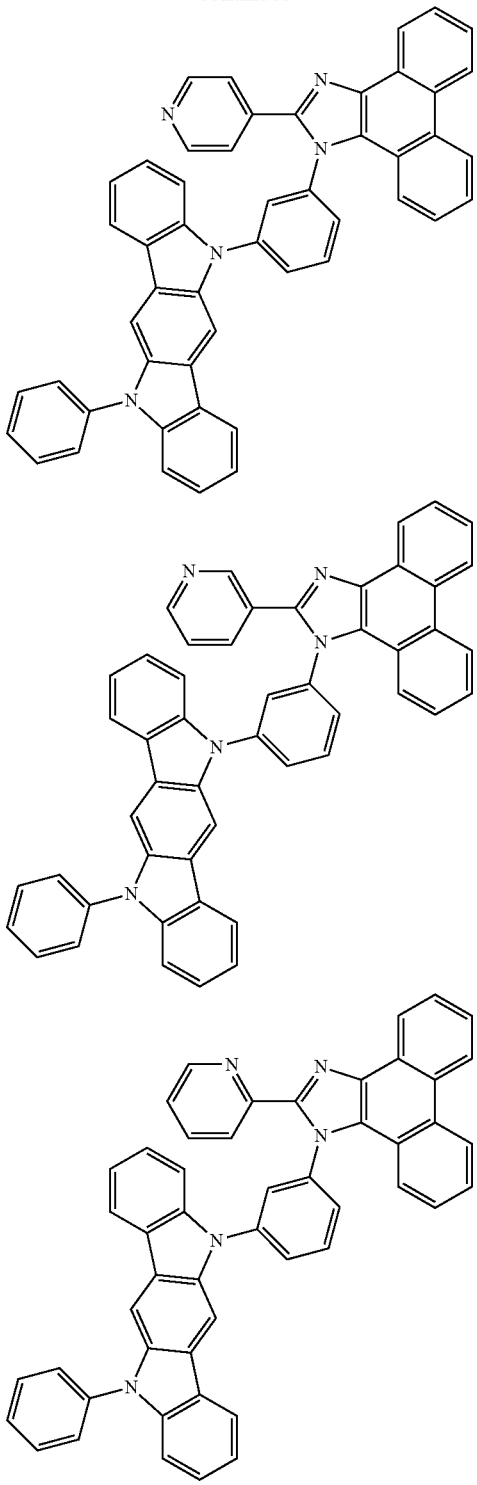

The general manufacturing method of the prior art as described in J. Org. Chem, 1937, 2, 319 may be used to manufacture the imidazole compound represented by the formula (1). Furthermore, regarding a substituent of the imidazole compound, well known reaction methods, such as Suzuki coupling and Sonogashira coupling, may be incorporated into the manufacturing method.

The imidazole compound of the present invention may serve as material for electronic device use, with application in electroluminescent devices, organic thin-film solar cells, and the like. More specifically, the imidazole compound of the present invention may be used in light-emitting diodes for use in organic electroluminescent displays, organic electroluminescent lighting, and the like, as well as having application as a host material contained in luminous layers of electroluminescent devices.

The material for electronic device use of the present invention normally contains 1~100 percentage by weight of the imidazole compound of the present invention. And, may also contain well known solvents, other luminescent materials, other host materials, and additive agents within a range of 0~99 percentage by weight according to purpose.

An electronic device of the present invention comprises an electroluminescent device, with the electroluminescent device provided with a positive electrode and a negative electrode and a luminous layer placed between the two electrodes. An example of the aforesaid electroluminescent device is an organic electroluminescent device. In the organic electroluminescent device, holes from the anode and electrons from the cathode are injected into the luminous layer. And the recombination of the electrons and the holes within the luminous layer is used to produce excitons. Because luminescence occurs when these excitons release their energy, thus, the organic electroluminescent device may be applied in electronic devices such as luminescent sources, lighting devices, and display devices.

In addition, materials for the cathode, the anode, and other materials of the luminous layer used to construct the organic electroluminescent device may use materials appropriately selected from the prior art. Moreover, an electron transport layer including electron transfer material may be disposed between the cathode and the luminous layer of the aforementioned electroluminescent device. Furthermore, a hole transfer layer including hole transfer material may also be disposed between the anode and the organic thin layer. The electron transport material or the hole transport material may use materials appropriately selected from materials of the prior art.

The imidazole compound of the present invention may serve as luminescent material (doping material) containing a luminous layer or applied in host material for electronic device use.

Regarding the luminous layer composed of two or more compounds, a luminescent material occupies a minimum in the mixing ratio (mass ratio), whereas a host material occupies a maximum in the mixing ratio (mass ratio). For example, if the luminous layer is composed of a compound A and a compound B, and the mixing ratio of A:B=10:90, then compound A is a luminescent material compound and compound B is a main illuminant compound. And if the luminous layer is composed of compound A, compound B, and compound C, and the mixing ratio of A:B:C=5:10:85, then compound A is a luminescent material compound, and compound C is a main illuminant compound, When the imidazole compound of the present invention is used in a luminescent material, then it also serves as a carrier transport and injection material, and a carrier blocking material, and may be used in a hole transport material or an electron transport material.

In addition, because the material for electronic device use contains the imidazole compound of the present invention, thus, coating methods, such as solution coating and material-dissolved coating, may be used to form an electroluminescent device on a substrate using a thin film manufacturing process.

For example: the material for electronic device use of the present invention is used to form a luminous layer for electroluminescent devices, with concrete examples including a method for solution coating of the material for electronic device use on a substrate, a method for forming an evaporated film of the material for electronic device use on a substrate, and a method for material-dissolved coating the material for electronic device use on a substrate.

Examples of the substrate include conventional substrates generally used in electronic devices, such as glass, crystal. sapphire, silicon, carborundum, polyethylene naphthalate, polyethylene terephthalate, polyether sulphone, polyimide, polyaramide, cycloolefin polymer, and polycarbonate. The substrate may also be a transparent conducting layer of ITO (indium tin oxide), Examples of solution coating methods of the material for electronic device use of the present invention on a substrate include spin coating method, flow casting method, ink-jet method, and printing method. Examples of the solvent used in the solution coating of the material for electronic device use include aromatic compounds of toluene, xylene; halogen-containing solvents of 1,2-dichloroethane, chloroalkanes; ether solvents of dimethoxyethane; aliphatic esters of ethyl acetate; ketone solvents of acetone, butanone; amide solvents of N,N-dimethylformamide; and dimethyl sulfoxide. One type of any of the above compounds may be singly used or two and above of the above compounds may be used.

After a solution coating of the material for electronic device use is applied to the substrate or other layer, according to requirements, heat drying or reduced pressure drying is carried out to remove the solvent, and thereby enable a luminous layer to form a film, Examples of methods to apply an evaporated film of the material for electronic device use of the present invention on a substrate include using the evaporated film method of the prior art of Sigma-Aldrich as recorded in Vol. 1, No. 1 of "Fundamentals of Materials Science."

Examples of methods for material-dissolved coating of the material for electronic device use of the present invention on a substrate include using a general material-dissolved coating method.

EMBODIMENTS

Melting point (mp), infrared spectroscopy (IR), nuclear magnetic resonance ($^1$HNMR (hydrogen NMR), $^{13}$CNMR (carbon NMR)), matrix-assisted laser desorption ionization time-of-flight mass spectrometry (MALDI-TOF-MS) are respectively used for additional identification of the compounds obtained from the embodiments.

The analysis and conditions used by the embodiments are recorded in the description of the embodiments.

Reference Example 1

Synthesis of 1-(3-bromo-phenyl)-2-phenyl-1H-phenanthro-[9,10-d]imidazole

Add acetic acid (300 ml) to a mixture of benzaldehyde (32.0 g) and 3-bromaniline (51.8 g), and after heating under reflux for 1 hour, add 9,10-phenanthrenequinone (62.7 g) and ammonium acetate (23.3 g), After a further heating under reflux for 3 hours, cool the reaction mixture until it is at room-temperature, then add methanol (3 L) and cool the mixture down using an ice-bath. Leave standing for 2 hours, and then filter out the colored solid produced. Use methanol (200 ml) to wash the colored solid to obtain a brown colored solid of 1-(3-bromo-phenyl)-2-phenyl-1H-phenanthro-[9,10-d] imidazole (82.0 g, 61% yield), (Compound 32)

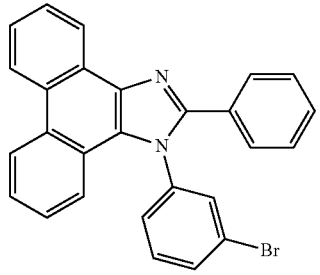

Reference Example 2

Synthesis of 1-(3-bromo-phenyl)-2-(2-naphthyl group)-1H-phenanthro-[9,10-d] imidazole Add acetic acid (30 ml) to a mixture of 2-naphylaldehyde (4.5 g) and bromaniline (5.0 g), and after heating under reflux for 2 hours, add 9,10-phenanthrenequinone (6.0 g) and ammonium acetate (2.2 g). After a further heating under reflux for 6 hours, cool the reaction mixture until it is at room-temperature. Add methanol (300 L) and cool the mixture down using an ice-bath. Leave standing for 2 hours, then filter out the solid and wash with methanol to obtain a brown colored solid of 1-(3-bromo-phenyl)-2-(2-naphthyl group)-1H-phenanthro-[9,10-d]imidazole (10.0 g, 69% yield), (Compound 33)

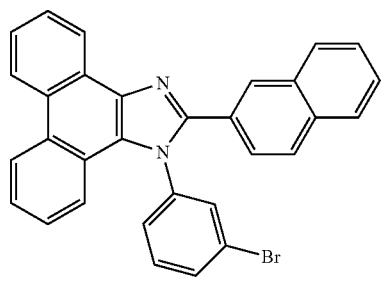

Reference Example 3

Synthesis of 2-(3-nitrophenyl)-4,6-diphenyl-1,3,5-triazine

In a nitrogen atmosphere, add degassed toluene (80 ml), methanol (40 ml) and 2M (mol) sodium carbonate aqueous solution (80 ml) to a mixture of 2-chloro-4,6,-diphenyl-1,3,5-triazine (12.2 g), 3-nitrobenzeneboronic acid (4.0 g) and tetrakis(triphenylphosphine) palladium (0) (0.56 g). After heating under reflux for 4 hours, cool the reaction mixture until it is at room-temperature, then filter out the solid and wash with methanol to obtain a white colored solid of 2-(3-nitrophenyl)-4,6-diphenyl-1,3,5-triazine (7.6 g, 88% yield), (Compound 34)

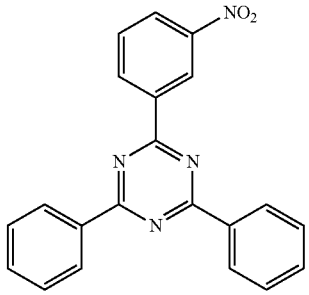

Reference Example 4

Synthesis of 3-(4,6-diphenyl-1,3,5-triazine-2-yl)aniline

Add a mixture of 2-(3-nitrophenyl)-4,6-diphenyl-1,3,5-triazine (8.0 g), 5% palladium supporter—activated carbon (containing 50% water) (5.1 g) and tetrahydrofuran (THF) (240 ml) to a pressure cooker, and in the initial stage, carry out a hydrogen addition reaction for 4 hours under 1 Mpa (megapascal) of hydrogen pressure at 25° C., followed by filtration to obtain a reaction solution. Then concentrate and dry the filtered solution to obtain a yellow colored solid of 3-(4,6-diphenyl-1,3,5-triazine-2-yl)aniline (7.3 g, 99% yield), (Compound 35)

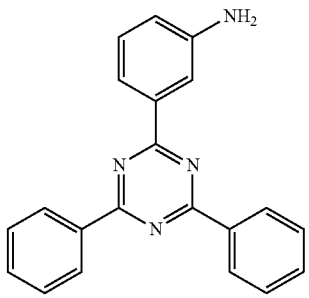

Embodiment 1

Add degassed toluene (160 ml), methanol (80 ml) and 2M sodium carbonate aqueous solution (160 ml) to a mixture of 1-(4-dibenzothiophene-3-yl-phenyl)-2-phenyl-1H-phenanthro-[9,10-d]imidazole (20.0 g), 4-dibenzothiophene boronic acid (11.2 g) and tetrakis(triphenylphosphine) palladium (0) (1.0 g). After heating under reflux for 6 hours, cool the reaction mixture until it is at room-temperature, then filter out the solid, and use toluene to carry out recrystallization to obtain a white colored solid of 1-(4-dibenzothiophene-3-yl-phenyl)-2-phenyl-1H-phenanthro-[9,10-d]imidazole (10.5 g, 43% yield), (Compound 36)

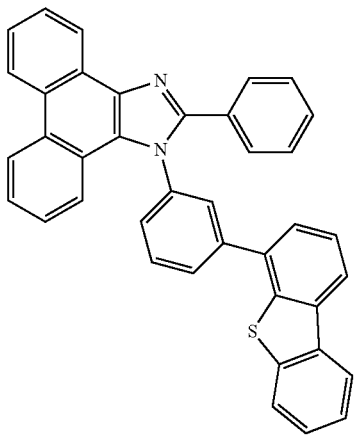

Colorless powder; mp (melting point) 238° C.

$^1$H NMR (400 MHz, THF-d$_8$) δ7.36 (dd, J=8.2, 1.0 Hz, 1H), 7.41-7.45 (m, 4H), 7.50-7.52 (m, 2H), 7.57-7.62 (m, 3H), 7.68-7.72 (m, 3H), 7.77-7.94 (m, 4H), 8.02-8.05 (m, 2H), 8.36-8.39 (m, 2H), 8.72 (dd, J=9.2, 1.2 Hz, 1H), 8.89 (d, J=8.4 Hz, 1H), 8.95 (d, J=8.4 Hz, 1H), $^{13}$C NMR (100 MHz, CDCl$_3$) δ120.9, 122.2, 122.5, 122.8, 123.0, 123.2, 124.2, 125.0, 125.4, 125.8, 126.1, 126.2, 127.2, 127.6, 127.8, 128.0, 128.2, 128.2, 128.8, 129.0, 129.3, 129.6, 129.9, 130.2, 130.8, 131.5, 135.1, 135.6, 136.4, 137.1, 138.0, 138.8, 139.1, 142.2, 151.3.

MALDI-TOF-MS (positive, Dithranol) m/z: calcd. for C$_{39}$H$_{24}$N$_2$S; 552 (M+). found: 553 ([M+H]$^+$).

Embodiment 2

Synthesis of 1-(9-phenylcarbazolyl-3-yl-phenyl)-2-phenyl-1H-phenanthro-[9,10-d]imidazole In a nitrogen atmosphere, add degassed toluene (140 ml), methanol (70 ml), and 2M (mol) sodium carbonate aqueous solution (140 ml) to a mixture of 1-(3-bromophenyl)-2-phenyl-1H-phenanthro-[9,10-d]imidazole (20.0 g) obtained from Reference Example 1, 9-phenylcarbazole-3-boronic acid (14.0 g) and tetrakis(triphenylphosphine) palladium (0) (1.1 g). After heating under reflux for 6 hours, cool the reaction mixture until it is at room-temperature, then filter out the solid. After using tetrahydrofuran (300 ml) to heat and dissolve the solid obtained, and while ice cooling, add methanol (300 ml), then filter out a crystal to obtain a white colored solid of 1-(9-phenylcarbazole-3-yl-phenyl)-2-phenyl-1H-phenanthro-[9,10-d]imidazole (12.1 g, 44% yield), (Compound 37)

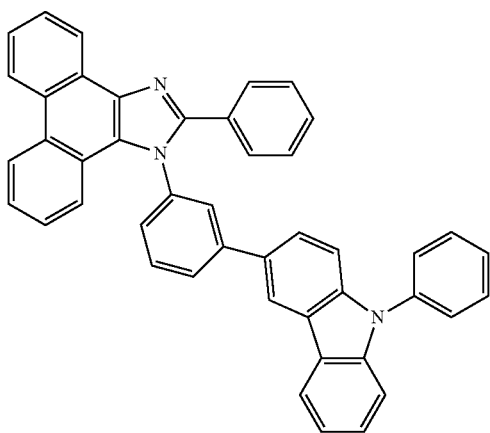

Colorless powder; mp 301° C.

$^1$H NMR (400 MHz, THF-d$_8$) δ7.27-7.44 (m, 9H), 7.54-7.57 (m, 2H), 7.62-7.73 (m, 8H), 7.78-7.82 (m, 2H), 7.85 (dd, J=8.6, 1.6 Hz, 1H), 8.19 (d, J=8.0 Hz, 1H), 8.21 (d, J=1.6 Hz, 1H), 8.31 (d, J=8.0 Hz, 1H), 8.72-8.74 (m, 2H), 8.90 (d, J=8.8 Hz, 1H), 8.95 (d, J=8.4 Hz, 1H), $^{13}$C NMR (100 MHz, CDCl$_3$) δ110.2, 110.6, 119.4, 120.8, 120.8, 121.4, 122.5, 123.1, 123.3, 124.0, 124.2, 125.0, 125.6, 125.7, 126.2, 127.1, 127.2, 127.2, 127.3, 127.6, 128.0, 128.2, 128.3, 128.3, 128.3, 128.7, 129.0, 129.5, 129.7, 130.7, 130.8, 130.8, 131.3, 137.0, 130.8, 130.8, 131.3, 137.0, 137.1, 139.4, 140.5, 141.1, 142.9, 151.1.

MALDI-TOF-MS (positive, Dithranol) m/z: calcd. for C$_{45}$H$_{29}$N$_3$; 611 (M$^+$). found: 612 ([M+H]$^+$).

Embodiment 3

Synthesis of 2-phenyl-1-(3-pyrido(2,3-b)indole-9-yl-phenyl)-1H-phenanthro-[9,10-d]imidazole Add dimethylacetamide (400 ml) to a mixture of 1-(3-bromobenzene)-2-phenyl-1H-phenanthro-[9,10-d] imidazole (22.8 g), α-carboline (9.4 g), cupric iodide (I) (9.7 g) and potassium carbonate (28.1 g). After heating under reflux for 48 hours, add water (2 L), and continue stirring for 30 minutes. Then filter out a powder, and wash with methanol. Recrystallize the solid obtained using tetrahydrofuran to obtain a white colored solid of 2-phenyl-1-(3-pyrido[2,3-b]indole-9-yl-phenyl)-1H-phenanthro-[9,10-d] imidazole (4.6 g, 17% yield), (Compound 38)

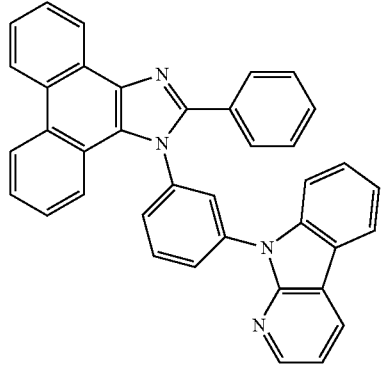

Colorless solid; mp 273° C.

$^1$HNMR (400 MHz, THF-d$_8$) δ7.23-7.29 (m, 3H), 7.32-7.39 (m, 5H), 7.51 (td, J=7.8, 1.2 Hz, 1H), 7.60 (td, J=7.8, 1.2 Hz, 1H), 7.66-7.70 (m, 3H), 7.79-7.81 (m, 2H), 7.86 (t, 8.0 Hz, 1H), 8.09-8.15 (m, 3H), 8.41 (dd, J=4.8, 2.0 Hz, 1H), 8.45 (dd, J=7.6, 1.6 Hz, 1H), 8.77 (d, J=8.4 Hz, 1H), 8.81 (dd, J=8.0, 1.2 Hz, 1H), 8.85 (d, J=8.4 Hz, 1H), $^{13}$C NMR (100 MHz, THF-d$_8$) δ111.0, 117.3, 117.5, 121.9, 122.1, 122.2, 123.5, 124.0, 124.1, 125.0, 125.6, 126.2, 127.1, 127.7, 127.9, 128.5, 128.6, 128.9, 129.0, 129.2, 129.3, 129.4, 130.2, 131.6, 132.1, 138.6, 139.1, 140.3, 140.9, 147.2, 151.7, 152.6.

MALDI-TOF-MS (positive, Dithranol) m/z: calcd. for C$_{38}$H$_{24}$N$_4$; 536 (M$^+$). found: 537 ([M+H]$^+$).

Embodiment 4

Synthesis of 1-[3-(4,6-diphenyl-[1,3,5]-triazine-2-yl)phenyl)-2-phenyl-1H-phenanthro-[9,10-d] imidazole In an argon atmosphere at −70° C., spend 20 minutes to add 1.6M butyl lithium n-hexane solution (67.0 ml) drop by drop to a dried THF (400 ml) solution of 1-(3-bromophenyl)-2-phenyl-1H-phenanthro-[9,10-d]imidazole (40.0 g) obtained from Reference Example 1. Then, after stirring the reaction solution at −70° C. for 30 minutes, spend 10 minutes adding trimethyl borate (60.0 ml) drop by drop, and after raising the temperature of the reaction solution until it is at room-temperature while stirring for 2 hours, add 5% hydrochloric acid (1.3 L) and ethyl acetate (1.3 L) and stir for a further 30 minutes. After drying the resulting organic layer using magnesium sulfate, concentrate and dry to obtain a crude compound of 1-[3-(dihydroxyboryl)phenyl]-2-phenyl-1H-phenanthro-[9,10-d] imidazole (44.4 g), Next, in a nitrogen atmosphere, add degassed toluene (400 ml), methanol (200 ml) and 2M sodium carbonate aqueous solution (400 ml) to a mixture of 1-[3-(dihydroxyboryl) phenyl]-2-phenyl-1H-phenanthro-[9,10-d] imidazole (44.4 g), 2-chloro-4,6,-diphenyl-1,3,5-triazine (54.5 g) and tetrakis(triphenylphosphine) palladium (0) (2.5 g). After heating under reflux for 3 hours, cool the reaction mixture until it is at room-temperature. After drying the resulting organic layer using magnesium sulfate, concentrate, dry and recrystallize using tetrahydrofuran to obtain a yellow colored solid of 1-[3-(4,6-diphenyl-(1,3,5-triazine-2-yl)phenyl]-2-phenyl-1H-phenanthro-[9,10-d] imidazole (10.8 g, 20% yield), (Compound 39)

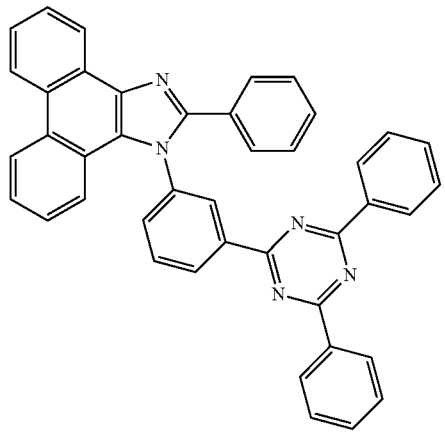

Yellow powder; m.p 299° C.
$^1$H NMR (400 MHz, THF-d$_8$) δ7.20 (dd, J=8.4, 1.2 Hz, 1H), 7.32-7.38 (m, 5H), 7.53-7.63 (m, 5H), 7.67-7.72 (m, 5H), 7.82 (t, J=7.6 Hz, 1H), 8.00 (t, J=7.8 Hz, 1H), 8.12-8.15 (m, 1H), 8.71-8.76 (m, 5H), 8.91 (d, J=8.4 Hz, 1H), 8.96 (d, J=8.0 Hz, 1H), 9.01 (t, J=1.8 Hz, 1H), 9.10 (dt, J=8.0, 1.2 Hz, 1H),
$^{13}$C NMR (100 MHz, CDCl$_3$) δ120.7, 122.5, 123.0, 124.2, 125.1, 125.8, 126.3, 127.2, 127.3, 128.0, 128.2, 128.4, 128.8, 129.0, 129.3, 129.5, 129.6, 129.8, 130.7, 130.8, 131.6, 133.7, 134.2, 135.6, 137.0, 138.1, 139.6, 151.1, 170.4, 171.4.

MALDI-TOF-MS (positive, Dithranol) m/z: calcd. for C$_{42}$H$_{27}$N$_5$; 601 (M$^+$). found: 602 ([M+H]$^+$).

Embodiment 5

Synthesis of 1-[3-(4,6-diphenyl-[1,3,5]-triazine-2-yl)phenyl)-1H-phenanthro-[9,10-d]

In an argon atmosphere at −70° C., spend 20 minutes adding 1.6M butyl lithium n-hexane solution (50.0 ml) drop by drop to a dried THF (350 ml) in solution of 1-(3-bromophenyl)-2-(2-naphthyl)-1H-phenanthro-[9,10-d] imidazole (35.0 g) obtained from Reference Example 2. Then, after stirring the reaction solution. at −70° C. for 30 minutes, spend 10 minutes adding trimethyl borate (45 ml) drop by drop, and after raising the temperature until it is at room-temperature while stirring for 2 hours, add 5% hydrochloric acid (1.0 L) and ethyl acetate (1.0 L) and stir for a further 30 minutes. After drying the resulting organic layer using magnesium sulfate, concentrate and dry to obtain a compound of 1-[3-(dihydroxyboryl) phenyl]-2-(2-naphthyl)-1H-phenanthro-[9,10-d] imidazole (38.6 g), Next, in a nitrogen atmosphere, add degassed toluene (360 ml), methanol (180 ml) and 2M sodium carbonate aqueous solution (360 ml) to a mixture of 1-[3-(dihydroxyboryl) phenyl]-2-(2-naphthyl)-1H-phenanthro-[9,10-d] imidazole (38.6 g), 2-chloro-4,6-diphenyl-1,3,5-triazine (42.0 g) and tetrakis(triphenylphosphine) palladium (0) (1.9 g). After heating under reflux for 6 hours, cool the reaction mixture until it is at room-temperature, and then filter out the solid and recrystallize using THF to obtain a yellow colored solid of 1-[3-(4,6-diphenyl-[1,3,5]-triazine-2-yl) phenyl]-2-(2-naphthyl)-1H-phenanthro-[9,10-d] (14.0 g, 26% yield), (Compound 40)

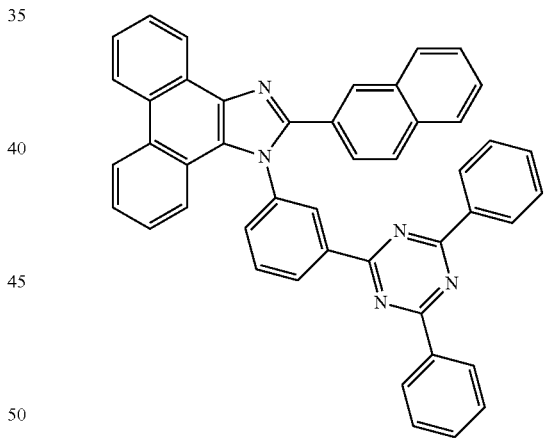

Yellow powder; mp 282° C.
$^1$H NMR (400 MHz, THF-d$_8$) δ7.09-7.13 (m, 1H), 7.22-7.29 (m, 3H), 7.31-7.39 (m, 5H), 7.41-7.45 (m, 2H), 7.49-7.53 (m, 2H), 7.59-7.66 (m, 3H), 7.79 (t, J=7.6 Hz, 1H), 7.82-7.85 (m, 1H), 7.85 (dd, J=9.0, 1.8 Hz, 1H), 7.99 (s, 1H), 8.61-8.63 (m, 4H), 8.66 (d, J=8.4 Hz, 1H), 8.72 (d, J=8.0 Hz, 1H), 8.79 (dd, J=8.0, 1.2 Hz, 1H), 9.04 (dt, J=7.6, 1.6 Hz, 1H), 9.08 (t, J=1.6 Hz, 1H)
$^{13}$C NMR (100 MHz, CDCl3) δ120.7, 122.6, 123.1, 123.2, 124.1, 124.7, 125.3, 126.1, 126.2, 126.5, 126.9, 127.4, 127.5, 127.6, 128.3, 128.4, 128.5, 128.6, 128.9, 129.3, 129.4, 130.1, 130.7, 132.6, 133.0, 133.2, 133.4, 135.9, 137.8, 138.7, 140.2, 150.4, 170.4, 1704, 1701.9.

MALDI-TOF-MS (positive, Dithranol) m/z: calcd. for C$_{46}$H$_{29}$N$_5$; 651 (M$^+$). found: 652 ([M+H]$^+$).

Embodiment 6

Synthesis of 1-[3-(4,6-diphenyl-[1,3,5]triazine-2-yl) phenyl]-2-phenyl)-2-pyridine-4-yl-1H-phenanthro-[9,10-d] imidazole Add acetic acid (70 ml) at 400 to a mixture of 4-pyridylaldehyde (2.2 g) and 3-(4,6-diphenyl-1,3,5-triazine-2-yl) aniline (6.8 g) and stir for 1 hour, after which add 9,10-phenanthrenequinone (4.3 g) and ammonium acetate (1.6 g) at 70° C. and stir for 5 hours. Then, after cooling the reaction mixture until it is at room-temperature, add methanol (300 ml) and cool the mixture down using an ice-bath. Leave standing for 2 hours, filter out the solid, and then wash with methanol. Then use THF to recrystallize the solid obtained to produce a pale yellow colored solid of 1-[3-(4,6-diphenyl-[1,3,5]triazine-2-yl)phenyl]-2-pyridine-4-yl-1H-phenanthro-[9,10-d] imidazole (7.5 g, yield: 60%), (Compound 41)

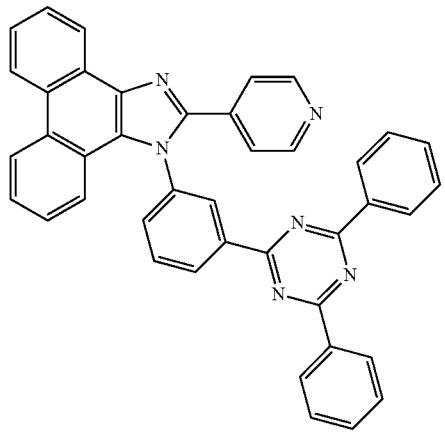

Pale yellow powder; mp 316° C.

$^1$H NMR (400 MHz, THF-d$_8$) δ7.38 (td. J=7.8. 1.2 Hz, 1H), 7.48 (dd. J=8.4. 1.2 Hz, 1H), 7.61-7.68 (m, 5H), 7.71-7.75 (m, 4H), 7.80 (td. J=7.8.1.6 Hz, 1H), 7.88 (td. J=7.7. 1 Hz, 1H), 8.11-8.12 (m, 2H), 8.61-8.62 (m, 2H), 8.90-8.94 (m, 5H), 9.01 (t. J=7.8 Hz, 2H), 9.32-9.38 (2H).

$^{13}$C NMR (100 MHz, THF-d$_8$) δ120.8. 122.3, 122.5, 122.9, 123.2, 124.2, 125.2, 125.7, 126.4, 127.1, 127.4, 128.5, 128.9, 129.0, 129.1, 129.7, 130.5, 131.0, 132.7, 133.1, 135.8, 137.6, 137.8, 139.0, 139.6, 147.6, 149.8.

MALDI-TOF-MS (positive, Dithranol) m/z: calcd. for $C_{41}H_{26}N_6$; 602 (M$^+$). found: 602 (M$^+$).

Embodiment 7

Evaluation of Electroluminescent Device

Use vacuum evaporation to form a plated film of TAPC (1, 1-bis[(di-4-tolylamino)phenyl]cyclohexane) (refer to the undermentioned chemical formula) on an already cleaned, patterned ITO (Indium Tin Oxide) substrate (film thickness: 110 nm), to form a hole transport layer. Then use co-evaporation plating to form a plated film of Ir(ppy)$_3$ (refer to the undermentioned chemical formula) and the imidazole compound of Embodiment 1 on the hole transport layer with a film thickness ratio of 20:1, to form a luminous layer (20 nm). Next, form a plated film of TpPyPB (refer to the undermentioned chemical formula) (50 nm) on an electron transport layer, after which form a film of lithium fluoride (0.5 nm) and aluminum (100 nm) to form a cathode. Then, seal using a glass cover to produce a 2 nm angle electroluminescent device.

Apply voltage to the electroluminescent device to verify its green luminescence. And use I-V-L testing apparatus (manufactured by Japanese Company KONIC MINOLTA (CS-2000)) to evaluate component characteristics (driving voltage (V) and current efficiency (cd/A)) of the electroluminescent device obtained.

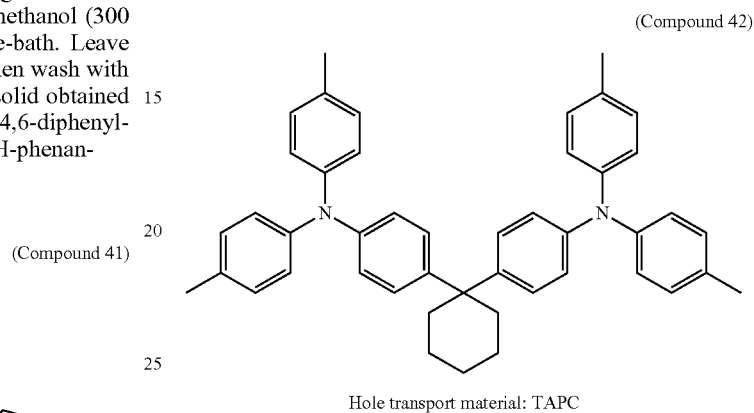

(Compound 42)

Hole transport material: TAPC (Compound 43)

Adulterant: Ir(ppy)$_3$ (Compound 44)

Electron transport material: TpPyPB

Embodiment 8

Apart from changing the imidazole compound of Embodiment 1 used in Embodiment 7 to the imidazole compound synthesized in Embodiment 2, the electroluminescent device is produced in the same way.

Apply voltage to the electroluminescent device to verify its green luminescence. And using the same method as in Embodiment 7, evaluate the driving voltage (V) and current efficiency (cd/A) of the electroluminescent device obtained.

Comparative Example 1

Apart from changing the imidazole compound of Embodiment 1 used in Embodiment 7 to a general host compound, namely CBP (refer to the undermentioned chemical formula), an electroluminescent device is produced in the same way.

Apply voltage to the electroluminescent device to verify its green luminescence. And using the same method as in Embodiment 7, evaluate the driving voltage (V) and current efficiency (cd/A) of the electroluminescent device obtained.

(Compound 45)

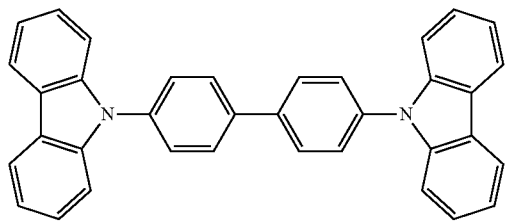

Host material: CBP

Figure 2:
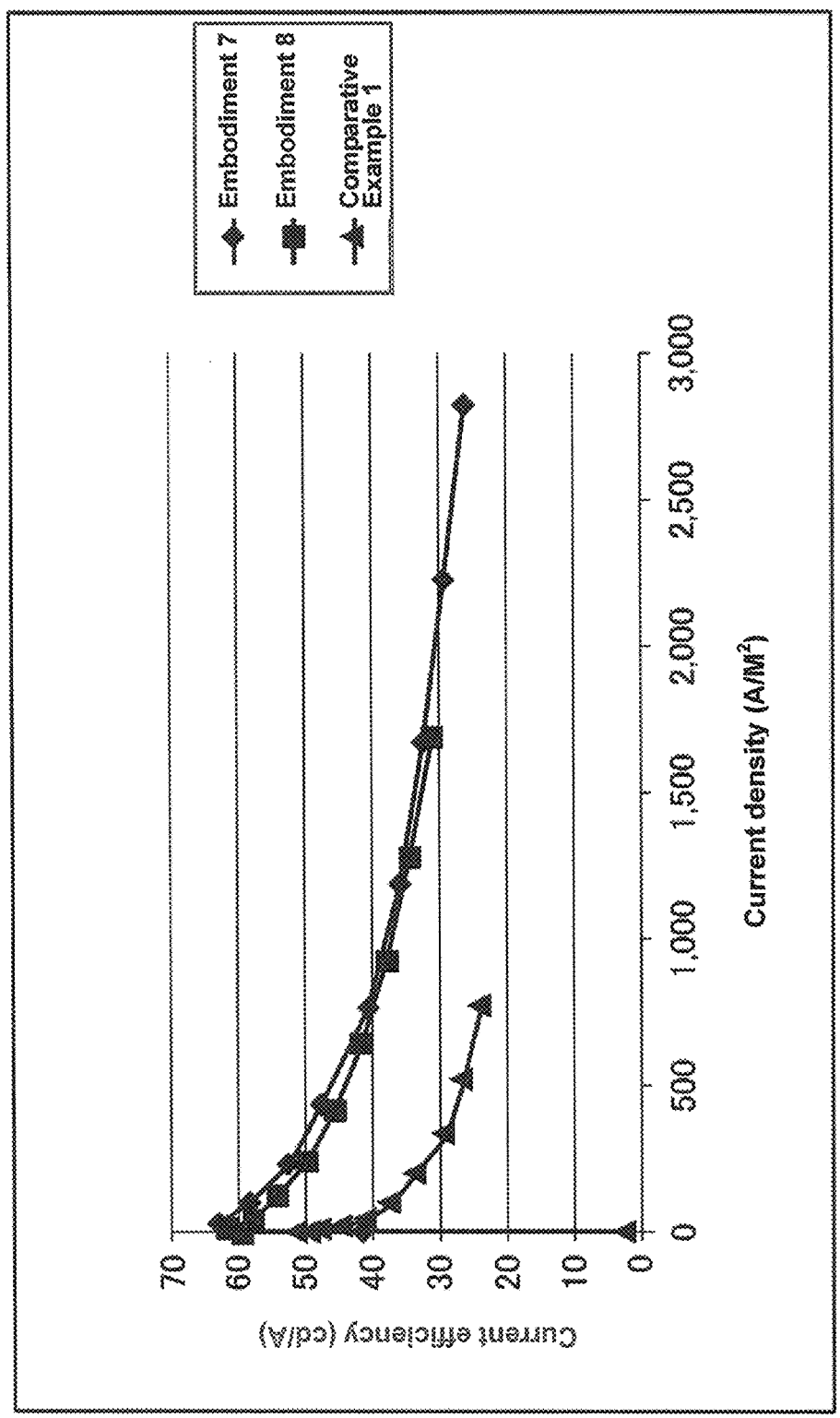
FIG. 2 shows a current density and current efficiency relation graph of an electroluminescent device structured according to embodiments 7, 8 and comparative example 1.

Table 1 shows the driving voltage of 1,000 cd/m² and current efficiency of the electroluminescent devices produced according to the aforementioned embodiments 7, 8 and the comparative example 1. FIG. 1 and FIG. 2 show a comparison of luminescent brightness—voltage characteristics and current efficiency—current density of the electroluminescent devices.

TABLE 1

Component evaluation results (@1,000 cd/m²)

| | Host material | Driving voltage (V) | Current efficiency (cd/A) |
|---|---|---|---|
| Embodiment 7 | Embodiment 1 | 3.8 | 62.6 |
| Embodiment 8 | Embodiment 2 | 4.0 | 71.7 |
| Comparative Example 1 | CBP | 5.2 | 43.8 |

Embodiment 9

Use vacuum evaporation to form a plated film of HAT-CN (refer to the undermentioned chemical formula) (1 nm). Next, form a film of HT1 (refer to the undermentioned chemical formula) (40 nm) on an already cleaned, patterned ITO (Indium Tin Oxide) substrate (film thickness: 110 nm), to form a hole injection layer and a hole transport layer. Then use co-evaporation plating to form a plated film of Ir(ppy) 3 and the imidazole compound synthesized in Embodiment 4 on the hole injection layer and the hole transport layer with a film thickness ratio of 1:20, to form a luminous layer (20 nm). Next, use co-evaporation plating to form a plated film of ET1 and Liq (refer to the undermentioned chemical formulas) on an electron transport layer (50 nm) with a film thickness ratio of 1:1, after which form a film of lithium fluoride (0.5 nm) and aluminum (100 nm) to form a cathode. Then seal using a glass cover to produce an electroluminescent device with an area of 2 mm×2 mm. Apply voltage to the electroluminescent device to verify its green luminescence. And using the same method as in Embodiment 7, evaluate the driving voltage (V) and current efficiency (cd/A) of the electroluminescent device obtained.

(Compound 46)

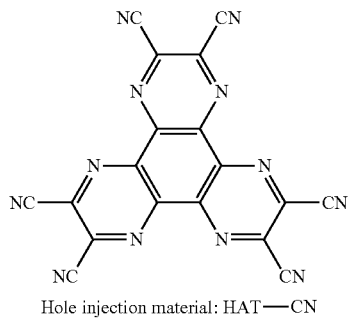

Hole injection material: HAT—CN (Compound 47)

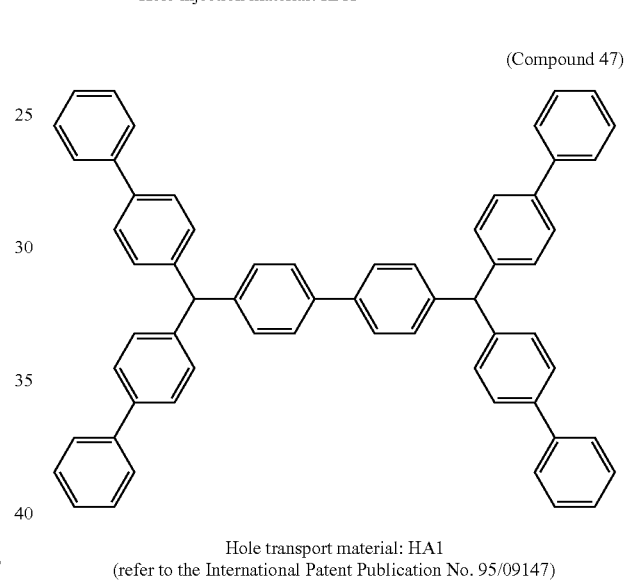

Hole transport material: HA1
(refer to the International Patent Publication No. 95/09147)

(Compound 48)

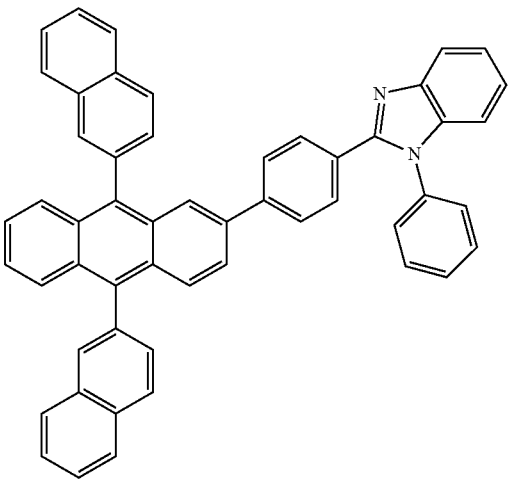

Eletron transport material: ET1 (refer to the Japanese Patent Publication No. 2005-515233 bulletin)

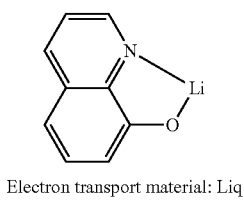

(Compound 49)

Electron transport material: Liq

Comparative Example 2

Apart from changing the imidazole compound of Embodiment 4 used in Embodiment 9 to a general host compound, namely CBP, an electroluminescent device is produced in the same way.

Apply voltage to the electroluminescent device to verify its green luminescence. And using the same method as in Embodiment 7, evaluate the driving voltage (V) and current efficiency (cd/A) of the electroluminescent device obtained.

Figure 3:
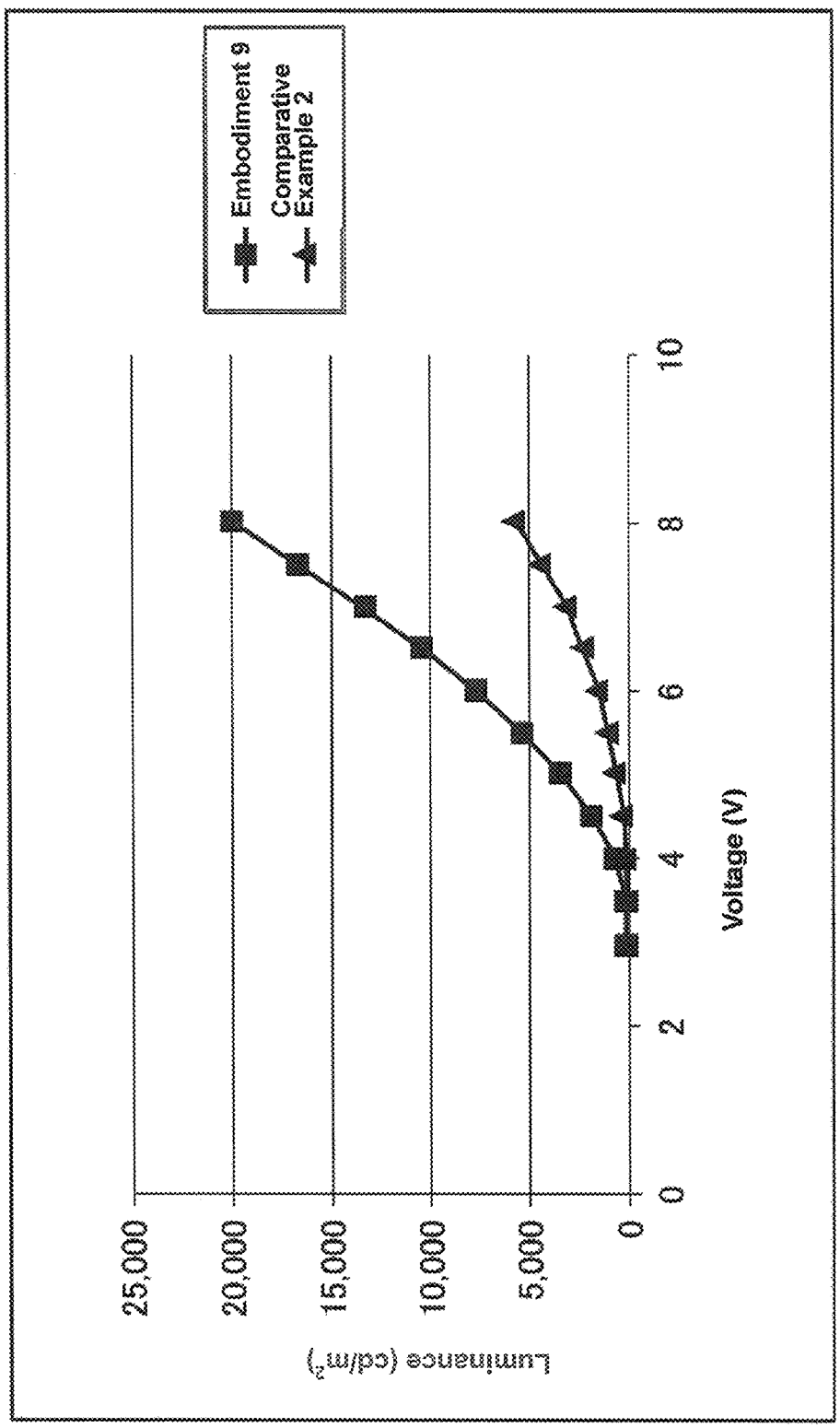
FIG. 3 shows a voltage-light characteristic graph of an electroluminescent device structured according to embodiment 9 and comparative example 2.
Figure 4:
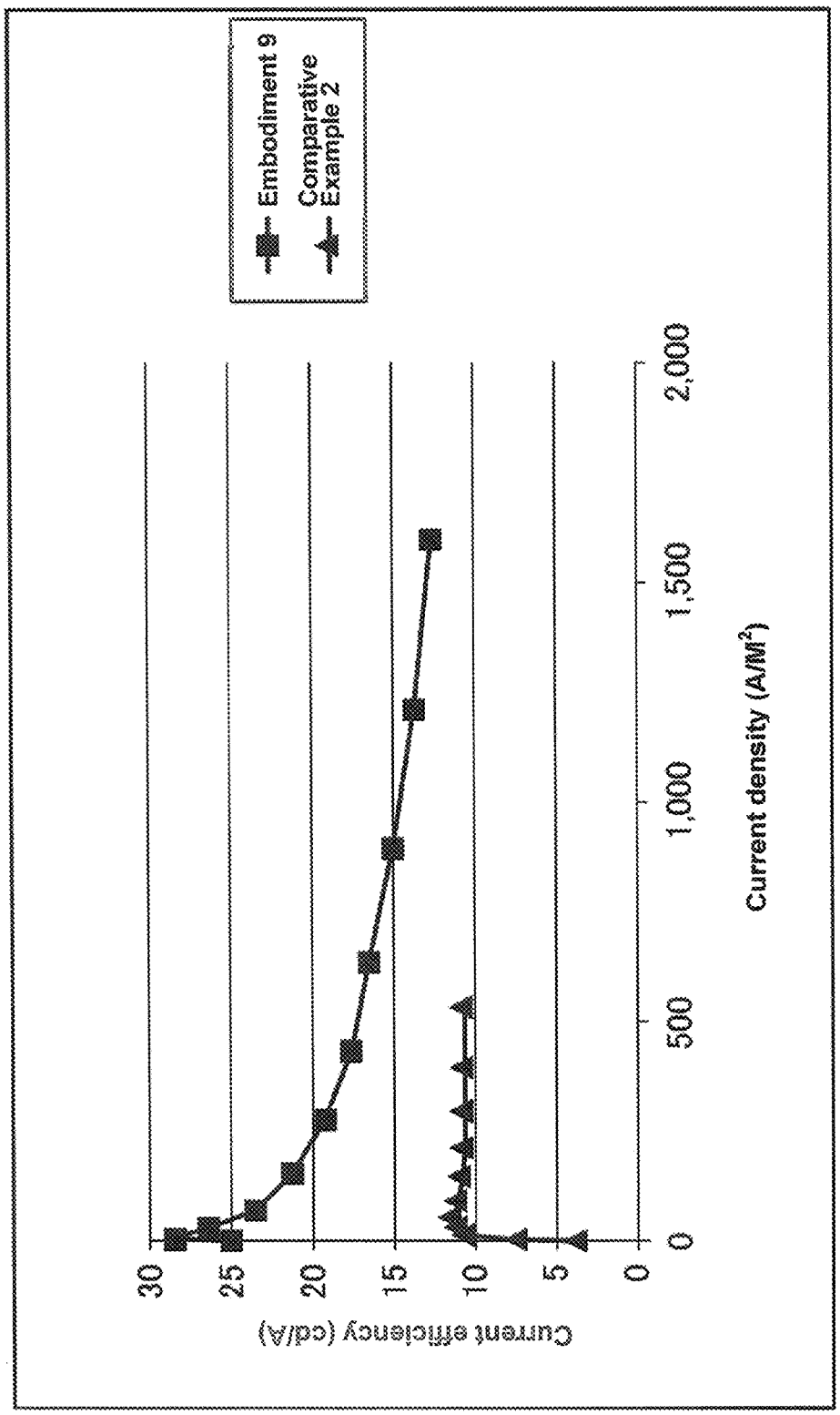
FIG. 4 shows a current density and current efficiency relation graph of an electroluminescent device structured according to embodiment 9 and comparative example 2.

Table 2 shows the driving voltage of 1,000 cd/m² and current efficiency of the electroluminescent device produced according to the aforementioned embodiment 9 and comparative example 2. FIG. 3 and FIG. 4 show a comparison of luminescent brightness—voltage characteristics and current efficiency—current density of the electroluminescent devices.

TABLE 2

Component evaluation results (@1,000 cd/m²)

|  | Host material | Driving voltage (V) | Current efficiency (cd/A) |
| --- | --- | --- | --- |
| Embodiment 9 | Embodiment 4 | 4.3 | 25.6 |
| Comparative Example 2 | CBP | 5.4 | 11.4 |

Embodiment 10

Use vacuum evaporation plating to form a plated film of HAT-CN (1 nm). Next, form a film of HT1 (40 nm) on an already cleaned, patterned ITO substrate (film thickness: 150 nm), to form a hole injection layer and a hole transport layer. Then use co-evaporation plating to form a plated film of Ir(pic)$_3$ (refer to the undermentioned chemical formula) and the imidazole compound synthesized in Embodiment 5 on the hole injection layer and the hole transport layer with a film thickness ratio of 1:20, to form a luminous layer (20 nm). Next, use co-evaporation plating to form a plated film of ET1 and Liq on an electron transport layer (50 nm) with a film thickness ratio of 1:1, after which form a film of lithium fluoride (0.5 nm) and aluminium (100 nm) to form a cathode. Then seal using a glass cover to produce a 2 nm angle electroluminescent device.

Apply voltage to the electroluminescent device to verify its green luminescence. And using the same method as in Embodiment 7, evaluate the driving voltage (V) and current efficiency (cd/A) of the electroluminescent device obtained.

Comparative Example 3

Apart from changing the imidazole compound of Embodiment 5 used in Embodiment 10 to a general host compound, namely CBP, an electroluminescent device is produced in the same way.

Apply voltage to the electroluminescent device to verify its green luminescence. And using the same method as in Embodiment 7, evaluate the driving voltage (V) and current efficiency (cd/A) of the electroluminescent device obtained.

Figure 5:
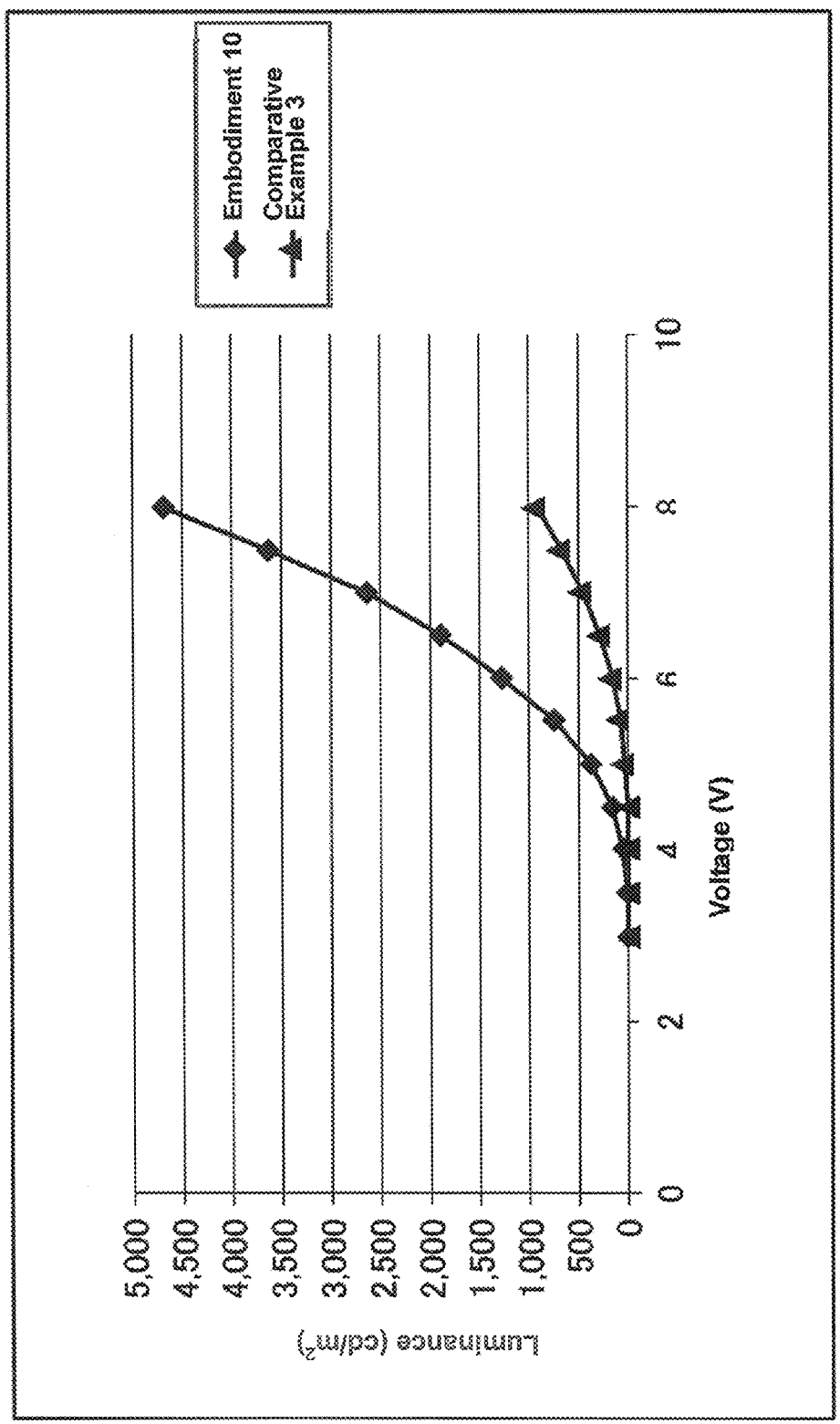
FIG. 5 shows a voltage-light characteristic graph of an electroluminescent device structured according to embodiment 10 and comparative example 3.
Figure 6:
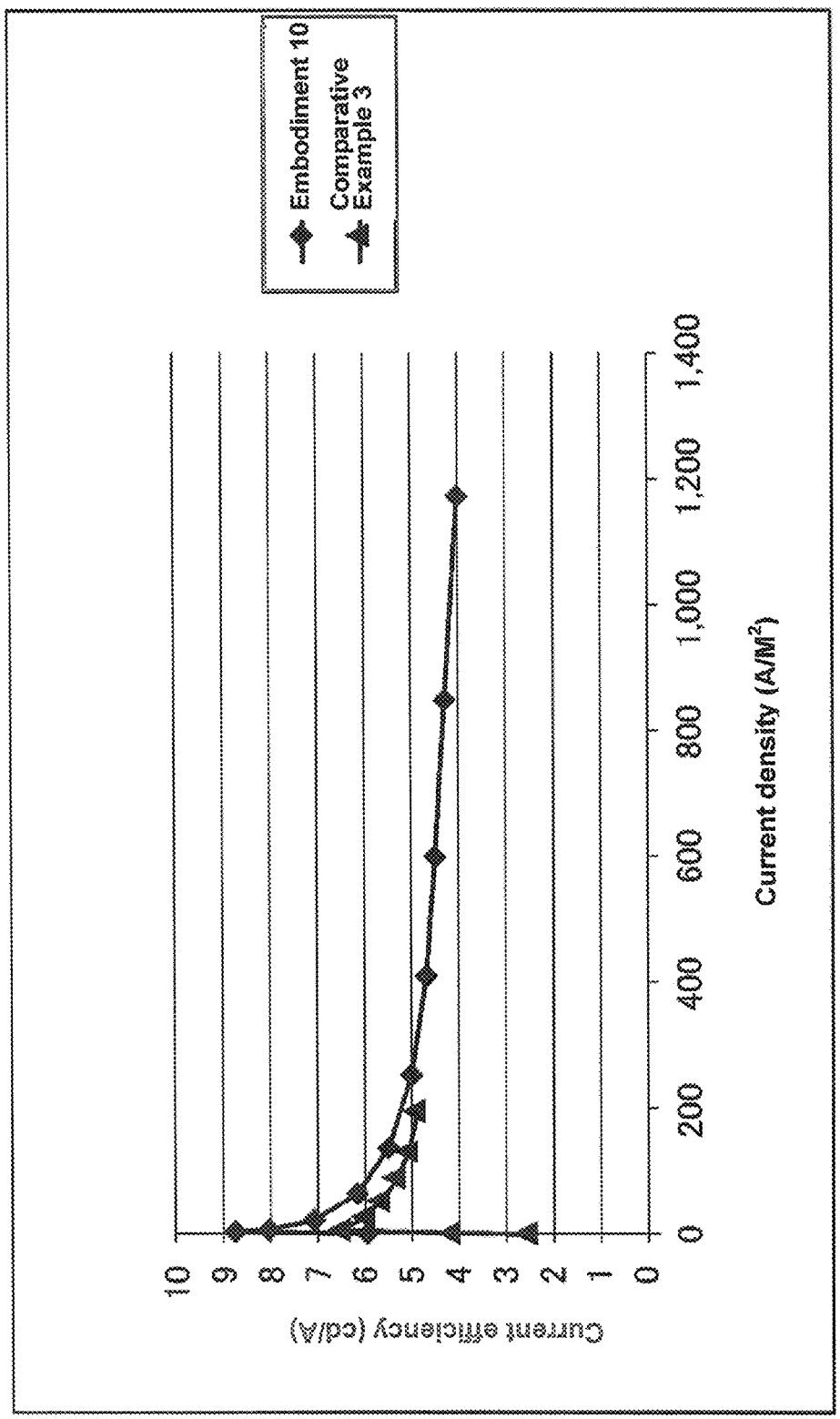
FIG. 6 shows a current density and current efficiency relation graph of an electroluminescent device structured according to embodiment 10 and comparative example 3.

Table 3 shows the driving voltage of 1,000 cd/m² and current efficiency of the electroluminescent device produced according to aforementioned embodiment 10 and comparative example 3. FIG. 5 and FIG. 6 show a comparison of luminescent brightness—voltage characteristics and current efficiency—current density of the electroluminescent devices.

TABLE 3

Component evaluation results (@1,000 cd/m²)

|  | Host material | Driving voltage (V) | Current efficiency (cd/A) |
| --- | --- | --- | --- |
| Embodiment 10 | Embodiment 5 | 5.7 | 5.2 |
| Comparative Example 3 | CBP | 8.1 | 4.9 |

It may be seen from the results of Tables 1~3 and FIGS. 1~6 that the driving voltage is lower and the current efficiency is higher for the electroluminescent devices using the imidazole compound of the present invention (Embodiments 7~10) compared to the electroluminescent devices using CBP (Comparative Examples 1~3). Hence, it may be seen from these results that using imidazole compound of the present invention enables achieving the advantageous characteristic of low driving voltage, to produce stable and high quantum efficient electroluminescent devices.

INDUSTRIAL USABILITY

Materials for electronic device use containing the new imidazole compound of the present invention may be applied in various types of electronic devices such as electroluminescent devices or organic thin-film solar cells. Examples of which include: various types of electronic devices such as electroluminescent devices containing organic electroluminescent cells. More specific examples include appropriate use in electronic devices such as flat panel display units (such as: computer displays or wall type televisions) or surface luminous body light sources (such as: lighting, photocopier light sources, backlit light sources for liquid crystal display use, backlit light sources for measuring machines), display panels, and marker lights.

It is of course to be understood that the embodiments described herein are merely illustrative of the principles of the invention and that a wide variety of modifications thereto may be effected by persons skilled in the art without departing from the spirit and scope of the invention as set forth in the following claims.

What is claimed is:

1. An imidazole compound, represented by the following formula (1),

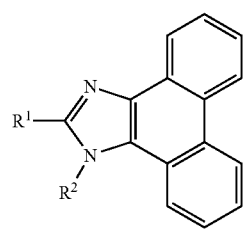

(1)

in the formula (1), $R^1$ is an alkyl having a carbon number of 1~24, an aryl having a carbon number 6~24, or an aromatic heterocyclic group having a carbon number 1~24, $R^2$ is a functional group represented by the undermentioned formula (2)

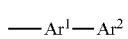
(2)

in the formula (2), $Ar^1$ is an aryl chain, or an aromatic heterocyclic chain, $Ar^2$ is a functional group represented by the undermentioned formulas (3), (4), (6) or (7)

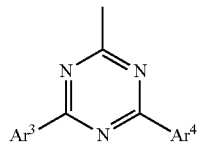
(3)

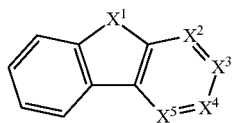
(4)

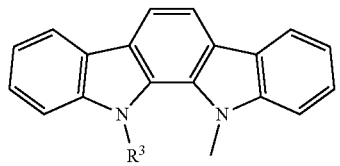
(6)

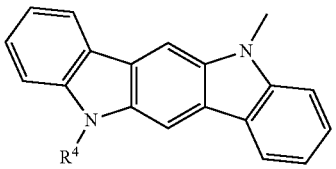
(7)

in the formula (3), $Ar^3$ and $Ar^4$ are respectively independent, aromatic groups having a carbon number of 6~20, or aromatic heterocyclic groups having a carbon number of 5~18; in the formula (4), $X^1$ is an oxygen atom, a sulfur atom, or a nitrogen atom with a substituent including an alkyl, an aryl, or an aromatic heterocyclic group; in the formulas (4), $X^2$~$X^5$ are respectively independent, nitrogen atoms, or carbon atoms; $R^3$ in formula (6) and $R^4$ in formula (7) are separately an alkyl having a carbon number of 1~24, an aryl having a carbon number of 6~24, or an aromatic heterocyclic group having a carbon number of 1~24.

2. A material for electronic device, containing the imidazole compound as described in claim 1.

3. An electroluminescent device, containing material for electronic device as described in claim 2.

4. The electroluminescent device, containing material for electronic device as described in claim 2 as a host material.

5. The electroluminescent device, containing material for electronic device as described in claim 2 as a hole blocking material.

6. The electroluminescent device, containing material for electronic device as described in claim 2 as an electron transport material.

7. An electronic device, containing the electroluminescent device as described in claim 3.

8. An electronic device, containing the electroluminescent device as described in claim 4.

9. An electronic device, containing the electroluminescent device as described in claim 5.

10. An electronic device, containing the electroluminescent device as described in claim 6.

* * * * *